US011708590B2

(12) United States Patent
Nielsen et al.

(10) Patent No.: US 11,708,590 B2
(45) Date of Patent: Jul. 25, 2023

(54) SYNTHETIC METABOLIC FUNNELING FOR BIOCHEMICAL PRODUCTION

(71) Applicant: ARIZONA BOARD OF REGENTS ON BEHALF OF ARIZONA STATE UNIVERSITY, Scottsdale, AZ (US)

(72) Inventors: David Nielsen, Tempe, AZ (US); Brian Thompson, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 3 days.

(21) Appl. No.: 16/631,232

(22) PCT Filed: Jul. 16, 2018

(86) PCT No.: PCT/US2018/042324

§ 371 (c)(1),
(2) Date: Jan. 15, 2020

(87) PCT Pub. No.: WO2019/018302

PCT Pub. Date: Jan. 24, 2019

(65) Prior Publication Data

US 2020/0216865 A1 Jul. 9, 2020

Related U.S. Application Data

(60) Provisional application No. 62/533,997, filed on Jul. 18, 2017.

(51) Int. Cl.

*C12P 7/18* (2006.01)
*C12P 7/46* (2006.01)
*C12N 9/02* (2006.01)
*C12N 9/88* (2006.01)
*C12N 9/90* (2006.01)
*C12P 7/22* (2006.01)

(52) U.S. Cl.

CPC .............. *C12P 7/46* (2013.01); *C12N 9/0069* (2013.01); *C12N 9/0073* (2013.01); *C12N 9/88* (2013.01); *C12N 9/90* (2013.01); *C12P 7/22* (2013.01); *C12Y 113/11001* (2013.01); *C12Y 114/13002* (2013.01); *C12Y 114/13007* (2013.01); *C12Y 401/01061* (2013.01); *C12Y 401/01063* (2013.01); *C12Y 401/01091* (2013.01); *C12Y 401/0304* (2013.01); *C12Y 401/99002* (2013.01); *C12Y 402/0101* (2013.01); *C12Y 402/99021* (2013.01); *C12Y 504/04002* (2013.01)

(58) Field of Classification Search

CPC .................................... C12P 7/18; C12P 7/22
See application file for complete search history.

(56) References Cited

U.S. PATENT DOCUMENTS

| | | | | |
|---|---|---|---|---|
| 3,660,235 | A | 5/1972 | Okumura et al. | |
| 4,681,852 | A | 7/1987 | Tribe | |
| 5,616,496 | A | 4/1997 | Frost et al. | |
| 6,472,190 | B1 | 10/2002 | Frost | |
| 9,150,884 | B2 | 10/2015 | Nielsen et al. | |
| 9,944,955 | B1 | 4/2018 | Wang et al. | |
| 10,125,377 | B2 | 11/2018 | Nielsen et al. | |
| 10,174,346 | B2 | 1/2019 | Nielsen et al. | |
| 10,246,726 | B2 | 4/2019 | Wang et al. | |
| 10,844,405 | B2 | 11/2020 | Nielsen et al. | |
| 2010/0317069 | A1 | 12/2010 | Burk et al. | |
| 2013/0030215 | A1 | 1/2013 | Bui et al. | |
| 2015/0064750 | A1 | 3/2015 | Osterhout et al. | |
| 2015/0225751 | A1 | 8/2015 | Yan et al. | |
| 2016/0160244 | A1 | 6/2016 | Nielsen et al. | |
| 2017/0145447 | A1 | 5/2017 | Yan et al. | |
| 2018/0237813 | A1* | 8/2018 | Noda | C12P 7/42 |
| 2018/0312887 | A1* | 11/2018 | Lynch | C07C 53/126 |
| 2020/0216865 | A1 | 7/2020 | Nielsen et al. | |
| 2020/0231992 | A1 | 7/2020 | Nielsen et al. | |

FOREIGN PATENT DOCUMENTS

| | | | |
|---|---|---|---|
| WO | 2012122333 | A1 | 9/2012 |
| WO | 2013116244 | A1 | 8/2013 |
| WO | 2013172928 | A1 | 11/2013 |
| WO | 2015031048 | A1 | 3/2015 |
| WO | 2015041776 | A1 | 3/2015 |

(Continued)

OTHER PUBLICATIONS

Geneseq Accession No. BAL59654, published Apr. 25, 2013 (Year: 2013).*
Geneseq Accession No. AEJ18922, published Oct. 5, 2006 (Year: 2006).*
Geneseq Accession No. AWL40388, published Jul. 23, 2009 (Year: 2009).*
Geneseq Accession No. AZY49236, published Sep. 27, 2012 (Year: 2012).*
Geneseq Accession No. BCM56463, published Apr. 21, 2016 (Year: 2016).*
Adkins, J , et al., "Engineering microbial chemical factories to produce renewable 'biomonomers'", Frontiers in Microbiology 3(313), 1-12 (2012).

(Continued)

*Primary Examiner* — Tekchand Saidha
(74) *Attorney, Agent, or Firm* — Viksnins Harris Padys Malen LLP

(57) ABSTRACT

Certain embodiments provide a method for preparing a biochemical product (e.g., phenol, catechol, or muconic acid, or a salt thereof). For example, such methods include contacting a recombinant host having two or more recombinant pathways with a fermentable carbon source and growing the recombinant cell for a time sufficient to synthesize the product. In certain embodiments, each recombinant pathway: 1) is capable of producing the same final biochemical product; 2) comprises at least one gene encoding a polypeptide; 3) is derived from a different endogenous metabolite as its immediate precursor; and 4) converges to the same final product or the same intermediate metabolite.

15 Claims, 8 Drawing Sheets

Specification includes a Sequence Listing.

(56) References Cited

FOREIGN PATENT DOCUMENTS

WO 2019018302 A1 1/2019
WO 2019023019 A1 1/2019

OTHER PUBLICATIONS

Averesch, N , et al., "Tailoring strain construction strategies for muconic acid production in S cerevisiae and *E. coli*". Metabolic Engineering Communications 1, 19-28 (2014).
Bongaerts, J , et al., "Metabolic Engineering for Microbial Production of Aromatic Amino Acids and Derived Compounds", Metabolic Engineering 3(4), 289-300 (2001).
Bouwer, E , et al., "Bioremediation of organic compounds—putting microbial metabolism to work", Trends in Biotechnology 11(8), 360-367 (1993).
Cafaro, V , et al., "Expression and purification of the recombinant subunits of toluene/o-xylene monooxygenase and reconstitution of the active complex", European Journal of Biochemistry 269(22), 5689-5699 (2002).
Cafaro, V , et al., "Phenol Hydroxylase and Toluene/o-Xylene Monooxygenase from Pseudomonas stutzeri OX1: Interplay between Two Enzymes", Applied and Environmental Microbiology 70(4), 2211-2219 (2004).
Camara, B , et al., "A Gene Cluster Involved in Degradation of Substituted Salicylates via ortho Cleavage in *Pseudomonas* sp. Strain MT1 Encodes Enzymes Specifically Adapted for Transformation of 4-Methylcatechol and 3-Methylmuconate", Journal of Bacteriology 189(5), 1664-1674 (2007).
Cao, B , et al., "Induction of ortho- and meta-cleavage pathways in Pseudomonas in biodegradation of high benzoate concentration: MS identification of catabolic enzymes", Applied Microbiology and Biotechnology 81, 99-107 (2008).
Castano-Cerezo, S , et al., "An insight into the role of phosphotransacetylase (pta) and the acetate/acetyl-CoA Tode in *Escherichia coli*", Microbial Cell Factories 8(54), 1-19 (2009).
Curran, K , et al., "Metabolic engineering of muconic acid production in *Saccharomyces cerevisiae*", Metabolic Engineering 15, 55-66 (2013).
Dahm, C , et al., "The role of isochorismate hydroxymutase genes entC and menF in enterobactin and menaquinone biosynthesis in *Escherichia coli*", Biochimica et Biophysica Acta—General Subjects 1425(2), 377-386 (1998).
Datsenko, Kirill A., et al., "One-step inactivation of chromosomal genes in *Escherichia coli* K-12 using PCR products", PNAS vol. 97 (12), 6640-6645 (2000).
Deng, Y , et al., "Biological production of adipic acid from renewable substrates: Current and future methods", Biochemical Engineering Journal 105(Part A), 16-26 (2016).
Douglas, C , "Phenylpropanoid metabolism and lignin biosynthesis: from weeds to trees", Trends in Plant Science 1 (6), 171-178 (1996).
Draths, K , et al., "Environmentally compatible synthesis of adipic acid from D-glucose", Journal of the American Chemical Society 116(1), 399-400 (1994).
Fullenkamp, D , et al., "pH-dependent cross-linking of catechols through oxidation via Fe3+ and potential implications for mussel adhesion", RSC Advances 4, 25127-25134 (2014).
Gibson, D , et al., "Enzymatic assembly of DNA molecules up to several hundred kilobases", Nature Methods 6(5), 343-345 (2009).
Gosset, G , "Improvement of *Escherichia coli* production strains by modification of the phosphoenolpyruvate:sugar phosphotransferase system", Microbial Cell Factories 4(14), 1-11 (2005).
Gosset, G , "Production of aromatic compounds in bacteria", Current Opinion in Biotechnology 20(6), 651-658 (2009).
Gruys, K , et al., "Substrate synergism and the steady-state kinetic reaction mechanism for EPSP synthase from *Escherichia coli*", Biochemistry 31(24), 5534-5544 (1992).
Herrmann, K, "The Shikimate Pathway as an Entry to Aromatic Secondary Metabolism", Plant Physiology 107, 7-12 (1995).
Ikeda, M , et al., "Metabolic Engineering To Produce Tyrosine or Phenylalanine in a Tryptophan-Producing Corynebacterium glutamicum Strain", Applied and Environmental Microbiology 58(3), 781-785 (1992).
Iwasaki, Y , et al., "Novel metabolic pathway for salicylate biodegradation via phenol in yeast Trichosporon moniliiforme". Biodegradation 21, 557-564 (2010).
Jindrova, E , et al., "Bacterial aerobic degradation of benzene, toluene, ethylbenzene and xylene", Folia Microbiologica 47, 83-93 (2002).
Juminaga, D , et al., "Modular Engineering of L-Tyrosine Production in *Escherichia coli*", Applied and Environmental Microbiology 78(1), 89-98 (2012).
Kerbarh, O , et al., "Salicylate Biosynthesis: Overexpression, Purification, and Characterization of Irp9, a Bifunctional Salicylate Synthase from Yersinia enterocolitica", Journal of Bacteriology 187(15), 5061-5066 (2005).
Kim, B , et al., "Metabolic engineering of *Escherichia coli* for the production of phenol from glucose", Biotechnology Journal 9(5), 621-629 (2014).
Kukor, J , et al., "Cloning and Expression of the catA and catBC Gene Clusters from Pseudomonas aeruginosa PAO", Journal of Bacteriology 170(10), 4458-4465 (1988).
Lin, Y , et al., "Extending shikimate pathway for the production of muconic acid and its precursor salicylic acid in *Escherichia coli*", Metabolic Engineering 23, 62-69 (2014).
Linger, J , et al., "Lignin valorization through integrated biological funneling and chemical catalysis", Proceedings of the National Academy of Sciences of the United States of America 111(33), 12013-12018 (2014).
Liu, L , et al., "A systems level engineered *E. coli* capable of efficiently producing L-phenylalanine", Process Biochemistry 49(5), 751-757 (2014).
Liu, L , et al., "L-Tryptophan Production in *Escherichia coli* Improved by Weakening the Pta-AckA Pathway", Plos One 11(6), 1-16 (2016).
Neujahr, H , et al., "Phenol Hydroxylase from Yeast. Purification and Properties of the Enzyme from Trichosporon cutaneum", European Journal of Biology 35(2), 386-400 (1973).
Ngai, K-L , et al., "Catechol and chlorocatechol 1,2-Dioxygenases", Methods in Enzymology 188, 122-126 (1990).
Nikodem, P , et al., "New Bacterial Pathway for 4- and 5-Chlorosalicylate Degradation via 4-Chlorocatechol and Mialeylacetate in *Pseudomonas* sp Strain MT1", Journal of Bacteriology 185(23), 6790-6800 (2003).
Niu, W , et al., "Benzene-Free Synthesis of Adipic Acid", Biotechnology Progress 18(2), 201 (2008). pp. 201-211.
Noda, S , et al., "Metabolic design of a platform *Escherichia coli* strain producing various chorismate derivatives", Metabolic Engineering 33, 119-129 (2016).
Nordlund, I, et al., "Complete nucleotide sequence and polypeptide analysis of multicomponent phenol hydroxylase from *Pseudomonas* sp. strain CF600", Journal of Bacteriology 172(12), 6826-6833 (1990).
Notomista, E , et al., "Evolution of Bacterial and Archaeal Multicomponent Monooxygenases", Journal of Molecular Evolution 56, 435-445 (2003).
Patent Cooperation Treaty , International Searching Authority, Search Report for PCT/US2018/042324, 5 pages, dated Oct. 16, 2018.
Patent Cooperation Treaty , International Searching Authority, Written Opinion for PCT/US2018/042324, 28 pages, dated Oct. 15, 2018.
Postma, P , et al., "Phosphoenolpyruvate: Carbohydrate Phosphotransferase Systems of Bacteria", Microbiological Reviews 57(3), 543-594 (1993).
Pugh, S , et al., "Rational engineering of a novel pathway for producing the aromatic compounds p-hydroxybenzoate, protocatechuate, and catechol in *Escherichia coli*", Process Biochemistry 49(11), 1843-1850 (2014).
Qi, W , et al., "Functional expression of prokaryotic and eukaryotic genes in *Escherichia coli* for conversion of glucose to p-hydroxystyrene", Metabolic Engineering 9(3), 268-276 (2007).

(56) References Cited

OTHER PUBLICATIONS

Quan, J , et al., "Circular polymerase extension cloning for high-throughput cloning of complex and combinatorial DNA libraries", Nature Protocols 6(2), 242-251 (2011).
Ren, Y , et al., "Microbial production of phenol via salicylate decarboxylation", RSC Advances 5(112), 92685-92689 (2015).
Rodriguez, A , et al., "Engineering *Escherichia coli* to overproduce aromatic amino acids and derived compounds", Microbial Cell Factories 13(126), 1-15 (2014).
Sengupta, S , et al., "Metabolic Engineering of a Novel Muconic Acid Biosynthesis Pathway via 4-Hydroxybenzoic Acid in *Escherichia coli*", Appl Environ Microbiol 81, 8037-8043 (2015).
Serino, L , et al., "Structural genes for salicylate biosynthesis from chorismate in Pseudomonas aeruginosa", Molecular and General Genetics MGG 249, 217-228 (1995).
Shiloach, J , et al., "Effect of glucose supply strategy on acetate accumulation, growth, and recombinant protein production by *Escherichia coli* BL21 (λDE3) and *Escherichia coli* JM109", Biotechnology and Bioengineering 49(4), 421-428 (1996).
Sonoki, T , et al., "Enhancement of protocatechuate decarboxylase activity for the effective production of muconate from lignin-related aromatic compounds", Journal of Biotechnology 192(Part A), 71-77 (2014).
Sridevi, V , et al., "Metabolic Pathways for the Biodegredation of Phenol", International Journal of Engineering Science & Advanced Technology 2(3), 695-705 (2012).
Sun, X , et al., "A Novel Muconic Acid Biosynthesis Approach by Shunting Tryptophan Biosynthesis via Anthranilate", Applied and Environmental Microbiology 79(13), 4024-4030 (2013).
Sun, X , et al., "Biological Production of Muconic Acid via a Prokaryotic 2,3-Dihydroxybenzoic Acid Decarboxylase", ChemSusChem 7(9), 2478-2481 (2014).
Tao, Y , et al., "Oxidation of Benzene to Phenol, Catechol, and 1,2,3-Trihydroxybenzene by Toluene 4-Monooxygenase of Pseudomonas mendocina KR1 and Toluene 3-Monooxygenase of Ralstonia pickettii PKO1", Applied and Environmental Microbiology 70(7), 3814-3820 (2004).
Terzer, M , et al., "Large-scale computation of elementary flux modes with bit pattern trees", Bioinformatics 24(19), 2229-2235 (2008).
Thompson, B , et al., "Engineering a Modular Network of Non-natural Pathways for Aromatic Chemicals & Muconic Acid", 249th ACS Annual Meeting and Exposition, Denver, CO, Presentation, 46 pages, (2015).
Thompson, B , et al., "Engineering a Modular Network of Non-natural Pathways for Aromatic Chemicals & Muconic Acid", 249th ACS National Meeting and Exposition, Denver, CO, Abstract, 2 pages (2015).
Thompson, B , et al., "Engineering and comparison of non-natural pathways for microbial phenol production", Biotechnology and Bioengineering 113(8), 1745-1754 (2016).
Thompson, B , "Exploring new pathways and strategies for enhancing muconic acid biosynthesis", Society of Industrial Microbiology and Biotechnology Annual Meeting, Denver, CO, Poster, 1 page (Jul. 30, 2017).
Thompson, B , et al., "Exploring new pathways and strategies for enhancing muconic acid biosynthesis", Society of Industrial Microbiology and Biotechnology Annual Meeting, Denver, CO, Abstract, 1 page, (2017).
Thompson, B , et al., "Muconic Acid Production via Alternative Pathways and a Synthetic "Metabolic Funnel"", ACS Synth Biol 7, 565-575 (2018).
Thompson, B , et al., "Muconic Acid Production via Alternative Pathways and a Synthetic "Metabolic Funnel"", ACS Synthetic Biology 7(2), 565 (2017). [Abstract Only].
Tinberg, C , et al., "Multiple Roles of Component Proteins in Bacterial Multicomponent Monooxygenases: Phenol Hydroxylase and Toluene/o-Xylene Monooxygenase from *Pseudomonas* sp. OX1", Biochemistry 50(11), 1788-1798 (2011).
Van Schie, P , et al., "Biodegradation of Phenol: Mechanisms and Applications", Bioremediation Journal 4(1), 1-18 (2000).
Van Tegelen, L , et al., "Purification and cDNA Cloning of Isochorismate Synthase from Elicited Cell Cultures of Catharanthus roseus". Plant Physiology 119, 705-712 (1999).
Vardar, G , et al., "Alpha-Subunit Positions Methionine 180 and Glutamate 214 of Pseudomonas stutzeri OX1 Toluene-o-Xylene Monooxygenase Influence Catalysis", Journal of Bacteriology 187(4), 1511-1514 (2005).
Verhoef, S , et al., "Bioproduction of p-hydroxybenzoate from renewable feedstock by solvent-tolerant Pseudomonas putida S12", Journal of Biotechnology 132(1), 49-56 (2007).
Verhoef, S , et al., "Bioproduction of p-Hydroxystyrene from Glucose by the Solvent-Tolerant Bacterium Pseudomonas putida S12 in a Two-Phase Water-Decanol Fermentation", Applied and Environmental Microbiology 75 (4), 931-936 (2009).
Wang, J , et al., "Genetic engineering of *Escherichia coli* to enhance production of L-tryptophan", Applied Microbiology and Biotechnology 97, 7587-7596 (2013).
Weber, C , et al., "Biosynthesis of cis,cis-Muconic Acid and Its Aromatic Precursors, Catechol and Protocatechuic Acid, from Renewable Feedstocks by *Saccharomyces cerevisiae*", Applied and Environmental Microbiology 78(23), 8421-8430 (2012).
Wierckx, N , et al., "Engineering of Solvent-Tolerant Pseudomonas putida S12 for Bioproduction of Phenol from Glucose", Applied and Environmental Microbiology 71(12), 8221-8227 (2005).
Wierckx, N , et al., "Transcriptome Analysis of a Phenol-Producing Pseudomonas putida S12 Construct: Genetic and Physiological Basis for Improved Production", Journal of Bacteriology 190(8), 2822-2830 (2008).
Nildermuth, M , et al., "Correction: Corrigendum: Isochorismate synthase is required to synthesize salicylic acid for plant defence", Nature 417, 571 (2002).
Wildermuth, M , et al., "Isochorismate synthase is required to synthesize salicylic acid for plant defence", Nature 414, 562-565 (2001).
Wolfe, A, et al., "The Acetate Switch", Microbiology and Molecular Biology Reviews 69(1), 12-50 (2005).
Zhang, H , et al., "Engineering E. coli-E. coli cocultures for production of muconic acid from glycerol", Microbial Cell Factories 14(134), 1-10 (2015).
Zhang, H , et al., "Engineering *Escherichia coli* coculture systems for the production of biochemical products", Proceedings of the National Academy of Sciences of the United States of America 112(27), 8266-8271 (2015).
Thompson, B , et al., "Applying a 'Metabolic Funnel' for Phenol Production in *Escherichia coli*", Fermentation 7, 216, 1-10 (2021).
Thompson, B , et al., "Muconic Acid Production via Alternative Pathways and a Synthetic "Metabolic Funnel"", ACS Synth Biol 7, 565-575 and 12 pages of Supporting Information (Oct. 2017 (included in issue Feb. 2018)).
Ling, C, et al., "Muconic acid production from glucose and xylose in Pseudomonas putida via evolution and metabolic engineering", Nature Communications 13, 4925, 1-14 (2022).

* cited by examiner

| | |
|---|---|
| MA1 | 3DHS → PCA → Catechol → MA |
| MA2 | Tyr → Phenol → Catechol → MA |
| MA3 | Chorismate → Isochorismate → Salicylate → Phenol → Catechol → MA |
| MA4 | Chorismate → pHBA → Phenol → Catechol → MA |
| MA5 | Chorismate → pHBA → PCA → Catechol → MA |

| | $\Delta G_r'^o$(kJ/mol) | $Y_{X/S,max}$ | $Y_{P/S,max}$ | $Y_{P/S,max + growth}$ | EM Count |
|---|---|---|---|---|---|
| MA1 | -508.5 | 0.7086 | 0.8571 | 0.7945 | 468,715 |
| MA2 | -1007.6 | 0.7086 | 0.7013 | 0.6609 | 676,940 |
| MA3 | -1037.4 | 0.7086 | 0.7059 | 0.6777 | 506,231 |
| MA4 | -1037.4 | 0.7086 | 0.7059 | 0.6777 | 506,231 |
| MA5 | -1037.4 | 0.7086 | 0.7059 | 0.6777 | 506,231 |

FIGURES 3A-B

SYNTHETIC METABOLIC FUNNELING FOR BIOCHEMICAL PRODUCTION

RELATED APPLICATION

This application claims the benefit of priority of U.S. Provisional Application Ser. No. 62/533,997 filed on Jul. 18, 2017, which application is incorporated by reference herein.

SEQUENCE LISTING

The instant application contains a Sequence Listing which has been submitted electronically in ASCII format and is hereby incorporated by reference in its entirety. Said ASCII copy, created on Aug. 24, 2018, is named 17555_054WO1_SL.txt and is 35,267 bytes in size.

BACKGROUND

In recent years, cis,cis-muconic acid (hereafter also referred to as muconic acid, muconate, cis,cis-muconate, or MA) has continued to emerge as a diacid bioproduct of industrial interest, most notably due to its potential role as a precursor to adipic acid—a platform chemical used for the synthesis of various plastics and polymers (e.g., Nylon 6,6) (Adkins, et al., 2012. Frontiers in microbiology. 3, 313; Deng, et al., 2016. Biochem Eng J. 105, 16-26). Through metabolic pathway engineering, numerous studies have reported the engineering of microbes capable of producing MA as the focal product from renewable feedstocks (Curran et al., 2013. Metabolic engineering. 15; Draths, K. M., Frost, J. W., 1994. et al., Journal of the American Chemical Society. 116, 399-400; Lin, et al., 2014. Metabolic engineering. 23; Niu, et al., 2002. Biotechnology progress. 18, 201-11; Sengupta, et al., 2015. Applied and environmental microbiology. 81, 8037-8043; Sun, et al., 2013a. Applied and environmental microbiology. 79; Sun, et al., 2013b. Applied and environmental microbiology. 79, 4024-30; Weber, et al., 2012b. Applied and environmental microbiology. 78; Zhang, et al., 2015a. Microb Cell Fact. 14, 134; Zhang, et al., 2015b. Proceedings of the National Academy of Sciences of the United States of America. 112, 8266-71). Draths and Frost were first to report MA biosynthesis from glucose in *Escherichia coli*, following construction of a three-step pathway stemming from endogenous 3-dehydroshikimate (3DHS), a key intermediate in the shikimic acid pathway (Draths, K. M., Frost, J. W., 1994. et al., Journal of the American Chemical Society. 116, 399-400). Said pathway, which has since also been functionally re-constructed in *Saccharomyces cerevisiae* (Curran et al., 2013. Metabolic engineering. 15; Weber, et al., 2012a. Applied and environmental microbiology. 78, 8421-30), proceeds through the intermediates protocatechuate (PCA) and catechol via 3-DHS dehydratase, PCA decarboxylase, and catechol 1,2-dioxygenase (hereafter referred to as '3DHS-derived' pathway or pathway MA1). Achieving significant MA production via this pathway has typically required deletion of aroE (encoding shikimate dehydrogenase, an essential gene in minimal media). This mutation results in auxotrophies for the aromatic amino acids phenylalanine (Phe), tyrosine (Tyr), and tryptophan (Trp), as well as the growth essential vitamins p-aminobenzoate (pAB), p-hydroxybenzoate (pHBA), and 2,3-dihydroxybenzoate (2,3-DHB)—all of which are derived from chorismate as their last common precursor. Thus, although high MA titers and yields have been achieved by expressing this pathway in an *E. coli* ΔaroE background (2.4 g/L at 0.24 g/g-glucose, respectively, in shake flasks (Draths, K. M., Frost, J. W., 1994. et al., Journal of the American Chemical Society. 116, 399-400), and 36.8 g/L at 0.17 g/g-glucose in a fed-batch bioreactor (Niu, et al., 2002. Biotechnology progress. 18, 201-11)), doing so required each of the above six nutrients or shikimate to first be supplemented into the minimal salts media—an expensive and poorly scalable practice.

Accordingly, new compositions and methods for generating MA are needed. New compositions and methods are also generally needed for generating other biochemical products, including phenol and catechol.

SUMMARY

Described herein is a modular approach and methods for the microbial production of biochemical/biofuel products, such as phenol, catechol, and muconic acid, from renewable substrates using recombinant microorganisms. Phenol and catechol are aromatic building block chemicals, while muconic acid is used as precursor in plastics production. Biosynthesis of each of the three products was achieved by engineering and expressing a series of non-natural, modular enzyme pathways. In contrast to existing methods for the bioproduction of phenol, the methods described herein are not subject to equilibrium limitations or feedback inhibition of pathway enzymes. Meanwhile, in contrast to existing methods for the bioproduction of catechol and muconic acid, the methods described herein benefit from an improved thermodynamic driving force and strain engineering strategies with improved host compatibility and sustainability.

Accordingly, certain embodiments provide a method for preparing a biochemical product (e.g., phenol, catechol, or muconic acid, or a salt thereof). For example, such methods include contacting a recombinant host having two or more recombinant pathways with a fermentable carbon source and growing the recombinant cell for a time sufficient to synthesize the product. In certain embodiments, each recombinant pathway: 1) is capable of producing the same final biochemical product; 2) comprises (or consists of) at least one gene encoding a polypeptide; 3) is derived from a different endogenous metabolite as its immediate precursor; and 4) converges to the same final product or the same intermediate metabolite.

BRIEF DESCRIPTION OF THE FIGURES

FIG. 3A) Conversion of phenol (squares) to catechol (circles) by *E. coli* BW25113 pPh cultures. FIG. 3B) Conversion of phenol (squares) to catechol (circles) or muconic acid (diamonds) by *E. coli* BW25113 pPh-CatA cultures. Error bars represent one standard deviation from triplicate experiments.

FIG. 5A. Engineering a 'synthetic funnel' for MA production via the simultaneous co-expression of two distinct biosynthesis pathways, stemming from two different precursors (3DHS and chorismate), both derived from the shikimic acid pathway. Also shown are the native mechanisms by which different aromatic degradation pathways also 'funnel' various substrates and intermediates towards MA, in this case for further catabolism. Black bold dashed arrows represent multiple enzyme reactions native to *E. coli*; solid black arrows represent individual enzymes steps associated with the pathways engineered in this study; Gray solid and dashed arrows represent individual and multi-step enzyme processes associated with the aerobic degradation of aromatic chemicals. PCA, protocatechuate; pHBA, p-hydroxybenzoate; AAA, aromatic amino acids; TCA, tricarboxylic acid cycle. FIG. 5B. Engineering a 'synthetic funnel' for MA production via the simultaneous co-expression of two distinct biosynthesis pathways, namely MA1 (composed of steps A, B, C) and MA5 (composed of steps D, E, B, C). The combined, 'funneling' pathway MAF (composed of steps A, B, C, D, E) produces MA by simultaneously drawing from two different precursors (3DHS and chorismate), both derived from the shikimic acid pathway. Black arrows represent native *E. coli* enzymatic steps; gray arrows represent heterologous steps; dotted arrows represent multiple enzymatic steps. $\Delta_r G'^{\circ}$ is the change in Gibbs free energy due to reaction as determined using the online tool eQuilibrator (http://equilibrator.weizmann.ac.il) at a reference state of 25° C., pH 7, and ionic strength of 0.1 M. "A": 3-dehydroshikimate dehydratase, "B": protocatechuate decarboxylase, "C": catechol 1,2-dioxygenase, "D": chorismate pyruvate lyase, "E": p-hydroxybenzoate hydroxylase.

DETAILED DESCRIPTION

Figure 1:
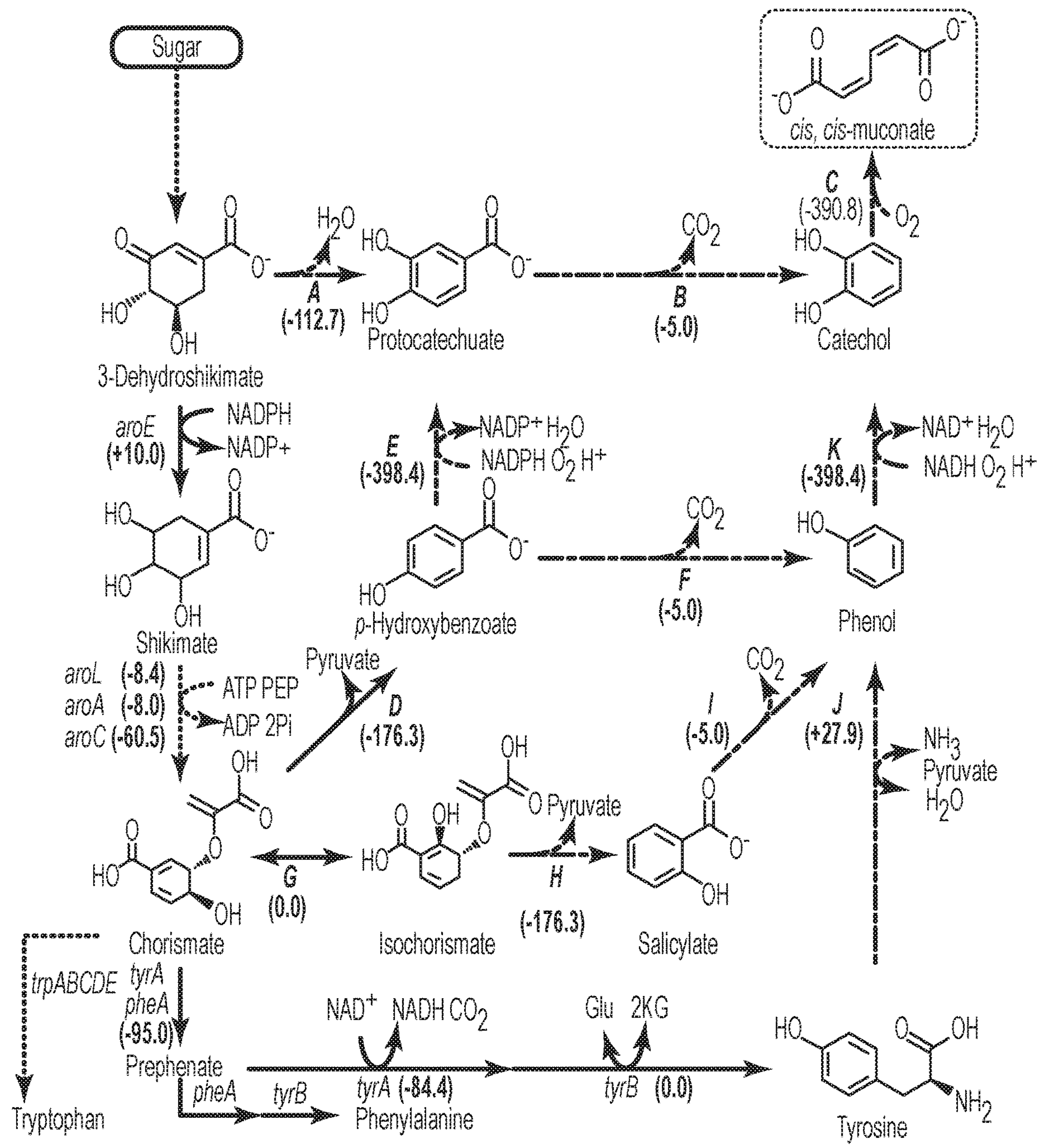
FIG. 1. Five non-natural pathways engineered for muconic acid biosynthesis from glucose. Black arrows represent native *E. coli* enzymatic steps; gray arrows represent heterologous steps; dotted arrows represent multiple enzymatic steps. $\Delta_r G'^{o}$ is the change in Gibbs free energy due to reaction as determined using the online tool eQuilibrator (http://equilibrator.weizmann.ac.il) at a reference state of 25° C., pH 7, and ionic strength of 0.1 M. A: 3-dehydroshikimate dehydratase, B: protocatechuate decarboxylase, C: catechol 1,2-dioxygenase, D: chorismate pyruvate lyase, E: p-hydroxybenzoate hydroxylase, F: p-hydroxybenzoate decarboxylase, G: isochorismate synthase, H: isochorismate pyruvate lyase, I: salicylate decarboxylase, J: tyrosine phenol lyase, K: phenol hydroxylase.

By rational re-engineering of their metabolism, microorganisms can be engineered to convert biomass-derived feedstocks to specific focal products of interest, including chemicals and fuels traditionally derived from petroleum. In such cases, metabolic engineering can be applied not only to improve the function of naturally-occurring pathways, but also for the de novo creation of synthetic pathways to enable the novel biosynthesis of non-inherent and even non-natural products. Traditional applications of metabolic pathway engineering focus on expressing in a recombinant host a single pathway that has been designed and engineered for the biosynthesis of a specific and single focal product of interest. In certain cases, however, there are more than one possible enzyme pathways that have been engineered, proposed, or hypothesized to enable biosynthesis of the same product molecule. Common examples of this include, but are not limited to, ethanol, 3-hydroxypropionate, phenol, catechol, muconic acid, and isoprenoids. Typically, different pathways offer their own unique and advantages as well as disadvantages relative to the other distinct pathway options. Examples include, but are not limited to: differences in product titer and/or yield; differences in host toxicity owing to the involvement of inhibitory genes, proteins, or intermediate metabolites; differences in host fitness owing to competition for different growth essential precursor metabolites; and, differences in thermodynamic driving forces. In light of the foregoing, it would be an advancement to provide a method by which to balance the relative trade-offs between different alternative metabolic pathways engineered for the biosynthesis of the same product.

Accordingly, as described herein, certain embodiments comprise an in vivo method for the production of a biochemical via a recombinant host cell by simultaneously co-expressing two or more enzyme pathways each engineered for the biosynthesis of the same final product (see, Thompson et al., *ACS Synth. Biol.* 2018, 7(2):565-575 and supporting information, which are incorporated by reference herein in their entirety). In this way, precursor metabolites are more effectively and extensively funneled towards the final product of interest. Moreover, the relative advantages and disadvantages of different pathway alternatives can be effectively balanced to optimize inherent trade-offs including, for example, host fitness versus pathway flux and yield.

Certain embodiments also comprise specific methods for the in vivo production of phenol, catechol, and muconic acid via the aforementioned approach. Specifically, a series of novel, modular enzyme pathways and microorganisms have been engineered to produce each of phenol, catechol, and muconic acid as focal products from renewable resources (e.g., from a fermentable substrate such as glucose). All three products represent useful molecular building blocks for the production of numerous fine and commodity chemicals, as well as plastic materials. Currently, all three products are derived from non-renewable petroleum feedstocks. The proposed methods and microorganisms represent an advance over previous methods and compositions, specifically by addressing key thermodynamic, enzymatic, and/or resource limitations associated with the conventional bioproduction of said compounds. For these three compounds, co-expression of multiple pathways in the same recombinant microorganism has been shown to promote higher product titers and yields than achievable by expressing any single pathway alone. Additionally, the methods described herein are further suitable for improving the production of other bioproducts of interest from renewable and sustainable resources.

Exemplary Methods According to One or More Embodiments

One embodiment provides a method for preparing a biochemical product, the method comprising:

i) contacting a recombinant host cell with a fermentable carbon source, said recombinant host comprising two or more recombinant pathways, wherein:
   a) each pathway is capable of producing the same final biochemical product;
   b) each pathway consists of or comprises at least one gene encoding a polypeptide (e.g., a recombinant gene);
   c) each pathway is derived from a different endogenous metabolite as its immediate precursor; and
   d) each pathway converges to the same final product;

and ii) growing said recombinant cell for a time sufficient to synthesize the final biochemical product.

One embodiment provides a method for preparing a biochemical product, the method comprising:

i) contacting a recombinant host cell with a fermentable carbon source, said recombinant host comprising two or more recombinant pathways, wherein:
   a) each pathway is capable of producing the same final biochemical product;
   b) each pathway consists of or comprises at least one gene encoding a polypeptide;
   c) each pathway is derived from a different endogenous metabolite as its immediate precursor;
   d) each pathway converges to the same intermediate metabolite; and
   e) each pathway continues to the same final product;

and ii) growing said recombinant cell for a time sufficient to synthesize the product.

One embodiment provides a method for preparing a biochemical product, the method comprising:

i) contacting a recombinant host cell with a fermentable carbon source, wherein the recombinant host comprises two or more recombinant pathways, and wherein:
   a) each pathway is capable of producing the same final biochemical product;
   b) each pathway consists of or comprises at least one gene encoding a polypeptide;
   c) each pathway is derived from the same endogenous metabolite as its immediate precursor;
   d) each pathway proceeds via different intermediate metabolites;
   e) each pathway consists of or comprises at least one gene encoding polypeptides with differing activities; and
   f) each pathway converges to the same final product; and ii) growing said recombinant cell for a time sufficient to synthesize the product.

One embodiment provides a method for preparing a biochemical product, the method comprising:

i) contacting a recombinant host cell with a fermentable carbon source, wherein the recombinant host comprises two or more recombinant pathways, and wherein:
   a) each pathway is capable of producing the same final biochemical product;
   b) each pathway consists of or comprises at least one gene encoding a polypeptide;
   c) each pathway is derived from the same endogenous metabolite as its immediate precursor;
   d) each pathway proceeds via different intermediate metabolites;
   e) each pathway consists of or comprises at least one gene encoding polypeptides with differing activities;
   f) each pathway converges to the same intermediate metabolite; and
   g) each pathway continues to the same final product; and ii) growing said recombinant cell for a time sufficient to synthesize the product.

One embodiment provides a method for the production of phenol, the method comprising:

i) contacting a recombinant host cell with a fermentable carbon source, said recombinant host comprising:
   a) at least one gene encoding a polypeptide having chorismate lyase activity; and
   b) at least one gene encoding a polypeptide having p-hydroxybenzoate decarboxylase activity;

and ii) growing said recombinant cell for a time sufficient to produce phenol.

One embodiment provides a method for the production of phenol, the method comprising:

i) contacting a recombinant host cell with a fermentable carbon source, said recombinant host comprising:
   a) at least one gene encoding a polypeptide having isochorismate synthase activity;
   b) at least one gene encoding a polypeptide having isochorismate pyruvate lyase activity;
   c) at least one gene encoding a polypeptide having salicylate decarboxylase activity; and
   d) at least one gene encoding a polypeptide having tyrosine phenol lyase activity;

and ii) growing said recombinant cell for a time sufficient to produce phenol.

One embodiment provides a method for the production of phenol, the method comprising:

i) contacting a recombinant host cell with a fermentable carbon source, said recombinant host comprising:
   a) at least one gene encoding a polypeptide having chorismate lyase activity;
   b) at least one gene encoding a polypeptide having p-hydroxybenzoate decarboxylase activity; and
   c) at least one gene encoding a polypeptide having tyrosine phenol lyase activity;

and ii) growing said recombinant cell for a time sufficient to produce phenol.

One embodiment provides a method for the production of phenol, the method comprising:

i) contacting a recombinant host cell with a fermentable carbon source, said recombinant host comprising:
   a) at least one gene encoding a polypeptide having isochorismate synthase activity;
   b) at least one gene encoding a polypeptide having isochorismate pyruvate lyase activity;
   c) at least one gene encoding a polypeptide having salicylate decarboxylase activity;
   d) at least one gene encoding a polypeptide having chorismate lyase activity; and
   e) at least one gene encoding a polypeptide having p-hydroxybenzoate decarboxylase activity;

and ii) growing said recombinant cell for a time sufficient to produce phenol.

One embodiment provides a method for the production of phenol, the method comprising:

i) contacting a recombinant host cell with a fermentable carbon source, said recombinant host comprising:
 a) at least one gene encoding a polypeptide having isochorismate synthase activity;
 b) at least one gene encoding a polypeptide having isochorismate pyruvate lyase activity;
 c) at least one gene encoding a polypeptide having salicylate decarboxylase activity;
 d) at least one gene encoding a polypeptide having chorismate lyase activity;
 e) at least one gene encoding a polypeptide having p-hydroxybenzoate decarboxylase activity; and
 f) at least one gene encoding a polypeptide having tyrosine phenol lyase activity;

and ii) growing said recombinant cell for a time sufficient to produce phenol.

One embodiment provides a method for the production of catechol, the method comprising:

i) contacting a recombinant host cell with a fermentable carbon source, said recombinant host comprising:
 a) at least one gene encoding a polypeptide having chorismate lyase activity;
 b) at least one gene encoding a polypeptide having p-hydroxybenzoate decarboxylase activity; and
 c) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having tyrosine phenol lyase activity; and
 b) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having chorismate lyase activity;
 b) at least one gene encoding a polypeptide having p-hydroxybenzoate hydroxylase activity; and
 c) at least one gene encoding a polypeptide having protocatechuate decarboxylase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having isochorismate synthase activity;
 b) at least one gene encoding a polypeptide having isochorismate pyruvate lyase activity;
 c) at least one gene encoding a polypeptide having salicylate decarboxylase activity;
 d) at least one gene encoding a polypeptide having tyrosine phenol lyase activity; and
 e) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having chorismate lyase activity;
 b) at least one gene encoding a polypeptide having p-hydroxybenzoate decarboxylase activity;
 c) at least one gene encoding a polypeptide having tyrosine phenol lyase activity; and
 d) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having isochorismate synthase activity;
 b) at least one gene encoding a polypeptide having isochorismate pyruvate lyase activity;
 c) at least one gene encoding a polypeptide having salicylate decarboxylase activity;
 d) at least one gene encoding a polypeptide having chorismate lyase activity;
 e) at least one gene encoding a polypeptide having p-hydroxybenzoate decarboxylase activity; and
 f) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having chorismate lyase activity;
 b) at least one gene encoding a polypeptide having p-hydroxybenzoate hydroxylase activity;
 c) at least one gene encoding a polypeptide having protocatechuate decarboxylase activity;
 d) at least one gene encoding a polypeptide having p-hydroxybenzoate decarboxylase activity; and
 e) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:
 a) at least one gene encoding a polypeptide having chorismate lyase activity;
 b) at least one gene encoding a polypeptide having p-hydroxybenzoate hydroxylase activity;
 c) at least one gene encoding a polypeptide having protocatechuate decarboxylase activity;
 d) at least one gene encoding a polypeptide having isochorismate synthase activity;
 e) at least one gene encoding a polypeptide having isochorismate pyruvate lyase activity;
 f) at least one gene encoding a polypeptide having salicylate decarboxylase activity; and g) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having chorismate lyase activity;

b) at least one gene encoding a polypeptide having p-hydroxybenzoate hydroxylase activity;

c) at least one gene encoding a polypeptide having protocatechuate decarboxylase activity;

d) at least one gene encoding a polypeptide having tyrosine phenol lyase activity; and e) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having chorismate lyase activity;

c) at least one gene encoding a polypeptide having p-hydroxybenzoate hydroxylase activity; and d) at least one gene encoding a polypeptide having protocatechuate decarboxylase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having protocatechuate decarboxylase activity;

c) at least one gene encoding a polypeptide having chorismate lyase activity;

d) at least one gene encoding a polypeptide having p-hydroxybenzoate decarboxylase activity; and e) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having protocatechuate decarboxylase activity;

c) at least one gene encoding a polypeptide having isochorismate synthase activity;

d) at least one gene encoding a polypeptide having isochorismate pyruvate lyase activity;

e) at least one gene encoding a polypeptide having salicylate decarboxylase activity; and f) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having protocatechuate decarboxylase activity;

c) at least one gene encoding a polypeptide having tyrosine phenol lyase activity; and d) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having chorismate lyase activity;

c) at least one gene encoding a polypeptide having p-hydroxybenzoate hydroxylase activity;

d) at least one gene encoding a polypeptide having protocatechuate decarboxylase activity;

e) at least one gene encoding a polypeptide having tyrosine phenol lyase activity; and f) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having chorismate lyase activity;

c) at least one gene encoding a polypeptide having p-hydroxybenzoate hydroxylase activity;

d) at least one gene encoding a polypeptide having protocatechuate decarboxylase activity;

e) at least one gene encoding a polypeptide having isochorismate synthase activity;

f) at least one gene encoding a polypeptide having isochorismate pyruvate lyase activity;

g) at least one gene encoding a polypeptide having salicylate decarboxylase activity; and h) at least one gene encoding a polypeptide having phenol 2-monooxygenase activity;

and ii) growing said recombinant cell for a time sufficient to produce catechol.

One embodiment provides a method for the production of catechol, the method comprising:

i) contacting a recombinant host cell with a fermentable carbon source, said recombinant host comprising:

a) at least one gene encoding a polypeptide having 3-dehydroshikimate dehydratase activity;

b) at least one gene encoding a polypeptide having chorismate lyase activity;

c) at least one gene encoding a polypeptide having p-hydroxybenzoate hydroxylase activity;

d) at least one gene encoding a polypeptide having protocatechuate decarboxylase activity;
e) at least one gene encoding a polypeptide having p-hydroxybenzoate decarboxylase activity; and
f) at least one gene encoding a polypeptide having phenol 2-monooxygenase activity;

and ii) growing said recombinant cell for a time sufficient to produce catechol.

One embodiment provides a method for the production of muconic acid, or a salt thereof, the method comprising:

i) contacting a recombinant host cell with a fermentable carbon source, said recombinant host comprising:
a) at least one gene encoding a polypeptide having chorismate lyase activity;
b) at least one gene encoding a polypeptide having p-hydroxybenzoate decarboxylase activity;
c) at least one gene encoding a polypeptide having phenol 2-monooxygenase activity; and
d) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having tyrosine phenol lyase activity;
b) at least one gene encoding a polypeptide having phenol 2-monooxygenase activity; and
c) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having chorismate lyase activity;
b) at least one gene encoding a polypeptide having p-hydroxybenzoate hydroxylase activity;
c) at least one gene encoding a polypeptide having protocatechuate decarboxylase activity; and
d) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having isochorismate synthase activity;
b) at least one gene encoding a polypeptide having isochorismate pyruvate lyase activity;
c) at least one gene encoding a polypeptide having salicylate decarboxylase activity;
d) at least one gene encoding a polypeptide having tyrosine phenol lyase activity;
e) at least one gene encoding a polypeptide having phenol 2-monooxygenase activity; and
f) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having chorismate lyase activity;
b) at least one gene encoding a polypeptide having p-hydroxybenzoate decarboxylase activity;
c) at least one gene encoding a polypeptide having tyrosine phenol lyase activity;
d) at least one gene encoding a polypeptide having phenol 2-monooxygenase activity; and
e) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having isochorismate synthase activity;
b) at least one gene encoding a polypeptide having isochorismate pyruvate lyase activity;
c) at least one gene encoding a polypeptide having salicylate decarboxylase activity;
d) at least one gene encoding a polypeptide having chorismate lyase activity;
e) at least one gene encoding a polypeptide having p-hydroxybenzoate decarboxylase activity;
f) at least one gene encoding a polypeptide having phenol 2-monooxygenase activity; and
g) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having chorismate lyase activity;
b) at least one gene encoding a polypeptide having p-hydroxybenzoate hydroxylase activity;
c) at least one gene encoding a polypeptide having protocatechuate decarboxylase activity;
d) at least one gene encoding a polypeptide having p-hydroxybenzoate decarboxylase activity;
e) at least one gene encoding a polypeptide having phenol 2-monooxygenase activity; and
f) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having chorismate lyase activity;
b) at least one gene encoding a polypeptide having p-hydroxybenzoate hydroxylase activity;
c) at least one gene encoding a polypeptide having protocatechuate decarboxylase activity;
d) at least one gene encoding a polypeptide having isochorismate synthase activity;

e) at least one gene encoding a polypeptide having isochorismate pyruvate lyase activity;
f) at least one gene encoding a polypeptide having salicylate decarboxylase activity;
g) at least one gene encoding a polypeptide having phenol 2-monooxygenase activity; and
h) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having chorismate lyase activity;
b) at least one gene encoding a polypeptide having p-hydroxybenzoate hydroxylase activity;
c) at least one gene encoding a polypeptide having protocatechuate decarboxylase activity;
d) at least one gene encoding a polypeptide having tyrosine phenol lyase activity;
e) at least one gene encoding a polypeptide having phenol 2-monooxygenase activity; and
f) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having chorismate lyase activity;
c) at least one gene encoding a polypeptide having p-hydroxybenzoate hydroxylase activity;
d) at least one gene encoding a polypeptide having protocatechuate decarboxylase activity; and
e) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having protocatechuate decarboxylase activity;
c) at least one gene encoding a polypeptide having chorismate lyase activity;
d) at least one gene encoding a polypeptide having p-hydroxybenzoate decarboxylase activity;
e) at least one gene encoding a polypeptide having phenol 2-monooxygenase activity; and
f) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having protocatechuate decarboxylase activity;
c) at least one gene encoding a polypeptide having isochorismate synthase activity;
d) at least one gene encoding a polypeptide having isochorismate pyruvate lyase activity;
e) at least one gene encoding a polypeptide having salicylate decarboxylase activity;
f) at least one gene encoding a polypeptide having phenol 2-monooxygenase activity; and
g) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having protocatechuate decarboxylase activity;
c) at least one gene encoding a polypeptide having tyrosine phenol lyase activity;
d) at least one gene encoding a polypeptide having phenol 2-monooxygenase activity; and
e) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having chorismate lyase activity;
c) at least one gene encoding a polypeptide having p-hydroxybenzoate hydroxylase activity;
d) at least one gene encoding a polypeptide having protocatechuate decarboxylase activity;
e) at least one gene encoding a polypeptide having tyrosine phenol lyase activity;
f) at least one gene encoding a polypeptide having phenol 2-monooxygenase activity; and
g) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having chorismate lyase activity;
c) at least one gene encoding a polypeptide having p-hydroxybenzoate hydroxylase activity;
d) at least one gene encoding a polypeptide having protocatechuate decarboxylase activity;
e) at least one gene encoding a polypeptide having isochorismate synthase activity;

f) at least one gene encoding a polypeptide having isochorismate pyruvate lyase activity;
g) at least one gene encoding a polypeptide having salicylate decarboxylase activity;
h) at least one gene encoding a polypeptide having phenol 2-monooxygenase activity; and
i) at least one gene encoding a polypeptide having 1,2-catechol dioxygenase activity;

and ii) growing said recombinant cell for a time sufficient to produce muconic acid, or a salt thereof.

One embodiment provides a method for the production of muconic acid, or a salt thereof, the method comprising:

i) contacting a recombinant host cell with a fermentable carbon source, said recombinant host comprising:
a) at least one gene encoding a polypeptide having 3-dehydroshikimate dehydratase activity;
b) at least one gene encoding a polypeptide having chorismate lyase activity;
c) at least one gene encoding a polypeptide having p-hydroxybenzoate hydroxylase activity;
d) at least one gene encoding a polypeptide having protocatechuate decarboxylase activity;
e) at least one gene encoding a polypeptide having p-hydroxybenzoate decarboxylase activity;
f) at least one gene encoding a polypeptide having phenol 2-monooxygenase activity; and
g) at least one gene encoding a polypeptide having 1,2-catechol dioxygenase activity;

and ii) growing said recombinant cell for a time sufficient to produce muconic acid, or a salt thereof.

One embodiment provides a method for the production of phenol, catechol or muconic acid, or a salt thereof, the method comprising:

i) contacting a recombinant host cell with a fermentable carbon source, said recombinant host comprising:
a) at least one gene described herein or a combination of genes as described herein (e.g., as described in the Figures or Tables (e.g., Table 1));

and ii) growing said recombinant cell for a time sufficient to produce phenol, catechol or muconic acid, or a salt thereof.

In certain embodiments, the recombinant host further comprises at least one gene encoding a polypeptide having chorismate mutase/prephenate dehydrogenase activity.

In certain embodiments, the methods further comprise amplifying genomic DNA for the gene of interest (e.g., via PCR), cloning the amplified genetic material into an expression vector, and transforming the host cell to express the encoded protein.

In one embodiment, the biochemical product is phenol, catechol or muconic acid, or a salt thereof.

Substrate/Carbon Source

The term "fermentable carbon substrate" or "fermentable carbon source" refers to a carbon source capable of being metabolized by the recombinant host cells described herein, in either its purified or unpurified form. For example, carbon sources may be selected from the group consisting of monosaccharides, oligosaccharides, polysaccharides, fats, lipids, aromatic monomers and/or oligomers, organic acids, glycerol, and one-carbon substrates, or mixtures thereof. In one embodiment, the fermentable carbon source is selected from the group consisting of monosaccharides, oligosaccharides, polysaccharides, glycerol, carbon dioxide, methanol, methane, formaldehyde, formate, amino acids and carbon-containing amines.

In one embodiment, the fermentable carbon source is glucose, xylose, or glycerol.

In one embodiment, the fermentable carbon source is a mixture of lignin-derived aromatic monomers and/or oligomers.

In one embodiment, the fermentable carbon source is biomass hydrolysate.

Host Cells

The production organisms (e.g., a recombinant host cell) may include any organism capable of expressing the genes required for the production of a biochemical product of interest, such as phenol, catechol or muconic acid (e.g., microorganism or plant). For example, the production organism may be a microorganism or plant. Microorganisms include, but are not limited to enteric bacteria (*Escherichia* and *Salmonella*, for example) as well as *Bacillus, Sphingomonas, Clostridium, Acinetobacter, Actinomycetes* such as *Streptomyces, Corynebacterium*; methanotrophs such as *Methylosinus, Methylomonas, Rhodococcus* and *Pseudomonas*; cyanobacteria, such as *Synechococcus* and *Synechocystis*; yeasts, such as *Saccharomyces, Zygosaccharomyces, Kluyveromyces, Candida, Hansenula, Debaryomyces, Mucor, Pichia, Yarrowia*, and *Torulopsis*; filamentous fungi, such as *Aspergillus* and *Arthrobotrys*; and algae, such as *Chlamydomonas*, for example.

Accordingly, in one embodiment, the recombinant host cell is selected from the group consisting of bacteria, yeast, filamentous fungi, cyanobacteria, algae, and plant cells.

In one embodiment, the recombinant host cell is selected from the group consisting of *Escherichia, Salmonella, Bacillus, Acinetobacter, Streptomyces, Sphingomonas, Clostridium, Corynebacterium, Methylosinus, Methylomonas, Rhodococcus, Pseudomonas, Rhodobacter, Synechocystis, Saccharomyces, Klebsiella, Zygosaccharomyces, Kluyveromyces, Candida, Hansenula, Debaryomyces, Mucor, Pichia, Yarrowia, Torulopsis, Aspergillus, Arthrobotrys, Brevibacterium, Microbacterium, Arthrobacter, Citrobacter, Chlamydomonas*, and *Zymomonas*.

In certain embodiments, the recombinant host cell is *Escherichia coli*.

In certain embodiments, the recombinant host cell is *E. coli* NST74, *E. coli* NST74 ΔpheA, *E. coli* NST74 ΔpheA ΔpykA ΔpykF, or *E. coli* NST74 ΔpheA ΔpykA ΔpykF Δcrr.

In certain embodiments, the recombinant host cell is a cell as described herein, such as in the Examples, Tables, or Figures.

Microbial expression systems and expression vectors containing regulatory sequences that direct high-level expression of foreign proteins and over-expression of native proteins are well known to those skilled in the art (see, e.g., the Example). Any of these could be used for recombinant expression of at least one gene described herein for the production of a biochemical product, including those as described herein (e.g., phenol, catechol or muconic acid). Such an expression vector(s) comprising the gene(s) of interest could then be introduced into appropriate microorganisms via transformation to allow for expression of the enzyme(s).

Genes

Described herein are methods for the microbial production of biochemical products, such as phenol, catechol, and muconic acid, from renewable substrates using recombinant host cells. Specifically, embodiments described herein may involve the incorporation of genes encoding polypeptides having isochorismate synthase activity, isochorismate pyruvate lyase activity, salicylate decarboxylase activity, phenol 2-monooxygenase activity, catechol-1,2-dioxygenase activity, tyrosine phenol lyase activity, chorismate lyase activity, chorismate pyruvate lyase activity, p-hydroxybenzoate decarboxylase activity, p-hydroxybenzoate hydroxylase activity, protocatechuate decarboxylase activity, and/or 3-dehydroshikimate dehydratase activity into a single host organism and the use of those organisms to convert renewable resources such as glucose, for example, to phenol, catechol and muconic acid. As discussed below, genes encoding enzymes having such activities are known in the art. In certain embodiments, a gene encoding a polypeptide having the specific activity described below is derived from an organism described herein.

Genes encoding a polypeptide having isochorismate synthase activity are known in the art and several have been sequenced from both microbial and plant origin. The sequence of isochorismate synthase activity encoding genes are available (for example, entC, menF, pchA, ICS1; see GenBank Gene ID: 945511, 946712, 881821, and 843810). Accordingly, in certain embodiments, the gene encoding a polypeptide having isochorismate synthase activity is entC, menF, pchA or ICS1. In certain embodiments, the gene encoding a polypeptide having isochorismate synthase activity is entC. In certain embodiments, the entC gene has the following sequence:

```
                                       (SEQ ID NO: 1)
ATGGATACGTCACTGGCTGAGGAAGTACAGCAGACCATGGCAACACTTGC

GCCCAATCGCTTTTTCTTTATGTCGCCGTACCGCAGTTTTACGACGTCAG

GATGTTTCGCCCGCTTCGATGAACCGGCTGTGAACGGGGATTCGCCCGAC

AGTCCCTTCCAGCAAAAACTCGCCGCGCTGTTTGCCGATGCCAAAGCGCA

GGGCATCAAAAATCCGGTGATGGTCGGGGCGATTCCCTTCGATCCACGTC

AGCCTTCGTCGCTGTATATTCCTGAATCCTGGCAGTCGTTCTCCCGTCAG

GAAAAACAAGCTTCCGCACGCCGTTTCACCCGCAGCCAGTCGCTGAATGT

GGTGGAACGCCAGGCAATTCCGGAGCAAACCACGTTTGAACAGATGGTTG

CCCGCGCCGCCGCACTTACCGCCACGCCGCAGGTCGACAAAGTGGTGTTG

TCACGGTTGATTGATATCACCACTGACGCCGCCATTGATAGTGGCGTATT

GCTGGAACGGTTGATTGCGCAAAACCCGGTTAGTTACAACTTCCATGTTC

CGCTGGCTGATGGTGGCGTCCTGCTGGGGGCCAGCCCGGAACTGCTGCTA

CGTAAAGACGGCGAGCGTTTTAGCTCCATTCCGTTAGCCGGTTCCGCGCG

TCGTCAGCCGGATGAAGTGCTCGATCGCGAAGCAGGTAATCGTCTGCTGG

CGTCAGAAAAAGATCGCCATGAACATGAACTGGTGACTCAGGCGATGAAA

GAGGTACTGCGCGAACGCAGTAGTGAGTTACACGTTCCTTCTTCTCCACA

GCTGATCACCACGCCGACGCTGTGGCATCTCGCAACTCCCTTTGAAGGTA

AAGCGAATTCGCAAGAAAACGCACTGACTCTGGCCTGTCTGCTGCATCCG

ACCCCCGCGCTGAGCGGTTTCCCGCATCAGGCCGCGACCCAGGTTATTGC

TGAACTGGAACCGTTCGACCGCGAACTGTTTGGCGGCATTGTGGGTTGGT

GTGACAGCGAAGGTAACGGCGAATGGGTGGTGACCATCCGCTGCGCGAAG

CTGCGGGAAAATCAGGTGCGTCTGTTTGCCGGAGCGGGGATTGTGCCTGC

GTCGTCACCGTTGGGTGAGTGGCGCGAAACAGGCGTCAAACTTTCTACCA

TGTTGAACGTTTTTGGATTGCATTAA.
```

Accordingly, in certain embodiments, the at least one gene encoding a polypeptide having isochorismate synthase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1.

Genes encoding polypeptides having isochorismate pyruvate lyase activity are known in the art and several have been sequenced from microbial origin. The sequence of isochorismate pyruvate lyase encoding genes are available (for example, pchB; see GenBank Gene ID: 881846). Accordingly, in certain embodiments, the gene encoding a polypeptide having isochorismate pyruvate lyase activity is pchB. In certain embodiments, the pchB gene has the following sequence: ATGAAAACTCCCGAA-
GACTGCACCGGCCTGGCGGACATCCGCGAGGC-
CATCGACCG GATCGACCTGGATATCGTCCAGGC-
CCTCGGCCGCCGCATGGACTACGTCAAGGCGG
CGTCGCGCTTCAAGGCCAGCGAGGCGGCGAT-
TCCGGCGCCCGAGCGGGTCGCCGCG ATGCTC-
CCCGAGCGCGCCCGCTGGGCCGAGGAAAACG-
GACTCGACGCGCCCTTCGT CGAGGGACTGTTC-
GCGCAGATCATCCACTGGTACATCGCCGAGCAGAT-
CAAGTACT GGCGCCAGACACGGGGTGCCGCATGA (SEQ ID NO:2). Accordingly, in certain embodiments, the at least one gene encoding a polypeptide having isochorismate pyruvate lyase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:2.

Genes encoding polypeptides having salicylate decarboxylase activity are known in the art and to date only one has been sequenced from microbial origin. The sequence of salicylate decarboxylase encoding genes are available (for example, SDC; see DDBJ ID: DM040453). Accordingly, in certain embodiments, the gene encoding a polypeptide having salicylate decarboxylase activity is SDC. In certain embodiments, the SDC gene has the following sequence:
ATGCGTGGTAAAGTTAGCCTGGAAGAAGCATTT-
GAACTGCCGAAATTTGCAGCACA GACCAAAGA-
AAAAGCCGAACTGTATATTGCACCGAATAATCGC-
GATCGCTATTTTG AAGAAATTCTGAATCCGTG-
TGGTAATCGTCTGGAACTGAGCAATAAACATGGT-
ATT GGCTATACCATCTATAGCATCTATTCACCGG-
GTCCGCAGGGTTGGACCGAACGTGCA GAATGT-
GAAGAATATGCACGTGAATGCAACGATTATATCA-
GCGGTGAAATTGCCAA TCACAAAGATCGTATGGG-
TGCATTTGCAGCCCTGAGCATGCATGATCCGAA-
ACAGG CAAGCGAAGAACTGACCCGTTGTGTTAA-
AGAACTGGGTTTTCTGGGTGCACTGGTTA ATGATG-
TTCAGCATGCAGGTCCGGAAGGTGAAACCCATA-
TCTTTTATGATCAGCCGG AATGGGATATCTTTTG-
GCAGACCTGTGTTGATCTGGATGTTCCGTTTTATCT-
GCATCC GGAACCGCCTTTTGGTAGCTATCTGCGT-
AATCAGTATGAAGGTCGCAAATATCTGAT TGGTCC-
GCCTGTTAGCTTTGCAAATGGTGTTAGCCTGCATG-
TTCTGGGTATGATTGTT AATGGTGTGTTTGATCG-
TTTTCCGAAACTGAAAGTTATTCTGGGTCATCTG-
GGTGAA CATATTCCGGGTGATTTTTGGCGTATT-
GAACATTGGTTTGAACACTGTAGCCGTCCG CTGG-
CAAAAAGCCGTGGTGATGTTTTTGCAGAAAAACC-
GCTGCTGCATTATTTTCGC AATAACATTTGGCTGAC-
CACGAGCGGCAATTTTAGCACCGAAACCCTGAAAT-
TTTGC GTTGAACATGTTGGTGCAGAACGCAT-
TCTGTTTAGCGTTGATAGCCCGTATGAACAT ATCG-
ATGTTGGTTGTGGTTGGTATGATGATAATGCCAA-
AGCAATTATGGAAGCCGTT GTGGTGAAAAAGCC-
TATAAAGATATTGGTCGCGACAACGCGAAAAAAC- TGTTTAA ACTGGGCAAATTCTATGACAGCGAA-
GCCTAA (SEQ ID NO:3). Accordingly, in certain embodiments, the at least one gene encoding a polypeptide having salicylate decarboxylase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:3.

Genes encoding polypeptides having phenol 2-monooxygenase activity are known in the art and have been sequenced. The sequence of phenol 2-monooxygenase encoding genes are available (for example, operon dmpLMNOP, loci GI: 170525 and operon phKLMNOP; see GenBankAccession: L04488.1, M60276.1). Accordingly, in certain embodiments, the gene encoding a polypeptide having phenol 2-monooxygenase activity is operon dmpLMNOP, loci GI: 170525 or operon phKLMNOP, loci GI: 151449. In certain embodiments, the genes encoding a polypeptide having phenol 2-monooxygenase activity is operon phKLMNOP. In certain embodiments, the phKLMNOP operon has the following sequence: GAGCTCGTGCTGCCT-
CACGAGGCCTTCGAGATTTTCTGCAAACATAAC-
AAAGTCGTC CACATGGACTCCAACATAATCCG-
CAAAATTGACGAAGACATGGTCAAGTGGCGGTT
CGGAGAGCATGGCAAGCGCTACTGAGCAAGACG-
CATCGGCATACAGTATCACAACA ACAACACG-
GTAAGGTTGATATGAGTATTGAAATCAAGACCAAT-
TCGGTGGAACCTA TCCGCCATACTTATGGCCA-
CATCGCCCGTCGCTTCGGTGATAAGCCGGC-
TACCCGTT ATCAGGAGGCCAGCTACGACATTGA-
GGCAAAGACCAATTTCCATTACCGGCCCCAG TGG-
GATTCCGAGCACACCCTGAACGATCCCACGCGT-
ACCGCCATCCGCATGGAAGA CTGGTGCGCCG-
TTTCCGATCCCCGCCAGTTTTACTATGGCGCC-
TATGTCGGCAACCG GGCCAAGATGCAGGAGTC-
GGCCGAGACCAGCTTTGGCTTCTGCGAAAAG-
CGTAATC TGCTGACCCGCCTTTCCGAAGAAACC-
CAGAAGCAATTGTTGCGGCTGCTGGTGCCCC
TGCGTCATGTCGAGCTTGGCGCCAACATGAA-
CAACGCCAAGATCGCCGGTGATGCC ACCGC-
CACGACCGTCTCCCAGATGCACATCTACACTGG-
GATGGATCGCTTGGGCATT GGCCAGTACCT-
GTCCCGTATTGCATTGATGATTGATGGCAGC-
ACCGGTGCCGCTCTG GATGAGTCCAAGGCC-
TACTGGATGGATGACGAAATGTGGCAACC-
CATGCGCAAGCT GGTCGAAGACACGCTTGTGGTC-
GATGATTGGTTTGAGCTGACTCTGGTTCAGAACAT
TCTTATCGACGGAATGATGTACCCGCTGGTC-
TACGACAAGATGGACCAGTGGTTCGA AAGCCAG-
GGTGCTGAAGATGTGTCCATGCTCACGGAGTT-
CATGCGTGACTGGTACA AGGAATCCCTACGCT-
GGACTAATGCCATGATGAAAGCCGTGGCCGGT-
GAAAGTGAG ACTAACCGTGAGTTGCTTCAAAAA-
TGGATCGATCACTGGGAACCGCAGGCCTACGA
AGCCCTGAAACCTCTGGCCGAAGCCTCCGTTGG-
CATCGACGGGCTGAATGAAGCCC GGGCG-
GAACTCTCTGCCCGCCTGAAGAAATTCGAACTGC-
AGAGCCGGGGAGTCTCA GCATGAGCCAGCTTGT-
ATTTATTGTATTCCAGGACAACGACGACTCCCGC-
TACCTCG CGGAAGCCGTTATGGAAGATAACCC-
CGACGCCGAAATGCAGCACCAGCCGGCCATG
ATCCGGATCCAGGCGGAAAAACGTCTGGTGAT-
CAACCGCGAAACCATGGAAGAAA AGCTGGG-
GCGAGACTGGGATGTTCAGGAAATGCTCATAAATG-
TTATCAGCATCGCC GGCAACGTCGATGAAGACGAT-
GATCACTTCATTCTTGAATGGAATTAATCGGGAGA
AACATCATGGTTAGTAAAAACAAAAAGCTTAACCT-
TAAAGACAAGTATCAATACCT GACCCGGGA-
TATGGCCTGGGAACCGACCTATCAGGACAAGAAA-
GATATTTTTCCGG AGGAGGATTTTGAGGG-
TATCAAGATCACCGACTGGTCCCAGTGGGAA-
GATCCGTTC CGCCTGACCATGGATGCCTACTG-
GAAATACCAGGCGGAAAAAGAGAAGAAGCTGTA
CGCCATTTTCGATGCATTTGCCCAGAACAACGGC-
CACCAGAACATTTCAGACGCCCG TTATGT-
GAACGCGCTAAAACTGTTCATCAGTGGTATA-
TCTCCGCTTGAACATGCGGC GTTCCAGGGTTATTC-
CAAGGTCGGTCGCCAGTTTAGCGGCGCCG-
GGGCGCGGGTTGC CTGCCAGATGCAGGCAAT-
TGACGAGCTGCGTCATTCCCAGACCCAGCA-
ACACGCGA TGAGCCACTACAACAAGCACTT-
CAACGGTCTGCACGATGGCCCGCACATGCACGAT
CGGGTGTGGTACCTGTCGGTGCCGAAATCGTTCTTT-
GATGATGCACGCTCGGCTGGT CCGTTCGAG-
TTCCTGACGGCCATCTCATTCTCGTTCGAGTA-
TGTGCTCACCAACCTGT TGTTCGTACCGTT-
CATGTCGGGCGCTGCCTATAACGGCGACATGG-
CGACAGTCACCT TCGGTTTCTCCGCCCAGTCTG-
ACGAAGCCCGTCATATGACCCTGGGCCTTGAG-
GTGA TCAAGTTCATCCTCGAGCAGCACGAAGA-
TAACGTGCCCATCGTTCAGCGCTGGATCG
ACAAGTGGTTCTGGCGCGGATTTCGCCTGCT-
TAGCCTGGTCAGCATGATGATGGACT ACATGCTGC-
CAAACAAGGTCATGTCCTGGTCCGAGGCATGG-
GAAGTCTATTACGAG CAGAACGGCGGTGCTCT-
GTTCAAGGACCTGGAGCGATACGGCATCCGC-
CCGCCCAA ATACCAGGACGTGGCTAACGATGC-
CAAACATCACCTGAGCCACCAGCTTTGGACCA
CTTTCTACCAGTACTGCCAGGCCACCAACTTCCAT-
ACTTGGATTCCGGAGAAGGAAG AGATGGACTG-
GATGTCCGAGAAGTATCCGGACACTTTCGACAAG-
TACTACCGTCCG CGTTACGAGTACCTGGCGAA-
AGAGGCTGCCGCTGGCCGTCGCTTCTACAACAA-
CAC CCTGCCGCAGCTGTGCCAAGTGTGTCAGAT-
CCCGACCATTTTCACCGAGAAAGATGC CC CAAC-
CATGCTCAGCCATCGGCAGATAGAACATGAGGGC-
GAACGCTATCACTTCT GCTCTGACGGCTGCTGCGA-
CATCTTCAAACACGAGCCGGAGAAGTACATA-
CAGGCC TGGCTGCCGGTGCACCAGATCTACCAG-
GGCAACTGTGAAGGCGGGGATCTCGAGAC
CGTGGTGCAGAAGTATTACCACATCAATATCG-
GAGAGGACAATTTCGACTACGTTG GATCGCC-
CGACCAGAAACACTGGCTGTCGATCAAGGGCCG-
GAAGCCTGCAGACAAG AACCAGGACGCCGCCT-
GATATTGATTGGAGAGTCGCCCGGTAGCCGC-
TGGCACCGG GTGAAACACCCATAAAAACAACG-
AGGTGACCATCATGAGTGTAAACGCACTTTACG
ACTACAAGTTTGAACCTAAAGACAAGGTCG-
AGAACTTCCACGGCATGCAGCTGCTG TATGTC-
TACTGGCCCGATCACCTGCTGTTCTGCGCGCC-
CTTCGCGCTGCTGGTGCAG CCGGGTATGACCTT-
CAGTGCCCTGGTGGACGAGATTCTCAAGCCGGC-
TACCGCCGCG CACCCGGACTCTGCCAAGGCGG-
ACTTCCTGAATGCCGAGTGGTTGCTGAACGATGA
ACCGTTCACACCCAAGGCTGACGCCAGCCT-
GAAAGAGCAGGGTATTGATCACAAGA GCATGC-
TGACGGTGACCACGCCGGGCCTGAAGGGCATGGC-
GAACGCCGGTTACTGA GGGTAGCACTATGAGTTA-
CACCGTCACTATTGAGCCGATCGGCGAGCAGATT-
GAGG TAGAGGATGGCCAGACTATCCTCGCCGC-
CGCCCTGCGCCAGGGTGTCTGGCTGCCCT
TTGCCTGCGGCCACGGCACCTGTGCTACCTGTA-
AGGTTCAGGTGCTTGAAGGTGATG TCGAGATCG- GAAACGCCTCGCCCTTTGCGCTGATGGATATCG-AACGTGACGAGGGC AAGGTTCTGGCCTGCTGCGC-CACGGTTGAGAGCGACGTCACCATTGAGGTGGA-CAT CGATGTGGATCCGGATTTTGAGGGCTACC-CGGTGGAGGACTATGCCGCCATAGCGA CCGA-TATCGTCGAACTCTCTCCGACCATCAAGGGCATT-CACCTGAAACTGGACCGGC CGATGACATTCCAGG-CCGGCCAGTACATCAATATCGAACTGCCGGGTGTT-GAAGGC GCGAGGGCCTTCTCCCTGGCCAACCCGC-CCAGCAAAGCAGACGAAGTGGAGCTGCA TGTGCGCCTCGTTGAGGGCGGTGCTGCCACCACC-TACATCCACGAACAACTGAAAA CGGGTGATGC-GCTGAACCTTTCAGGCCCTTACGGCCAGTTC-TTCGTGCGTAGTTCCC AACCCGGCGATCTGATTTT-CATCGCCGGCGGATCCGGATTGTCCAGTCCCC-AGTCGA TGATCCTTGATCTGCTTGAGCAGAACGAT-GAGCGCAAGATCGTTCTGTTCCAGGGTG CCC-GAAACCTGGCAGAGCTTTACAACCGGGAGCTGT-TTGAGGCTCTGGATCGCGAC CACGACAATTT-CACCTACGTACCGGCGCTTAGCCAAGCCGACGAA-GACCCTGACTG GAAGGGCTTCCGAGGCTATGTC-CATGAGGCGGCCAACGCCCATTTCGATGGCCGGT TTGCCGGTAACAAGGCATACCTGTGCGGCCC-GCCTCCAATGATCGATGCGGCTATCA CGGCATT-GATGCAGGGGCGGCTGTTCGAGCGTGACATCTT-CATGGAGAAATTCCTG ACAGCGGCGGACGGAGCT-GAAGACACCCAGCGTTCGGCCCTGTTCAAGAAG-ATATA G (SEQ ID NO:4). Accordingly, in certain embodiments, the at least one gene encoding a polypeptide having phenol 2-monooxygenase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:4.

Genes encoding polypeptides having catechol-1,2-dioxygenase activity are known in the art and have been sequenced. The sequence of catechol-1,2-dioxygenase encoding genes are available (for example, catA, salD; see, GenBank Gene ID: 3609645, 3614680, 879147, 5191661 and 5191980). Accordingly, in certain embodiments, the gene encoding a polypeptide having catechol-1,2-dioxygenase activity is catA, or salD. In certain embodiments, the gene encoding a polypeptide having catechol-1,2-dioxygenase activity is catA. In certain embodiments, the catA gene has the following sequence: ATGACCGTGAAAAT-TTCCCACACTGCCGACATTCAAGCCTTCTTCAAC-CGGGTAGCT GGCCTGGACCATGCCGAAGGAAACC-CGCGCTTCAAGCAGATCATTCTGCGCGTGCT GCA-AGACACCGCCCGCCTGATCGAAGACCTGGAGAT-TACCGAGGACGAGTTCTGGC ACGCCGTCGAC-TACCTCAACCGCCTGGGCGGCCGTAACGAGGCAG-GCCTGCTGGCT GCTGGCCTGGGTATCGAGCACTTC-CTCGACCTGCTGCAGGATGCCAAGGATGCCGA AGCCGGCCTTGGCGGCGGCACCCCGCGCACCAT-CGAAGGCCCGTTGTACGTTGCCG GGGCGCCGC-TGGCCCAGGGCGAAGCGCGCATGGACGA-CGGCACTGACCCAGGCGT GGTGATGTTCCTT-CAGGGCCAGGTGTTCGATGCCGACGGCAAGCCG-TTGGCCGGTGC CACCGTCGACCTGTGGCACGC-CAATACCCAGGGCACCTATTCGTACTTCGATTCGAC CCAGTCCGAGTTCAACCTGCGTCGGCGTATCAT-CACCGATGCCGAGGGCCGCTACCG CGCGCGCTC-GATCGTGCCGTCCGGGTATGGCTGCGACCCGCAG-GGCCCAACCCAGG AATGCCTGGACCTGCTC-GGCCGCCACGGCCAGCGCCCGGCGCACGTGCA-CTTCTTCA TCTCGGCACCGGGGCACCGCCACCTG-ACCACGCAGATCAACTTTGCTGGCGACAAG TAC-CTGTGGGACGACTTTGCCTATGCCACCCGCGA-CGGGCTGATCGGCGAACTGCGT TTTGTCGAG-GATGCGGCGGCGGCGCGCGACCGCGGTGTGCAA-GGCGAGCGCTTTGC CGAGCTGTCATTCGACT-TCCGCTTGCAGGGTGCCAAGTCGCCTGACGCC-GAGGCGCG AAGCCATCGGCCGCGGGCGTTGCAG-GAGGGCTGA (SEQ ID NO:5). Accordingly, in certain embodiments, the at least one gene encoding a polypeptide having catechol-1,2-dioxygenase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:5.

Genes encoding polypeptides having tyrosine phenol lyase activity are known in the art and have been sequenced. The sequence of tyrosine phenol lyase encoding genes are available (for example, tutA; see GenBank Gene ID: L08484.1). Accordingly, in certain embodiments, the gene encoding a polypeptide having tyrosine phenol lyase activity is tutA. In certain embodiments, the tutA gene has the following sequence: ATGAATTATCCGGCAGA-ACCCTTCCGTATTAAAAGCGTTGAAACTGTATCTAT-GATC CCGCGTGATGAACGCCTCAAGAAAATGCAG-GAAGCGGGTTACAATACTTTCCTGTT AAATTCGA-AAGATATTTATATTGACCTGCTGACAGACAGTG-GCACTAACGCAATGA GCGACAAGCAGTGGGCCG-GAATGATGATGGGTGATGAAGCGTACGCGGGCAG-CGA AAACTTCTATCATCTGGAAAGAACCGTGCAG-GAACTGTTCGGCTTTAAACATATTGT TCCGACT-CACCAGGGGCGTGGCGCAGAAAACCTGTTATCG-CAGTTGGCTATTAAAC CTGGGCAATATGTTGCCGG-GAATATGTATTTCACCACCACCCGTTATCACCAG-GAAA AAAATGGTGCGGTGTTTGTCGATATCGTT-CGTGACGAAGCGCACGATGCCGGTCTGA ATAT-TGCGTTTAAAGGTGATATCGATCTTAAAAAATTA-CAAAAGCTGATTGATGAAA AAGGCGCAGAAAAT-ATTGCGTATATCTGCCTGGCGGTGACGGTTAACCT-CGCAGGT GGGCAGCCGGTCTCGATGGCCAA-CATGCGTGCGGTGCGTGAACTGACAGAAGCGCA CGGCATTAAAGTGTTCTACGACGCCACCCGTTGC-GTGGAAAACGCCTACTTTATCAA AGAGCAAGA-GCAGGGCTTTGAGAACAAGAGCATCGCCGAGAT-CGTGCATGAGATGT TCAGCTACGCCGACGGTTG-TACCATGAGTGGTAAAAAAGACTGTCTGGTGAA-CATC GGCGGTTTCCTGTGCATGAACGATGACGA-AATGTTCTCTTCTGCCAAAGAGTTAGTC GTGGTC-TACGAAGGGATGCCATCTTACGGCGGCCTGGCCG-GACGTGATATGGAAGC CATGGCGATTGGCCTG-CGCGAAGCCATGCAATACGAATATATTGAGCAC-CGCGTGAAGCAGGTTCGCTACCTGGGCGATAAGCT-GAAAGCCGCTGGCGTACCGATTGTTGAA CCGGTA-GGCGGTCACGCGGTATTCCTCGATGCGCGTC-GCTTCTGCGAGCATCTGACG CAGGACGAGTT-CCCGGCGCAAAGCCTGGCGGCGAGCATTTATGTG-GAAACTGGTGT GCGCAGTATGGAACGCGGAATAA-TCTCTGCAGGCCGTAATAACGTGACCGGTGAAC ACCACAGACCGAAACTGGAAACCGTGCGTCTGAC-TATTCCACGCCGCGTTTATACCT ACGCGCACATG-GATGTCGTAGCTGACGGTATTATTAAACTT-TACCAGCACAAAGAA GATATTCGCGGGCTGAAG-TTTATTTACGAGCCGAAGCAGTTGCGTTTCTT-TACTGCA CGCTTTGACTATATCTAA (SEQ ID NO:6). Accordingly, in certain embodiments, the at least one gene encoding a polypeptide having tyrosine phenol lyase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:6.

Genes encoding polypeptides having chorismate lyase activity are known in the art and have been sequenced. The sequence of chorismate lyase encoding genes are available (for example, ubiC; see GenBank Gene ID: ECK4031). Accordingly, in certain embodiments, the gene encoding a polypeptide having chorismate lyase activity is ubiC. In certain embodiments, the ubiC gene has the following sequence:

```
                                        (SEQ ID NO: 7)
ATGTCACACCCCGCGTTAACGCAACTGCGTGCGCTGCGCTATTGTAAAGA

GATCCCTGCCCTGGATCCGCAACTGCTCGACTGGCTGTTGCTGGAGGATT

CCATGACAAAACGTTTTGAACAGCAGGGAAAAACGGTAAGCGTGACGATG

ATCCGCGAAGGGTTTGTCGAGCAGAATGAAATCCCCGAAGAACTGCCGCT

GCTGCCGAAAGAGTCTCGTTACTGGTTACGTGAAATTTTGTTATGTGCCG

ATGGTGAACCGTGGCTTGCCGGTCGTACCGTCGTTCCTGTGTCAACGTTA

AGCGGGCCGGAGCTGGCGTTACAAAAATTGGGTAAAACGCCGTTAGGACG

CTATCTGTTCACATCATCGACATTAACCCGGGACTTTATTGAGATAGGCC

GTGATGCCGGGCTGTGGGGGCGACGTTCCCGCCTGCGATTAAGCGGTAAA

CCGCTGTTGCTAACAGAACTGTTTTTACCGGCGTCACCGTTGTACTAA.
```

Accordingly, in certain embodiments, the at least one gene encoding a polypeptide having chorismate lyase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:7.

Genes encoding polypeptides having p-hydroxybenzoate decarboxylase activity are known in the art and have been sequenced. The sequence of p-hydroxybenzoate decarboxylase encoding genes are available (for example, the operon kpdBCD; see GenBank Gene ID: KUP82937.1). Accordingly, in certain embodiments, the genes encoding a polypeptide having p-hydroxybenzoate decarboxylase activity is the kpdBCD operon. In certain embodiments, the kpdBCD operon has the following sequence: ATGGGCCAAAAC-
CACCATCGAGCTGGAAACGCCCTGGACAGCGCG-
CGAAGTGGCCG CGCTGGCGGACTTTTCC-
CACAGCCCGGCAGACCAGGCCGCCACCATCTC-
TTCCGGTT CATTTCGTACCGACGGCATGATCGTTAT-
TCCCTGCAGTATGAAAACGCTGGCAGGCA TTCGC-
GCGGGTTATGCCGAAGGGCTGGTGGGCCGCGCG-
GCGGACGTGGTGCTCAAA GAGGGGCGCAA-
GCTGGTGCTGGTCCCGCGGGAAATGCCGCT-
CAGCACGATCCATCT GGAGAACATGCTGGC-
GCTGTCGCGCATGGGCGTGGCGATGGTGCCGCC-
GATGCCGG CTTACTACAACCACCCGGAGACGGTT-
GACGATATCACCAATCATATCGTCACCCGGG TGC-
TGGATCAGTTTGGCCTCGACTATCACAAAGC-
GCGCCGCTGGAACGGCTTGCGCA CGGCAGAA-
CAATTTGCACAGGAGATCGAATAATGGCTTTTGAT-
GATTTGCGCAGCTT TTTGCAGGCGCTGGATGAC-
CAGGGACAACTGCTGAAAATCAGTGAAGAGGT-
GAACG CTGAGCCCGATCTGGCGGCGGCCGC-
CAATGCGACCGGACGCATCGGCGACGGCGCC
CCGGCGCTGTGGTTCGATAATATTCGCGGCTT-
TACCGACGCCCGCGTGACGATGAAC ACCAT-
CGGCTCGTGGCAGAACCATGCCATCTCGCT-
GGGCCTGCCGCCTAACACGCCG GTGAAAAAGCA-
GATTGATGAATTCATTCGCCGCTGGGATAACTTCC-
CGGTGACGCC AGAGCGCCGCGCCAACCCGGC-
GTGGGCGGAAAACACCGTGGATGGCGACGATATC
AACCTGTTCGATATTCTGCCACTGTTCCGCCT-
CAACGATGGTGACGGCGGTTTCTAC CTCGA-
TAAAGCCTGTGTCGTATCACGCGACCCGCTT-
GATCCTGACAACTTCGGTAAG CAAAACGTCGG-
TATCTACCGCATGGAAGTGAAAGGCAAGCGCA-
AGCTCGGCCTGCA GCCGGTGCCGATGCACGA-
TATCGCGCTGCATCTGCACAAAGCGGAAGAGC-
GTGGGG AAGATCTGCCGATCGCTATTACCCTC-
GGTAACGACCCGATTATTACCCTGATGGGCG
CCACGCCGCTGAAATACGATCAATCAGAATAT-
GAAATGGCTGGCGCGCTGCGCGAG AGCCCGTA-
TCCCATCGCCACCGCGCCGCTGACCGGCTTTGA-
CGTGCCCTGGGGTTCG GAAGTGATCCTCGAAG-
GGGTCATTGAAGGGCGTAAGCGTGAGATCGA-
GGGGCCGTT CGGTGAGTTTACCGGTCACTACTC-
CGGCGGTCGTAACATGACGGTAGTGCGTATCGA
CAAAGTCTCGTATCGCAGCAAACCGATTTTT-
GAATCGCTCTATCTCGGTATGCCGTG GACCGAGAT-
TGACTATCTGATGGGCCCGGCGACCTGCGT-
GCCGCTGTATCAGCAGTT GAAGGCAGAGTTCCCG-
GAAGTGCAGGCGGTCAACGCCATGTACACC-
CATGGTCTGC TGGCGATCATCTCCACCAAAAA-
ACGCTACGGCGGTTTTGCCCGCGCGGTGGGCCTGC
GGGCGATGACCACTCCGCACGGCCTCGGCTATGT-
GAAGATGGTGATCATGGTTGAT GAAGACGTC-
GACCCGTTCAACCTGCCGCAGGTGATGTGGGC-
GCTCTCCTCGAAAGTT AACCCGGCGGGTGAC-
CTGGTGCAGTTGCCGAACATGTCGGTCCTTGAACT-
TGACCCT GGCTCCAGCCCGGCAGGCATCACCGAC-
AAACTGATTATCGACGCCACCACCCCGGT TGCGC-
CGGACCTTCGCGGCCACTACAGCCAGCCGGTGCA-
GGATCTGCCGGAAACCA AAGCCTGGGCTGAAAA-
ACTGACCGCTATGCTGGCCAACCGTAAATAAGGA-
GAAGAA GATGATTTGTCCACGTTGCGCCGAT-
GAAAAGATTGAAGTGATGGCAACCTCGCCGG
TGAAAGGGGTCTGGACCGTGTATCAGTGCCAGCA-
CTGTCTTTACACCTGGCGAGATA CCGAGCCGCT-
GCGCCGCACCAGTCGCGAACACTATCCGGAAGC-
GTTCCGCATGACG CAGAAAGATATTGAT-
GAGGCACCGCAGGTGCCACACGTACCGCCGCTAT-
TGCCGGA AGATAAGCGTTAA (SEQ ID NO:8). Accordingly, in certain embodiments, the at least one gene encoding a polypeptide having p-hydroxybenzoate decarboxylase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8.

Genes encoding polypeptides having p-hydroxybenzoate hydroxylase activity are known in the art and have been sequenced. The sequence of p-hydroxybenzoate hydroxylase encoding genes are available (for example, pobA; see GenBank Gene ID: AAA88455.1). Accordingly, in certain embodiments, the gene encoding a polypeptide having p-hydroxybenzoate hydroxylase activity is pobA. In certain embodiments, the pobA gene has the following sequence: ATGAAGACTCAAGTCGCCATCATCGGCGCCGG-
TCCGTCCGGCCTCCTGCTCGGCCAG TTGCTGCA-
CAAGGCCGGCATCGACAACGTGATCCTCGA-
ACGCCAGACCCCGGACTA CGTGCTCGGCCG-
CATCCGCGCCGGCGTGCTGGAACAGGGTATGGT- CGACCTGCTGC GCGAGGCCGGCGTCGACCGGCG-CATGGCGCGCGACGGGCTGGTCCACGAAGGCGTG GAGATCGCCTTCGCCGGGCAGCGCCGGCG-CATCGACCTGAAGCGCCTGAGCGGCGG CAA-GACGGTGACGGTCTACGGCCAGACCGAGGT-CACCCGCGACCTCATGGAGGCCC GCGAAGCC-TGCGGCGCCACTACCGTCTACCAGGCCGC-CGAGGTGCGCCTGCACGAC CTGCAAGGT-GAGCGCCCCTACGTGACCTTCGAACGCGACGGCG-AACGGCTGCGCCT GGATTGCGACTACATCGC-CGGCTGCGATGGCTTCCACGGCATCTCGCG-GCAATCGAT CCCGGCGGAGCGGCTGAAGGTCTT-CGAGCGGGTCTATCCGTTCGGCTGGCTCGGCCT GCTCGCCGACACCCCGCCGGTGAGCCACGAACT-GATCTACGCCAACCATCCGCGCG GCTTCGCCCT-GTGCAGCCAGCGTTCGGCCACCCGCAGCCGCTAC-TACGTGCAGGTGC CATTGTCGGAGAAGGTC-GAGGACTGGTCCGACGAGCGCTTCTGGACG-GAACTGAAG GCGCGACTCCCGTCCGAGGTGGCG-GAGAAACTGGTGACCGGACCTTCGCTGGAGAA GAGCATCGCGCCGCTGCGCAGCTTCGTGGTC-GAGCCGATGCAGCATGGCCGGCTGT TCCTCGCCG-GCGACGCCGCGCACATCGTGCCGCCCACCGGCGC-CAAGGGACTGAAC CTGGCCGCCAGCGACGT-CAGCACGCTCTACCGGCTGCTGCTGAAGGCC-TACCGCGA AGGGCGCGGCGAACTGCTGGAACGC-TATCGGCAATCTGCCTGCGGCGGATCTGGA AGGCCGAACGCTTCTCCTGGTGGATGACT-TCGGTGCTGCATCGCTTCCCCGACACCG ACGCGT-TCAGCCAGCGCATCCAGCAGACCGAACTGGAGT-ATTACCTGGGCTCCGAG GCGGGCCTGGCGAC-CATCGCCGAGAACTATGTCGGCCTGCCCTACGAG-GAAATCGA GTAG (SEQ ID NO:9). Accordingly, in certain embodiments, the at least one gene encoding a polypeptide having p-hydroxybenzoate hydroxylase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:9.

Genes encoding polypeptides having protocatechuate decarboxylase activity are known in the art and have been sequenced. The sequence of protocatechuate decarboxylase encoding genes are available (for example, aroY; see GenBank Gene ID: BAH20873.2). Accordingly, in certain embodiments, the gene encoding a polypeptide having protocatechuate decarboxylase activity is aroY. In certain embodiments, the aroY gene has the following sequence:

```
                                          (SEQ ID NO: 10)
ATGACCGCACCGATTCAGGATCTGCGCGACGCCATCGCGCTGCTGCAACA

GCATGACAATCAGTATCTCGAAACCGATCATCCGGTTGACCCTAACGCCG

AGCTGGCCGGTGTTTATCGCCATATCGGCGCGGGCGGCACCGTGAAGCGC

CCCACCCGCATCGGGCCGGCGATGATGTTTAACAATATTAAGGGTTATCC

ACACTCGCGCATTCTGGTGGGTATGCACGCCAGCCGCCAGCGGGCCGCGC

TGCTGCTGGGCTGCGAAGCCTCGCAGCTGGCCCTTGAAGTGGGTAAGGCG

GTGAAAAAACCGGTCGCGCCGGTGGTCGTCCCGGCCAGCAGCGCCCCCTG

CCAGGAACAGATCTTTCTGGCCGACGATCCGGATTTTGATTTGCGCACCC

TGCTTCCGGCGCACACCAACACCCCTATCGACGCCGGCCCCTTCTTCTGC

CTGGGCCTGGCGCTGGCCAGCGATCCCGTCGACGCCTCGCTGACCGACGT
```

-continued

```
CACCATCCACCGCTTGTGCGTCCAGGGCCGGGATGAGCTGTCGATGTTTC

TTGCCGCCGGCCGCCATATCGAAGTGTTTCGCCAAAAGGCCGAGGCCGCC

GGCAAACCGCTGCCGATAACCATCAATATGGGTCTCGATCCGGCCATCTA

TATTGGCGCCTGCTTCGAAGCCCCTACCACGCCGTTCGGCTATAATGAGC

TGGGCGTCGCCGGCGCGCTGCGTCAACGTCCGGTGGAGCTGGTTCAGGGC

GTCAGCGTCCCGGAGAAAGCCATCGCCCGCGCCGAGATCGTTATCGAAGG

TGAGCTGTTGCCTGGCGTGCGCGTCAGAGAGGATCAGCACACCAATAGCG

GCCACGCGATGCCGGAATTTCCTGGCTACTGCGGCGGCGCTAATCCGTCG

CTGCCGGTAATCAAAGTCAAAGCAGTGACCATGCGAAACAATGCGATTCT

GCAGACCCTGGTGGGACCGGGGGAAGAGCATACCACCCTCGCCGGCCTGC

CAACGGAAGCCAGTATCTGGAATGCCGTCGAGGCCGCCATTCCGGGCTTT

TTACAAAATGTCTACGCCCACACCGCGGGTGGCGGTAAGTTCCTCGGGAT

CCTGCAGGTGAAAAAACGTCAACCCGCCGATGAAGGCCGGCAGGGGCAGG

CCGCGCTGCTGGCGCTGGCGACCTATTCCGAGCTAAAAAATATTATTCTG

GTTGATGAAGATGTCGACATCTTTGACAGCGACGATATCCTGTGGGCGAT

GACCACCCGCATGCAGGGGGACGTCAGCATTACGACAATCCCCGGCATTC

GCGGTCACCAGCTGGATCCGTCCCAGACGCCGGAATACAGCCCGTCGATC

CGTGGAAATGGCATCAGCTGCAAGACCATTTTTGACTGCACGGTCCCCTG

GGCGCTGAAATCGCACTTTGAGCGCGCGCCGTTTGCCGACGTCGATCCGC

GTCCGTTTGCACCGGAGTATTTCGCCCGGCTGGAAAAAAACCAGGGTAGC

GCAAAATAA.
```

Accordingly, in certain embodiments, the at least one gene encoding a polypeptide having protocatechuate decarboxylase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:10.

Genes encoding polypeptides having 3-dehydroshikimate dehydratase activity are known in the art and have been sequenced. The sequence of 3-dehydroshikimate dehydratase encoding genes are available (for example, aroZ, quiC, qsuB; see GenBank Gene IDs: 5987244, BAF53460.1). Accordingly, in certain embodiments, the gene encoding a polypeptide having 3-dehydroshikimate dehydratase activity is qsuB. In certain embodiments, the qsuB gene has the following sequence:

```
                                          (SEQ ID NO: 11)
ATGCGTACATCCATTGCCACTGTTTGTTTGTCCGGAACTCTTGCTGAAAA

GCTGCGCGCAGCTGCAGATGCTGGATTTGATGGTGTGGAAATCTTCGAGC

AGGACTTGGTGGTTTCCCCGCATTCGGCAGAGCAGATTCGTCAGCGGGCT
```

-continued

```
CAGGATTTGGGATTAACCCTGGATCTGTTCCAGCCGTTTCGAGATTTCGA

AGGTGTGGAAGAAGAGCAGTTTCTGAAGAATCTGCACCGCTTGGAAGAGA

AGTTCAAGCTGATGAACAGGCTTGGCATTGAGATGATCTTGTTGTGTTCC

AATGTGGGCACCGCGACCATCAATGATGATGACCTTTTCGTGGAGCAGTT

GCATCGTGCAGCAGATTTGGCTGAGAAGTACAACGTCAAGATTGCTTATG

AAGCGTTGGCGTGGGGCAAGTTTGTCAATGATTTTGAGCATGCGCATGCA

CTTGTGGAGAAGGTGAATCACAAGGCGCTGGGAACCTGCTTGGATACGTT

CCATATTCTTTCCCGTGGTTGGGAAACCGACGAGGTGGAGAACATCCCTG

CGGAGAAGATCTTCTTTGTTCAGTTAGCGGATGCGCCGAAGCTGAGCATG

GACATTTTGTCCTGGTCGCGTCACCACCGTGTTTTCCCTGGTGAAGGCGA

TTTCGATCTGGTGAAATTCATGGTTCATCTGGCCAAGACGGGTTATGATG

GCCCGATTTCTTTGGAGATCTTCAACGATTCCTTCCGCAAGGCCGAGGTT

GGTCGCACCGCGATTGATGGGTTGCGTTCTTTGCGTTGGTTGGAAGATCA

GACCTGGCATGCGCTAAATGCTGAGGATCGTCCAAGCGCTCTTGAACTGC

GTGCACTTCCTGAGGTCGCGGAACCTGAGGGTGTTGATTTCATTGAGATC

GCCACTGGACGTTTGGGTGAGACCATTCGGGTTCTTCATCAATTGGGTTT

CCGCTTGGGTGGTCATCACTGCAGTAAGCAGGATTACCAGGTATGGACCC

AGGGCGATGTGCGCATTGTGGTGTGTGATCGTGGGGTCACCGGGGCTCCA

ACCACGATCTCTGCGATGGGCTTTGACACCCCCGATCCAGAAGCTGCTCA

TGCCCGTGCGGAATTGCTGCGGGCTCAGACAATTGATCGTCCCCACATCG

AGGGCGAAGTTGACCTAAAAGGTGTGTACGCACCGGATGGGGTGGAGCTG

TTTTTCGCGGGGCCGAGCCCCGATGGAATGCCCGAGTGGCTGCCGGAATT

CGGCGTCGAAAAGCAAGAAGCTGGTCTCATTGAAGCCATCGACCACGTCA

ATTTCGCCCAGCCGTGGCAACATTTTGATGAGGCAGTGCTGTTTTACACC

GCGCTGATGGCGTTGGAGACTGTGCGTGAGGATGAGTTCCCGAGCCCAAT

TGGTTTGGTGCGCAATCAGGTGATGCGTTCGCCGAATGATGCGGTGCGGT

TGCTGCTCAGCGTGGCGCCGGAGGACGGTGAGCAGGGAGATTTCCTCAAC

GCGGCCTACCCGGAGCACATTGCGTTGGCCACGGCGGACATCGTGGCGGT

GGCTGAACGTGCGCGCAAACGAGGCCTGGATTTCTTGCCCGTCCCAGAGA

ATTACTACGACGATGTGCAGGCGCGTTTTGATTTGCCGCAGGAATTCTTG

GACACACTCAAGGAAAACCACCTGCTTTACGACCGCGACGAGAACGGCGA

ATTCCTCCACTTTTACACCCGCACGTTGGGCACGCTGTTCTTCGAAGTGG

TGGAACGCCGCGGCGGTTTTGCAGGTTGGGGCGAAACAAACGCTCCGGTG

CGGTTGGCGGCGCAGTATCGTGAGGTGCGGGACCTCGAGCGGGGAATCCC

AAACTAG.
```

Accordingly, in certain embodiments, the at least one gene encoding a polypeptide having 3-dehydroshikimate dehydratase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:11.

Genes encoding polypeptides having feedback resistant (fbr) chorismate mutase/prephenate dehydrogenase activity are known in the art and have been sequenced. The sequence of chorismate mutase/prephenate dehydrogenase encoding genes are available (for example, tyrA$^{fbr}$; see GenBank Gene ID: AAA24331.1). Accordingly, in certain embodiments, the gene encoding a polypeptide having feedback resistant chorismate mutase/prephenate dehydrogenase activity is tyrA$^{fbr}$. In certain embodiments, the tyrA$^{fbr}$ gene has the following sequence: ATGGTTGCTGAAT-TGACCGCATTACGCGATCAAATTGATGAAGTCGA-TAAAG CGCTGCTGAATTTATTAGCGAAGCGTCTG-GAACTGGTTGCTGAAGTGGGCGAGGTG AAAA-GCCGCTTTGGACTGCCTATTTATGTTCCGGAGCG-CGAGGCATCTATGTTGGCC TCGCGTCGTGCAGA-GGCGGAAGCTCTGGGTGTACCGCCGGATCTGATT-GAGGATGT TTTGCGTCGGGTGATGCGTGAATCT-TACTCCAGTGAAAACGACAAAGGATTTAAAA CACTTTGTCCGTCACTGCGTCCGGTGGTTATCGT-CGGCGGTGGCGGTCAGATGGGAC GCCTGTTC-GAGAAGATGCTGACCCTCTCGGGTTATCAGGTGCG-GATTCTGGAGCAAC ATGACTGGGATCGAGCGGCT-GATATTGTTGCCGATGCCGGAATGGTGATTGT-TAGTG TGCCAATCCACGTTACTGAGCAAG-TTATTGGCAAATTACCGCCTTTACCGAAAGATT GTATTCTGGTCGATCTGGCATCAGTGAAAAATGG-GCCATTACAGGCCATGCTGGTGG CGCAT-GATGGTCCGGTGCTGGGGCTACACCCGATGTTC-GGTCCGGACAGCGGTAGC CTGGCAAAGCAAG-TTGTGGTCTGGTGTGATGGACGTAAACCGGAAG-CATACCAATG GTTTCTGGAGCAAATTCAGGTCTG-GGGCGCTCGGCTGCATCGTATTAGCGCCGTCGA GCACGATCAGAATATGGCGTTTATTCAGGCA-CTGCGCCACTTTGCTACTTTTGCTTA CGGGCTG-CACCTGGCAGAAGAAAATGTTCAGCTTGAGCA-ACTTCTGGCGCTCTCTTC GCCGATTTACCGCCTT-GAGCTGGCGATGGTCGGGCGACTGTTTGCT-CAGGACCCGCA GCTTTATGCCGACATCAT-TATGTCGTCAGAGCGTAATCTGGCGTTAAT-CAAACGTTA CTATAAGCGTTTCGGCGAGGCGATT-GAGTTGCTGGAGCAGGGCGATAAGCAGGCGT TTATTGACAGTTTCCGCAAGGTGGAGCACTGGT-TCGGCGATTACGCACAGCGTTTTC AGAGT-GAAAGCCGCGTGTTATTGCGTCAGGCGAATGA-CAATCGCCAGTAA (SEQ ID NO:56). Accordingly, in certain embodiments, the at least one gene encoding a polypeptide having chorismate mutase/prephenate dehydrogenase activity comprises/consists of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:56.

Thus, in certain embodiments, the at least one gene encoding a polypeptide having isochorismate synthase activity comprises a sequence having at least about 70% sequence identity to SEQ ID NO:1; the at least one gene encoding a polypeptide having isochorismate pyruvate lyase activity comprises a sequence having at least about 70% sequence identity to SEQ ID NO:2; the at least one gene encoding a polypeptide having salicylate decarboxylase activity comprises a sequence having at least about 70% sequence identity to SEQ ID NO:3; the at least one gene encoding a polypeptide having phenol 2-monooxygenase activity comprises a sequence having at least about 70% sequence identity to SEQ ID NO:4; the at least one gene encoding a polypeptide having 1,2-catechol dioxygenase activity comprises a sequence having at least about 70% sequence identity to SEQ ID NO:5; the at least one gene encoding a polypeptide having tyrosine phenol lyase activity comprises a sequence having at least about 70% sequence identity to SEQ ID NO:6; the at least one gene encoding a polypeptide having chorismate lyase activity comprises a sequence having at least about 70% sequence identity to SEQ ID NO:7; the at least one gene encoding a polypeptide having p-hydroxybenzoate decarboxylase activity comprises a sequence having at least about 70% sequence identity to SEQ ID NO:8; the at least one gene encoding a polypeptide having p-hydroxybenzoate hydroxylase activity comprises a sequence having at least about 70% sequence identity to SEQ ID NO:9; the at least one gene encoding a polypeptide having protocatechuate decarboxylase activity comprises a sequence having at least about 70% sequence identity to SEQ ID NO:10; and/or the at least one gene encoding a polypeptide having 3-dehydroshikimate dehydratase activity comprises a sequence having at least about 70% sequence identity to SEQ ID NO:11.

In certain embodiments, the at least one gene encoding a polypeptide having isochorismate synthase activity is entC, menF, pchA or ICS1; the at least one gene encoding a polypeptide having isochorismate pyruvate lyase activity is pchB; the at least one gene encoding a polypeptide having salicylate decarboxylase activity is SDC; the at least one gene encoding a polypeptide having phenol 2-monooxygenase activity is dmpLMNOP or phKLMNOP; the at least one gene encoding a polypeptide having 1,2-catechol dioxygenase activity is catA or salD; the at least one gene encoding a polypeptide having tyrosine phenol lyase activity is tutA; the at least one gene encoding a polypeptide having chorismate lyase activity is ubiC; the at least one gene encoding a polypeptide having p-hydroxybenzoate decarboxylase activity is kpdBCD; the at least one gene encoding a polypeptide having p-hydroxybenzoate hydroxylase activity is pobA; the at least one gene encoding a polypeptide having protocatechuate decarboxylase activity is aroY; and/or the at least one gene encoding a polypeptide having 3-dehydroshikimate dehydratase activity is aroZ, quiC or qsuB.

In certain embodiments, the recombinant host cell comprises a plasmid combination selected from the group consisting of: pY3 and pTutA-pPh (CAT2); pSDC-PchB-EntC and pPh (CAT3); pUbiC-Kpd and pPh (CAT4); pUbiC-PobA and pAroY (CAT5); pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA; pQsuB-AroY-CatA (MAF); pTyrAfbr-TutA (PHI); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); and pTyrAfbr-TutA, pSDC-PchB-EntC, and pUbiC-Kpd (PHF4).

In certain embodiments, the recombinant host cell is *E. coli* NST74 ΔpheA and comprises a plasmid combination selected from the group consisting of: pY3 and pTutA-pPh (CAT2); pSDC-PchB-EntC and pPh (CAT3); pUbiC-Kpd and pPh (CAT4); and pUbiC-PobA and pAroY (CAT5).

In certain embodiments, the recombinant host cell is *E. coli* NST74 ΔpheA and comprises a plasmid combination selected from the group consisting of: pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA and pQsuB-AroY-CatA (MAF).

In certain embodiments, the recombinant host cell is *E. coli* NST74 ΔpheA ΔpykA ΔpykF and comprises a plasmid combination selected from the group consisting of: pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA and pQsuB-AroY-CatA (MAF).

In certain embodiments, the recombinant host cell is *E. coli* NST74 ΔpheA ΔpykA ΔpykF Δcrr and comprises a plasmid combination selected from the group consisting of: pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA and pQsuB-AroY-CatA (MAF).

In certain embodiments, the recombinant host cell is *E. coli* NST74 ΔpheA ΔpykA ΔpykF Δcrr and comprises a plasmid combination pQsuB-AroY-CatA (MA1).

In certain embodiments, the recombinant host cell is *E. coli* NST74 ΔpheA ΔpykA ΔpykF Δcrr and comprises a plasmid combination pUbiC-PobA and pQsuB-AroY-CatA (MAF).

In certain embodiments, the recombinant host cell is *E. coli* NST74 ΔpheA ΔpykA ΔpykF Δcrr and comprises a plasmid combination selected from the group consisting of: pTyrAfbr-TutA (PH1); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); and pTyrAfbr-TutA, pSDC-PchB-EntC, and pUbiC-Kpd (PHF4).

In certain embodiments, the recombinant host cell is *E. coli* NST74 ΔpheA and comprises a plasmid combination selected from the group consisting of: pTyrAfbr-TutA (PH1); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); and pTyrAfbr-TutA, pSDC-PchB-EntC, and pUbiC-Kpd (PHF4).

It will be appreciated that the present embodiments are not limited to the specific genes mentioned above, but will encompass any suitable homologs of such genes that may be obtained by standard methods. Methods of obtaining homologs to these genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR)). For example, genes encoding homologs of the polypeptides that alone or in combination have the above-mentioned activities could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art. Moreover, the entire sequences can be used directly to synthesize DNA probes by methods known to those skilled in the art, such as random primers DNA labeling, nick translation, or end-labeling techniques or RNA probes using available in vitro transcription systems. In addition, specific primers can be designed and used to amplify a part of or full length of the instant sequences. The resulting amplification products can be labeled directly during amplification reactions or labeled after amplification reactions, and used as probes to isolate full-length cDNA or genomic fragments under conditions of appropriate stringency.

Synthetic Primers for Cloning

Described herein are methods for the microbial production of biochemical products, such as phenol, catechol, and muconic acid, from renewable substrates using recombinant host cells. Specifically, embodiments may involve the cloning and incorporation of genes encoding polypeptides having the above described activity(ies) into a single host organism and the use of those organisms to convert renewable resources such as glucose, for example, to phenol, catechol and muconic acid. As discussed below, synthetic DNA primers used to clone the aforementioned genes are known in the art.

In certain embodiments, the gene encoding a polypeptide having isochorismate synthase activity is entC. As described in the Examples, the entC gene was cloned using two synthetic nucleotide primers containing the following sequences: ATA GGA TCC AGG ATA AAT AAT GGA TAC GTC ACT GGC TGA (SEQ ID NO: 12) and ATT CTG CAG TTA ATG CAA TCC AAA AAC GTT (SEQ ID NO: 13). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:12 and/or SEQ ID NO: 13 is used to clone a gene encoding a polypeptide having isochorismate synthase activity (e.g., entC).

In certain embodiments, the gene encoding a polypeptide having isochorismate pyruvate lyase activity is pchB. As described in the Examples, the pchB gene was cloned using two synthetic nucleotide primers containing the following sequences: AAT ATC TAG ATT CCC GAG AGG TTG CAT GAT GAA AAC T (SEQ ID NO: 14) and ATT GGA TCC TTA TGC GGC ACC CCG TGT CTG G (SEQ ID NO: 15). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:14 and/or SEQ ID NO: 15 is used to clone a gene encoding a polypeptide having isochorismate pyruvate lyase activity (e.g., pchB).

In certain embodiments, the gene encoding a polypeptide having salicylate decarboxylase activity is SDC. As described in the Examples, the SDC gene was cloned using two synthetic nucleotide primers containing the following sequences: ATA GAA TTC AGG AGG ATA AAT AAT GCG TGG TAA AGT TAG CCT G (SEQ ID NO: 16) and ATT GGA TCC TTA GGC TTC GCT GTC ATA GAA T (SEQ ID NO: 17). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:16 and/or SEQ ID NO: 17 is to clone a gene encoding a polypeptide having salicylate decarboxylase activity (e.g., SDC).

In certain embodiments, the gene encoding a polypeptide having phenol hydroxylase activity is phKLMNOP. As described in the Examples, the phKLMNOP gene was cloned using two synthetic nucleotide primers containing the following sequences: ATA TCT AGA AGG AGG ATA AAT AGA GCT CGT GCT GCC TCA CGA (SEQ ID NO: 18) and ATT CCT GCA GGA TGC CCA TGA CTA TAT CTT CTT GAA CAG GGC (SEQ ID NO: 19). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:18 and/or SEQ ID NO: 19 is used to clone a gene encoding a polypeptide having phenol hydroxylase activity (e.g., phKLMNOP).

In certain embodiments, the gene encoding a polypeptide having catechol 1,2-dioxygenase activity is catA. As described in the Examples, the catA gene was cloned using two synthetic nucleotide primers containing the following sequences: ATA AGA TCT AGG AGG ATA AAT AAT GAC CGT GAA AAT TTC CCA C (SEQ ID NO: 20) and ATT TCT AGA TCA GCC CTC CTG CAA CGC (SEQ ID NO: 21). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:20 and/or SEQ ID NO: 21 is used to clone a gene encoding a polypeptide having catechol 1,2-dioxygenase activity (e.g., catA).

In certain embodiments, the gene encoding a polypeptide having tyrosine phenol lyase activity is tutA. As described in the Examples, the tutA gene was cloned using two synthetic nucleotide primers containing the following sequences: ATA GAA TTC AGG AGG ATA AAT AAT GAA TTA TCC GGC AGA ACC (SEQ ID NO: 22) and ATT TCT AGA TTA GAT ATA GTC AAA GCG TGC AGT A (SEQ ID NO: 23). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:22 and/or SEQ ID NO: 23 is used to clone a gene encoding a polypeptide having tyrosine phenol lyase activity (e.g., tutA).

In certain embodiments, the gene encoding a polypeptide having chorismate pyruvate lyase activity is ubiC. As described in the Examples, the ubiC gene was cloned using two synthetic nucleotide primers containing the following sequences: ATA GAA TTC AGG AGG ATA AAT AAT GTC ACA CCC CGC GTT AAC G (SEQ ID NO: 24) and ATT AGA TCT TTA GTA CAA CGG TGA CGC CGG TAA A (SEQ ID NO: 25). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:24 and/or SEQ ID NO: 25 is used to clone a gene encoding a polypeptide having chorismate synthase activity (e.g., ubiC).

In certain embodiments, the gene encoding a polypeptide having p-hydroxybenzoate decarboxylase activity is kpdBCD. As described in the Examples, the kpdBCD gene was cloned using two synthetic nucleotide primers containing the following sequences: ATA GGA TCC CCC GTC CGG AGA GGG TAA TTT AAA TAT AAA GTT CG (SEQ ID NO: 26) and ATT AAG CTT CTT AGC GGG CCC CTT TAT TAA CGC T (SEQ ID NO: 27). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:26 and/or SEQ ID NO: 27 is used to clone a gene encoding a polypeptide having p-hydroxybenzoate decarboxylase activity (e.g., kpdBCD).

In certain embodiments, the gene encoding a polypeptide having p-hydroxybenzoate hydroxylase activity is pobA. As described in the Examples, the pobA gene was cloned using two synthetic nucleotide primers containing the following sequences: ATA TCT AGA AGG AGG ATA AAT AAT GAA GAC TCA AGT CGC CAT CAT CG (SEQ ID NO: 28) and TAT AAG CTT TAC TCG ATT TCC TCG TAG GGC (SEQ ID NO: 29). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:28 and/or SEQ ID NO: 29 is used to clone a gene encoding a polypeptide having p-hydroxybenzoate hydroxylase activity (e.g., pobA).

In certain embodiments, the gene encoding a polypeptide having protocatechuate decarboxylase activity is aroY. As described in the Examples, the aroY gene was cloned using two synthetic nucleotide primers containing the following sequences: ATA AAG CTT AGG AGG ATA AAT AAT GAC CGC ACC GAT TC (SEQ ID NO: 30) and ATT CTC GAG TTA TTT TGC GCT ACC CTG GTT TTT TTC CAG C (SEQ ID NO: 31 Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:30 and/or SEQ ID NO: 31 is used to clone a gene encoding a polypeptide having protocatechuate decarboxylase activity (e.g., aroY).

In certain embodiments, the gene encoding a polypeptide having 3-dehydroshikimate dehydratase activity is qsuB. As described in the Examples, the qsuB gene was cloned using two synthetic nucleotide primers containing the following sequences: ATA GGA TCC AGG AGG ATA AAT AAT GCG TAC ATC CAT TGC CAC TGT TTG (SEQ ID NO: 32) and ATT AAG CTT CTA GTT TGG GAT TCC CCG CTC GA (SEQ ID NO: 33). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:32 and/or SEQ ID NO: 33 is used to clone a gene encoding a polypeptide having 3-dehydroshikimate dehydratase activity (e.g., qsuB).

As described herein, multiple genes may be cloned and expressed in a single host organism for use in the methods described herein. These genes may be expressed using separate vectors or the same vector. Described below are primers used to generate a gene series for expression in a single vector. Also discussed below are various synthetic plasmid backbones, which comprise multiple elements and primers used to clone such series are described.

In certain embodiments, a gene series encoding polypeptides having chorismate synthase, 3-phosphoshikimate 1-carboxyvinyltransferase and shikimate kinase activities is composed of aroC-aroA-aroL. As described in the Examples, the aroC-aroA-aroL gene series was cloned using Gibson Assembly with two synthetic nucleotide primers containing the following sequences: AGA TCT AAA GGA GGC CAT CCA TGG CTG GAA ACA CAA TTG G (SEQ ID NO: 34) and ATG CCT GGA GAT CCT TAC TCG AGT TTG GAT CCT C (SEQ ID NO: 35). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:34 and/or SEQ ID NO: 35 is used to clone a gene encoding a series of polypeptides having 3-phosphoshikimate 1-carboxyvinyltransferase, and shikimate kinase activities.

In certain embodiments, DNA encoding a synthetic plasmid backbone is composed of p15A ori, lacI repressor, lacUV5 promoter, and Ampicillin resistance marker. As described in the Examples, said series was cloned using Gibson Assembly with two synthetic nucleotide primers containing the following sequences: GAG GAT CCA AAC TCG AGT AAG GAT CTC CAG GCA T (SEQ ID NO: 36) and CCA ATT GTG TTT CCA GCC ATG GAT GGC CTC CTT TAG ATC T (SEQ ID NO: 37). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:36 and/or SEQ ID NO: 37 is used to clone the above described plasmid backbone.

In certain embodiments, DNA encoding a synthetic plasmid backbone is composed of p15A ori, lacI repressor, lacUV5 promoter, and Ampicillin resistance marker. As described in the Examples, said series was cloned using Gibson Assembly with two synthetic nucleotide primers containing the following sequences: CTG CAC GCT TTG ACT ATA TCT AAG GAT CCA AAC TCG AGT AAG G (SEQ ID NO: 38) and CAT GGA TGG CCT CCT AGA TCT TTT GAA TTC TGA AAT TGT TAT C (SEQ ID NO: 39). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:38 and/or SEQ ID NO: 39 is used to clone a the above described plasmid backbone.

In certain embodiments, the gene encoding feedback resistant chorismate mutase/prephenate dehydrogenase activity is composed of tyr$A^{fbr}$. As described in the Examples, tyr$A^{fbr}$ was cloned using Gibson Assembly with two synthetic nucleotide primers containing the following sequences: GAT AAC AAT TTC AGA ATT CAA AAG ATC TAG GAG GCC ATC CAT G (SEQ ID NO: 40) and CGG ATA ATT CAT TAT TTA TCC TCC TTT AGA TCC TTA CTG GCG ATT (SEQ ID NO: 41). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:40 and/or SEQ ID NO: 41 is used to clone a polypeptide displaying chorismate mutase/prephenate dehydrogenase activity.

In certain embodiments, the gene encoding tyrosine phenol lyase activity is composed of tutA. As described in the Examples, tutA was cloned using Gibson Assembly with two synthetic nucleotide primers containing the following sequences: AAT CGC CAG TAA GGA TCT AAA GGA GGA TAA ATA ATG AAT TAT CCG (SEQ ID NO: 42) and CCT TAC TCG AGT TTG GAT CCT TAG ATA TAG TCA AAG CGT GCA G (SEQ ID NO: 43). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:42 and/or SEQ ID NO: 43 is used to clone a polypeptide displaying tyrosine phenol lyase activity.

In certain embodiments, the gene series encoding polypeptides having salicylate decarboxylase, isochorismate pyruvate lyase, and isochorismate synthase activities is composed of SDC-pchB-entC. As described in the Examples, the SDC-pchB-entC gene series was cloned using Gibson Assembly with two synthetic nucleotide primers containing the following sequences: AAG GAG GCC ATC CAT GCG TGG TAA AGT TAG C (SEQ ID NO: 44) and GTT TGG ATC CTT AAT GCA ATC CAA AAA CG (SEQ ID NO: 45). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:44 and/or SEQ ID NO: 45 is used to clone a gene series encoding polypeptides having salicylate decarboxylase, isochorismate pyruvate lyase, and isochorismate synthase activities.

In certain embodiments, DNA encoding a synthetic plasmid backbone is composed of pBBR1 ori, lacI repressor, lacUV5 promoter, and Chloramphenicol resistance marker. As described in the Examples, said series was cloned using Gibson Assembly with two synthetic nucleotide primers containing the following sequences: ATT GCA TTA AGG ATC CAA ACT CGA GTA AG (SEQ ID NO: 46) and CTT TAC CAC GCA TGG ATG GCC TCC TTT AGA TC (SEQ ID NO: 47). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:46 and/or SEQ ID NO: 47 is used to clone the above described plasmid backbone.

In certain embodiments, DNA encoding a polypeptide having kanamycin resistance in place of chorismate mutase/prephenate dehydrogenase activity is composed of ΔpheA::FRT-Kan$^R$-FRT. As described in the Examples, the ΔpheA::FRT-Kan$^R$-FRT DNA cassette was cloned using two synthetic nucleotide primers containing the following sequences: CGT GTG AAA CAG AAT GCG AAG ACG AAC AAT A (SEQ ID NO: 48) and TAA TCC AGT GCC GGA TGA TTC ACA TCA TC (SEQ ID NO: 49). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:48 and/or SEQ ID NO: 49 is used to clone a DNA cassette encoding ΔpheA::FRT-Kan$^R$-FRT.

In certain embodiments, DNA encoding a polypeptide having kanamycin resistance in place of pyruvate kinase II activity is composed of ΔpykA::FRT-Kan$^R$-FRT. As described in the Examples, the ΔpykA::FRT-Kan$^R$-FRT DNA cassette was cloned using two synthetic nucleotide primers containing the following sequences: ATC GCG GCG TTA TTT CAT TCG GAT T (SEQ ID NO: 50) and AAC TGT AGG CCG GAT GTG GC (SEQ ID NO: 51). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:50 and/or SEQ ID NO: 51 is used to clone a DNA cassette encoding ΔpykA::FRT-Kan$^R$-FRT.

In certain embodiments, DNA encoding a polypeptide having kanamycin resistance in place of pyruvate kinase activity is composed of ΔpykF::FRT-Kan$^R$-FRT. As described in the Examples, the ΔpykF::FRT-Kan$^R$-FRT DNA cassette was cloned using two synthetic nucleotide primers containing the following sequences: GCG AGG CAC CAC CAC TTT CG (SEQ ID NO: 52) and AGC GCC CAT CAG GGC G (SEQ ID NO: 53). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:52 and/or SEQ ID NO: 53 is used to clone a DNA cassette encoding ΔpykF::FRT-Kan$^R$-FRT In certain embodiments, the DNA encoding a polypeptide having kanamycin resistance in place of IIA$^{glc}$ activity is composed of Δcrr::FRT-Kan$^R$-FRT. As described in the Examples, the Δcrr::FRT-Kan$^R$-FRT DNA cassette was cloned using two synthetic nucleotide primers containing the following sequences: CTA TGA GCG CCA TTT CTA TCC CGC GC (SEQ ID NO: 54) and CCT GAA AGG GAC TGG CGA CCT G (SEQ ID NO: 55). Accordingly, in certain embodiments, at least one synthetic oligonucleotide primer comprising/consisting of a sequence having at least about 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:54 and/or SEQ ID NO: 55 is used to clone a DNA cassette encoding Δcrr::FRT-Kan$^R$-FRT.

Exemplary Recombinant Host Cells, Compositions and Kits According to One or More Embodiments Certain embodiments provide an expression cassette described herein. In certain embodiments, the expression cassette further comprises one or more promoters. In certain embodiments, the expression cassette further comprises one or more regulatory elements.

Certain embodiments provide a vector described herein (e.g., a plasmid described herein, such as in the Examples, Figures or Tables).

Certain embodiments provide a synthetic oligonucleotide primer described herein.

Certain embodiments provide a recombinant host cell as described herein (e.g., as described in the Examples, Figures or Tables).

In certain embodiments, the recombinant host cell is *Escherichia coli*. In certain embodiments, the recombinant host cell is *E. coli* NST74, *E. coli* NST74 ΔpheA, *E. coli* NST74 ΔpheA ΔpykA ΔpykF, or *E. coli* NST74 ΔpheA ΔpykA ΔpykF Δcrr.

In certain embodiments, the recombinant host cell comprises a plasmid combination selected from the group consisting of: pY3 and pTutA-pPh (CAT2); pSDC-PchB-EntC and pPh (CAT3); pUbiC-Kpd and pPh (CAT4); pUbiC-PobA and pAroY (CAT5); pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA; pQsuB-AroY-CatA (MAF); pTyrAfbr-TutA (PHI); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); and pTyrAfbr-TutA, pSDC-PchB-EntC, and pUbiC-Kpd (PHF4).

In certain embodiments, the recombinant host cell is *E. coli* NST74 ΔpheA and comprises a plasmid combination selected from the group consisting of: pY3 and pTutA-pPh (CAT2); pSDC-PchB-EntC and pPh (CAT3); pUbiC-Kpd and pPh (CAT4); and pUbiC-PobA and pAroY (CAT5).

In certain embodiments, the recombinant host cell is *E. coli* NST74 ΔpheA and comprises a plasmid combination selected from the group consisting of: pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA and pQsuB-AroY-CatA (MAF).

In certain embodiments, the recombinant host cell is *E. coli* NST74 ΔpheA ΔpykA ΔpykF and comprises a plasmid combination selected from the group consisting of: pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA and pQsuB-AroY-CatA (MAF).

In certain embodiments, the recombinant host cell is *E. coli* NST74 ΔpheA ΔpykA ΔpykF Δcrr and comprises a plasmid combination selected from the group consisting of: pQsuB-AroY-CatA (MA1); pY3 and pTutA-pPh-CatA (MA2); pSDC-PchB-EntC and pPh-CatA (MA3); pUbiC-Kpd and pPh-CatA (MA4); pUbiC-PobA and pAroY-CatA (MA5); and pUbiC-PobA and pQsuB-AroY-CatA (MAF).

In certain embodiments, the recombinant host cell is *E. coli* NST74 ΔpheA ΔpykA ΔpykF Δcrr and comprises a plasmid combination pQsuB-AroY-CatA (MA1).

In certain embodiments, the recombinant host cell is *E. coli* NST74 ΔpheA ΔpykA ΔpykF Δcrr and comprises a plasmid combination pUbiC-PobA and pQsuB-AroY-CatA (MAF).

In certain embodiments, the recombinant host cell is *E. coli* NST74 ΔpheA ΔpykA ΔpykF Δcrr and comprises a plasmid combination selected from the group consisting of: pTyrAfbr-TutA (PH1); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); and pTyrAfbr-TutA, pSDC-PchB-EntC, and pUbiC-Kpd (PHF4).

In certain embodiments, the recombinant host cell is *E. coli* NST74 ΔpheA and comprises a plasmid combination selected from the group consisting of: pTyrAfbr-TutA (PH1); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); and pTyrAfbr-TutA, pSDC-PchB-EntC, and pUbiC-Kpd (PHF4).

Certain embodiments provide a composition comprising a recombinant host cell described herein and a carrier. In certain embodiments, the composition further comprises a growth supplement (growth media or broth).

Further provided are kits for practicing the present methods. For example, certain embodiments provide a kit comprising a recombinant host cell described herein and instructions for generating a biochemical product using the recombinant cell (e.g., instructions to practice a method described herein).

Certain Definitions

The term "isochorismate synthase activity" refers to the ability of a protein to catalyze the direct conversion of chorismate to isochorismate.

The term "isochorismate pyruvate lyase activity" refers to the ability of a protein to catalyze the direct conversion of isochorismate to salicylate.

The term "salicylate decarboxylase activity" refers to the ability of a protein to catalyze the direct conversion of salicylate to phenol.

The term "phenol 2-monooxygenase activity" refers to the ability of a protein to catalyze the direct conversion of phenol to catechol.

The term "catechol-1,2-dioxygenase activity" refers to the ability of a protein to catalyze the direct conversion of catechol to cis,cis-muconic acid.

The term "tyrosine phenol lyase activity" refers to the ability of a protein to catalyze the direct conversion of tyrosine to phenol.

The term "chorismate lyase activity" or "chorismate pyruvate lyase activity" refers to the ability of a protein to catalyze the direct conversion of chorismate to p-hydroxybenzoate.

The term "p-hydroxybenzoate decarboxylase activity" refers to the ability of a protein to catalyze the direct conversion of p-hydroxybenzoate to phenol.

The term "p-hydroxybenzoate hydroxylase activity" refers to the ability of a protein to catalyze the direct conversion of p-hydroxybenzoate to protocatechuate.

The term "protocatechuate decarboxylase activity" refers to the ability of a protein to catalyze the direct conversion of protocatechuate to catechol.

The term "3-dehydroshikimate dehydratase activity" refers to the ability of a protein to catalyze the direct conversion of 3-dehydroshikimate to protocatechuate.

The term "chorismate mutase activity" refers to the ability of a protein to catalyze the direct conversion of chorismate to prephenate.

The term "prephenate dehydrogenase activity" refers to the ability of a protein to catalyze the direct conversion of prephenate to 4-hydroxy-phenylpyruvate.

The term "3-DHS" refers to 3-dehydroshikimate.

The term "PCA" refers to protocatechuate.

The term "Phe" refers to L-phenylalanine.

The term "Tyr" refers to L-tyrosine.

The term "Trp" refers to L-tryptophan.

The term "pHBA" refers to p-hydroxybenzoate.

The term "PCA" refers to protocatechuate.

The term "MA" refers to muconic acid.

The term "1,2,3-THB" refers to 1,2,3-trihydroxybenzene.

The term "CDO" refers to catechol-1,2-dioxygenase.

The term "PH" refers to phenol hydroxylase.

The term "TPL" refers to tyrosine phenol lyase.

The term "ToMo" refers to toluene/o-xylene monooxygenase.

The term "host" or "recombinant host" refers any organism (e.g., microorganism or plant) or suitable cell line, such as a strain of bacteria, for example, into which genes can be transferred to impart desired genetic attributes and functions.

The term "recombinant pathway" refers to a pathway that has been modified using recombinant techniques (e.g., the pathway comprises a recombinant protein that is not endogenously expressed by the host).

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment, when it is linked to other sequences for expression, is meant a sequence having, e.g., at least about 80 nucleotides, at least about 150 nucleotides, or at least about 400 nucleotides. If not employed for expressing, a "portion" or "fragment" means, e.g., at least about 9, at least about 12, at least about 15, or at least about 20, consecutive nucleotides, e.g., probes and primers (oligonucleotides), corresponding to the nucleotide sequence of the nucleic acid molecules described herein.

The terms "protein," "peptide" and "polypeptide" are used interchangeably herein.

Isolated or substantially purified nucleic acid or protein compositions are also described herein. An "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When a protein, or biologically active portion thereof, is recombinantly produced, culture medium may represent, e.g., less than about 30%, 20%, 10%, or 5% (by dry weight) of chemical precursors or non-protein-of-interest chemicals. Fragments and variants of the disclosed nucleotide sequences and proteins or partial-length proteins encoded thereby are also described herein. By "fragment" or "portion" is meant a full length or less than full length of the nucleotide sequence encoding, or the amino acid sequence of, a polypeptide or protein.

"Naturally occurring" or "wildtype" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants will have, e.g., at least about 40, 50 or 60 to 70%, or e.g., about 71%, 72%, 73%, 74%, 75%, 76%, 77%, or 78% to 79% or generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance, the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press (3rd edition, 2001).

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons. "Native gene" or "wild type gene" refers to a gene as found in nature with its own regulatory sequences. "Endogenous gene" refers to a native gene in its natural location in the genome of an organism. "Foreign gene or heterologous gene" refers to a gene not normally found in the host organism but that is introduced into the host organism by gene transfer. Foreign genes can comprise native genes inserted into a non-native organism, or chimeric genes.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Genome" refers to the complete genetic material of an organism.

A "vector" is defined to include, inter alia, any viral vector, plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences may include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al. (1995) Mol. Biotech. 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein. "Overexpression" refers to the production of a gene product in a transgenic organism that exceeds levels of production in the wild-type host or native organisms.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

Comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration may be increased so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M (e.g, about 0.01 to 1.0 M), Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 MNaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result form, for example, genetic polymorphism or from human manipulation. Methods for such manipulations are generally known in the art.

Thus, the polypeptides described herein may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, may be used.

Thus, the genes and nucleotide sequences include both the naturally occurring sequences as well as mutant forms. Likewise, polypeptides encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic", "recombinant" or "transformed" cells, and organisms comprising transgenic cells are referred to as "transgenic", "recombinant" or "transformed" organisms.

"Transformed," "transgenic," "transduced" and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

The term "endogenous metabolite" refers to a native metabolite naturally present in a cell/organism.

Certain embodiments will now be illustrated by the following non-limiting Examples.

Example 1. Engineering Novel Pathways and a Synthetic Metabolic Funnel to Enhance Muconic Acid Biosynthesis Multiple alternative MA biosynthesis pathways have to date been engineered, each involving different enzyme chemistries and, most notably, stemming from precursors further downstream in the shikimic acid pathway, thereby preserving chorismate biosynthesis. To date, no fewer than four alternatives pathways have so far been proposed and/or developed for MA biosynthesis from glucose (Averesch, et al., 2014. Metabolic Engineering Communications. 1, 19-28). For example, Sun et al. recently reported a novel MA biosynthesis pathway utilizing anthranilate (intermediate to Trp) as its immediate endogenous precursor (Sun, et al., 2013b. Applied and environmental microbiology. 79, 4024-30). By said pathway, MA titers of 0.39 g/L were achieved using a mixed glucose/glycerol minimal media (supplemented with Trp to account for deletion of trpD) in shake flask cultures. The same group also later engineered another alternative MA pathway, in this case utilizing endogenous 2,3-DHB as its immediate endogenous precursor (Sun, et al., 2014. ChemSusChem. 7, 2478-81). In this case, MA titers of 0.48 g/L were reported using a glucose/glycerol media with yeast extract in shake flasks cultures. Most recently, the same group has engineered a third, alternative MA pathway that instead stems directly from chorismate and proceeds via the key intermediates isochorismate and salicylate (Lin, et al., 2014. Metabolic engineering. 23). Said pathway resulted in MA titers reaching 1.45 g/L in shake flask cultures using the same glucose/glycerol media with yeast extract (in this case to account for Phe and Tyr auxotrophies caused by deletion of pheA and tyrA, respectively, to increase chorismate availability).

In this example, the development of a series of additional, alternative strategies is reported for MA biosynthesis by: i) constructing a series of modular, phenol-derived catechol and MA pathways by linking three recently-engineered phenol biosynthesis pathways (Thompson, et al., 2016. Biotechnol Bioeng. 113(8), 1745-54) with its subsequent, partial aerobic degradation; ii) engineering a four-step MA pathway from endogenous chorismate via the intermediates pHBA, PCA, and catechol; and, iii) exploring a synthetic 'metabolic funnel' as a novel engineering strategy capable of enhancing MA production via the parallel co-expression of two distinct yet converging MA pathways. All five of the proposed strategies importantly circumvent the auxotrophic limitations experienced via the original, '3DHS-derived' route, while by using a synthetic 'metabolic funnel' it is demonstrated how MA titers and yields can be improved relative to single pathway controls.

Materials and Methods

Strains and Media

All strains used in this study are listed in Table 1. *E. coli* NEB10-beta (New England Biolabs (NEB); Ipswich, Mass.) was used for all cloning and plasmid maintenance. *E. coli* NST74 (ATCC 31884) was obtained from the American Type Culture Collection (ATCC; Manassas, Va.) and served as the parent strain in this study. *E. coli* JW2580-1, JW1843-2, JW1666-3, and JW2410-1 were obtained from the *Coli* Genetic Stock Center (CGSC; New Haven, Conn.) and served as the genetic source for the pheA::$Kan^R$, pykA::$Kan^R$, pykF::$Kan^R$, and crr::$Kan^R$ cassettes, respectively. *E. coli* BW25113 was obtained from the CGSC and served as the genetic source for ubiC and entC. *Citrobacter braakii* (ATCC 29063) was obtained from the ATCC and served as the genetic source for tutA. *Klebsiella pneumoniae* PZH572 (ATCC 25955) was obtained from the ATCC and served as the genetic source of kpdBCD and aroY. *Pseudomonas aeruginosa* PAO1 (DSMZ 22644) was obtained from the Leibniz Institute German Collection of Microorganisms and Cell Cultures and served as the genetic source of pobA and pchB. *P. stutzeri* OX1 (ATCC BAA-172) was obtained from the ATCC and served as the genetic source of phKLMNOP *Pseudomonas putida* KT2440 (ATCC 47054) was obtained from the ATCC and served as the genetic source for catA. *Corynebacterium glutamicum* (ATCC 13032) was obtained from the ATCC and served as the genetic source of qsuB.

Seed cultures of *E. coli* strains were cultured in Luria-Bertani (LB) broth at 32° C. and supplemented with 100 mg/L ampicillin and/or 35 mg/L kanamycin, as appropriate. For catechol and MA biosynthesis, shake flasks were cultured at 32° C. in M9M minimal media supplemented with appropriate antibiotics. M9M was composed of the following (in g/L): $Na_2HPO_4$ (6), $KH_2PO_4$ (3), NaCl (0.5), $NH_4Cl$ (2), $MgSO_4.7H_2O$ (0.493), $CaCl_2.2H_2O$ (0.0147), and glucose (20). Trace elements were supplemented as follows (in mg/L): $(NH_4)_6Mo_7O_{24}.4H_2O$ (0.37), $H_3BO_3$ (2.5), $CoCl_2.6H_2O$ (0.714), $CuSO_4$ (0.16), $MnCl_2.4H_2O$ (1.6), $ZnSO_4.7H_2O$ (0.288), $FeCl_3$ (0.05).

Plasmid Construction

All plasmids used and developed in this study are listed in Table 1. All genes were PCR amplified with Q5 High-Fidelity DNA Polymerase (NEB) and a BioRad iCycler, according to manufacturer protocols. Custom DNA oligonucleotide primers were synthesized by Integrated DNA Technologies (IDT, Coralville Iowa) and are listed in Table 2. Genomic DNA (gDNA) templates were prepared using the ZR Fungal/Bacterial DNA MiniPrep kit while plasmid DNA was purified using the Zymo Plasmid MiniPrep kit (both Zymo Research, Irvine Calif.). Amplified linear DNA fragments were purified using the Zymo DNA Clean & Concentrator MiniPrep kit (Zymo Research). Purified linear DNA and plasmid DNA were digested using appropriate restriction endonucleases (NEB) and subsequently gel purified using the Zymoclean Gel DNA Recovery MiniPrep kit (Zymo Research). Purified digested DNA fragments were ligated using T4 DNA Ligase (NEB), per manufacturer protocols. Ligation reactions were transformed into chemically competent *E. coli* NEB10-beta before plating on LB solid agar media supplemented with appropriate antibiotics for selection. Transformant pools were screened using colony PCR, restriction digest mapping, and finally confirmed by DNA sequencing.

Strain Construction

Chromosomal in-frame deletions of pheA, pykA, pykF, and crr in *E. coli* NST74 were individually performed using a modified version of the Datsenko and Wanner method (Datsenko, K. A., Wanner, B. L., 2000. et al., Proc Natl Acad Sci USA. 97, 6640-5), as previously described (Pugh, et al., 2014. Process Biochemistry. 49, 1843-1850). The pheA::FRT-$kan^R$-FRT, pykA::FRT-$kan^R$-FRT, pykF::FRT-$kan^R$-FRT, and crr::FRT-$kan^R$-FRT deletion cassettes were individually PCR amplified from *E. coli* JW2580-1, JW1843-2, JW1666-3, and JW2410-1, respectfully. Chromosomal integration of said cassettes and subsequent removal of $kan^R$ markers was achieved as previously described (Datsenko, K. A., Wanner, B. L., 2000. et al., Proc Natl Acad Sci USA. 97, 6640-5; Pugh, et al., 2014. Process Biochemistry. 49, 1843-1850), resulting in the individual construction of *E. coli* NST74 ΔpheA, *E. coli* NST74 ΔpheA ΔpykA ΔpykF, and *E. coli* NST74 ΔpheA ΔpykA ΔpykF Δcrr.

For catechol biosynthesis, *E. coli* NST74 ΔpheA was co-transformed with the following combinations of plasmids (note: pathway designation provided in parentheses, see Table 1): pY3 and pTutA-pPh (CAT2), pSDC-PchB-EntC and pPh (CAT3), pUbiC-Kpd and pPh (CAT4), and pUbiC-PobA and pAroY (CAT5). For MA biosynthesis, *E. coli* NST74 ΔpheA, NST74 ΔpheA ΔpykA ΔpykF, and NST74 ΔpheA ΔpykA ΔpykF Δcrr were each co-transformed with the following combinations of plasmids: pQsuB-AroY-CatA (MA1), pY3 and pTutA-pPh-CatA (MA2), pSDC-PchB-EntC and pPh-CatA (MA3), pUbiC-Kpd and pPh-CatA (MA4), pUbiC-PobA and pAroY-CatA (MA5), and pUbiC-PobA and pQsuB-AroY-CatA (MAF).

Thermodynamic and Elementary Flux Mode (EFM) Analysis

To compare relative pathway energetics, net changes in Gibbs free energy due to reaction, $\Delta_r G'^{o}_{net}$, were calculated using eQuilibrator (http://equilibrator.weizmann.ac.il) at a reference state of 25° C., pH 7, and ionic strength of 0.1 M. Elementary flux modes (EFMs) were computed in MATLAB R2014b (MathWorks, Natick Mass.) using EFMTool 4.7.1 (Terzer, M., Stelling, J., 2008. Bioinformatics. 24, 2229-35). An *E. coli* stoichiometric network originally employed to compare different phenol biosynthesis pathways (Thompson, et al., 2016. Biotechnol Bioeng. 113(8), 1745-54) and originally adapted from Averesch and Krömer (Metabolic Engineering Communications. 1, 19-28 (2014)), was used to compare relative maximum yields from the various MA pathways and strains of interest in this study.

Assaying Phenol Hydroxylase and Catechol 1,2-Dioxygenase Activity Using Whole Resting Cells Recombinant activities of phenol hydroxylase and catechol 1,2-dioxygenase were assayed in *E. coli* BW25113 following its transformation with pPh or pPh-CatA. Overnight seed cultures were used to inoculate (1% vol.) 50 mL of LB supplemented with 20 g/L glucose and 35 mg/L kanamycin in 250 mL shake flasks. In addition, the effect of $Fe(NH_4)_2(SO_4)_2$ was also examined via its omission or inclusion at 100 μM. Shake flasks were induced by addition of isopropyl β-D-1-thiogalactopyranoside (IPTG) at a final concentration of 0.4 mM upon reaching an optical density at 600 nm ($OD_{600}$) of 0.7. Culturing continued overnight (~12 h) at 32° C. before cells were then collected by centrifugation at 3,000×g for 5 min. Cell pellets were rinsed twice with pH 6.8 phosphate buffered saline (PBS) before being re-suspended to a final $OD_{600}$ of 4 in PBS supplemented with 0.2 g/L glucose and 1 mM phenol in a 250 mL shake flask. Cultures were subsequently incubated at 32° C. with shaking at 200 RPM for up to 12 hours. Samples were periodically drawn for metabolite quantification via HPLC, as described below.

Catechol and MA Production from Glucose

To investigate the bioproduction of catechol and MA, overnight seed cultures were first prepared in LB and supplemented with 100 mg/L ampicillin and/or 35 mg/L kanamycin and used to inoculate (1% vol) 50 mL of M9M minimal media supplemented with 20 g/L glucose in 250 mL shake flasks (note: the medium was additionally supplemented with 0.1 g/L Phe when using ΔpheA-derived host strains). Shake flask cultures were incubated at 32° C. with shaking at 200 RPM until reaching $OD_{600}$~0.7, at which point IPTG induction was performed at a final concentration of 0.4 mM. Cultures were further incubated for a total of up to 120 h, or until significant sugar consumption was no longer detected. Periodically, samples were drawn to measure cell growth (as $OD_{600}$) sugar and metabolite levels by HPLC analysis, as described below. Prior to centrifugation (i.e., to pellet and remove cells), samples for MA analysis were first diluted 1:10 with methanol, while samples for Tyr analysis were diluted 1:10 with 1 N HCl and incubated at 55° C. for 30 min. All samples were then centrifuged at 11,000×g for 5 min before transferring the supernatant to a glass HPLC vial.

HPLC Metabolite Analysis

Metabolite analysis was performed using a Hewlett Packard 1100 series HPLC system. Separation of Phe, pHBA, PCA, salicylate, phenol, catechol, and MA, was achieved using a reverse-phase Hypersil GOLD aQ C18 column (3 mm×250 mm; Thermo Fisher, Waltham, Mass., USA) operated at 45° C. with an isocratic 0.8 mL/min mobile phase consisting of 85% (vol.) 5 mM $H_2SO_4$ and 15% (vol.) acetonitrile. The eluent was monitored using a diode array detector (DAD) set at 215 nm for Phe, salicylate, PCA, and catechol, 260 nm for pHBA, and 275 nm for phenol and MA. Separation of Tyr was also achieved on Hypersil GOLD aQ C18 column, in this case maintained at 30° C. while using a mobile phase consisting of water (A) and methanol plus 0.1% (vol.) formic acid (B) at a constant flow rate of 0.2 mL/min and the following concentration gradient (all by vol.): 5% B from 0 to 8 min, 5% to 40% B from 8 to 13 min, 40% B from 13 to 16 min, 40 to 5% B from 16 to 21 min, and 5% B from 21 to 31 min. The eluent was monitored using a DAD at 215 nm. Glucose and acetate separation was achieved using an Aminex HPX-87H column (BioRAD, Hercules, Calif.) operated at 35° C. and detected using a refractive index detector (RID). The column was eluted with 5 mM $H_2SO_4$ at a constant flow rate of 0.55 mL/min. In all cases, external standards were prepared and used to provide calibrations for concentration determination.

Mass spectrometry analysis was performed using a Dionex Ultimate 3000 HPLC system (Bruker Daltonics, Billerica, Mass., USA) consisting of a HPG-3400 M pump, WPS 3000 TB autosampler fitted with a 5 μL sample loop, and a FLM-3100B thermostatted column compartment. A Hypersil GOLD aQ C18 column (3 mm×250 mm; Thermo Fisher, Waltham, Mass., USA) was operated at 25° C. with an isocratic 0.2 mL/min mobile phase consisting of 85% (vol.) 5 mM formic acid and 15% (vol.) acetonitrile. Metabolites were detected as negative ions using a Bruker MicrOTOF-Q mass spectrometer with the following settings: Capillary voltage, +4000; end plate offset, −500V; nebulizer gas pressure, 2.0 bar; dry gas flow, 8 L/min; dry gas temperature, 210° C.; Funnels 1 and 2 radio frequency (RF) settings, 200 Vpp, Hexapole RF setting, 150 Vpp; Collision Cell RF setting, 100 Vpp; Quadrupole low mass setting, 55 m/z; Transfer time, 100 μs; Pre Pulse Storage, 7 μs. A Peak Scientific NM30LA nitrogen generator (Peak Scientific Inc., Billerica, Mass., USA) supplied nitrogen for the drying and nebulizer gases.

Results and Discussion

Novel Pathway Identification and Theoretical Comparison

In addition to the original, '3DHS-derived' pathway (steps A, B, C in FIG. 1; hereafter referred to as MA1) (Draths, K. M., Frost, J. W., 1994. et al., Journal of the American Chemical Society. 116, 399-400), as discussed above, several alternative pathway options for MA biosynthesis have since also been developed. Although proceeding from different endogenous metabolites and/or involving alternative enzyme chemistries, catechol always serves as the immediate MA precursor. However, in addition to serving as the ubiquitous MA precursor, catechol is also the first intermediate associated with aerobic phenol catabolism—a degradation pathway common to many soil microbes, including various *Pseudomonas* sp., for example (van Schie, P. M., Young, L. Y., 2000. Bioremediation Journal. 4, 1-18). Accordingly, it was hypothesized that, by linking engineered phenol production with its partial, aerobic degradation, additional new routes to MA could ultimately also be engineered. More specifically, as illustrated in FIG. 1, this could be achieved by further co-expressing phenol hydroxylase (PH) and catechol 1,2-dioxygnease (CDO) (steps K, C; FIG. 1) in a phenol-producing background. Whereas engineered phenol production has traditionally involved expression of tyrosine phenol lyase (TPL; step J) in a Tyr over-producing host (Kim, et al., 2014. Biotechnology journal. 9, 621-9; Wierckx, et al., 2005. Applied and environmental microbiology. 71, 8221-7), the engineering of two alternative phenol biosynthesis pathways from chorismate was recently reported, involving either isochorismate synthase, isochorismate pyruvate lyase, and salicylate decarboxylase (steps G, H, I) or chorismate lyase and pHBA decarboxylase (steps D, F) (Thompson, et al., 2016. Biotechnol Bioeng.

113(8), 1745-54). Accordingly, three novel, phenol-dependent MA biosynthesis pathways were proposed, hereafter referred to as MA2 (steps J, K, C), MA3 (steps G, H, I, K, C), and MA4 (steps D, F, K, C). Meanwhile, in separate works, reported a novel pathway for catechol biosynthesis that proceeds from chorismate through pHBA and PCA via chorismate lyase, pHBA hydroxylase, and PCA decarboxylase (steps D, E, B) was also previously reported (Pugh, et al., 2014. Process Biochemistry. 49, 1843-1850). Accordingly, further extension of this pathway to MA was also proposed, in this case by co-expressing CDO, resulting in pathway MA5 (steps D, E, B, C).

Figure 2:
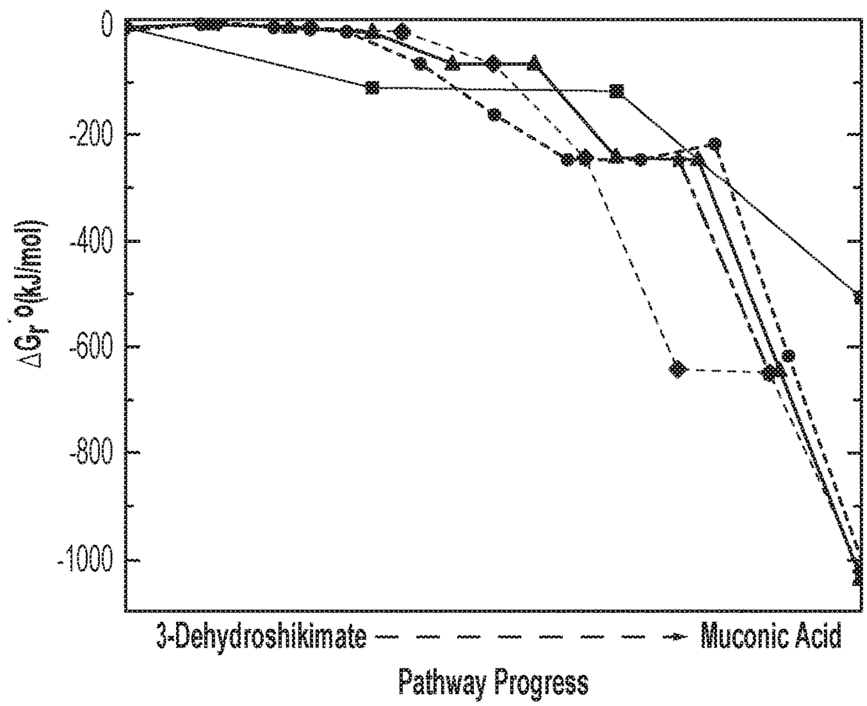
FIG. 2. Comparing the predicted change in Gibbs free energy of reaction) ($\Delta_r G'^{o}$) as a function of pathway progress from 3-DHS (the last common endogenous precursor) to MA for each of the five pathways studied (MA1: squares, MA2: circles, MA3: triangles, MA4: stars, MA5: diamonds). Also compared are the predicted maximum MA yields ($Y_{P/S}$), MA yields with growth ($Y_{P/S+growth}$), and biomass yields ($Y_{X/S}$) from glucose, as determined by elementary flux mode (EFM) analysis. Note: Yields are the fraction of carbons in the substrate (glucose) that end up in the product (MA). PCA: protocatechuate, Tyr: tyrosine, pHBA: p-hydroxybenzoate.

Unlike MA1, the four alternative pathways proposed herein (MA2-5) importantly stem from chorismate or one of its downstream metabolites, and thereby offer improved host compatibility by preserving native flux through the shikimic acid pathway. In addition, relative to MA1, each of MA2-5 was also found to further benefit from an increased net thermodynamic driving force (as much as 104% greater). More specifically, when evaluated from the last common precursor (i.e., 3DHS), the net change in Gibbs free energy due to reaction ($\Delta_r G'^{o}_{net}$) was predicted to be −1037.4 kJ/mol for each of MA3-5 and −1007.6 kJ/mol for MA2, compared to just −508.5 kJ/mol for MA1 (FIG. 2). In contrast, as determined via elementary mode analysis, MA1 supports the highest product yield, with the predicted maximum theoretical yields of MA from glucose ($Y_{P/S,max}$) being ~18% lower (or ~15% lower with growth, $Y_{P/S,max+growth}$; FIG. 2) for each of MA2-5. In all cases, said reduction is due to the additional 1 NADPH (by AroE), 1 ATP (by AroL), and 1 phosphoenolpyruvate (PEP; by AroA) consumed while converting 3DHS to chorismate. Meanwhile, both MA3 and MA4 further require an additional 1 NADH (i.e., by PH; note: this demand is balanced in MA2 by the generation of 1 NADH by TyrA), whereas MA5 requires an additional 1 NADPH (by pHBA hydroxylase). Other previously-reported chorismate-derived MA pathways (i.e., derived from anthranilate or from salicylate, via an alternative mechanism (Lin, et al., 2014. Metabolic engineering. 23; Sun, et al., 2013a. Applied and environmental microbiology. 79)) suffer the same limitations with respect to predicated maximum MA yields from glucose, in this case also being about 17-20% lower than MA1 (or 18-19% lower with growth; note: the anthranilate-derived pathway offers the lowest yield due to a requirement for an additional 1 ATP) (Averesch, et al., 2014. Metabolic Engineering Communications. 1, 19-28). Therefore, despite incorporating more favorable enzyme chemistries and the potential for improved host compatibility, potential improvements associated with the proposed and other MA pathways come at the cost of lower maximum theoretical yields.

Screening for and Characterizing Recombinant Phenol Hydroxylase Activity in *E. coli*

Effective enzyme candidates for most steps associated with each of the proposed pathways have been reported and/or characterized (Lin, et al., 2014. Metabolic engineering. 23; Pugh, et al., 2014. Process Biochemistry. 49, 1843-1850; Thompson, et al., 2016. Biotechnol Bioeng. 113(8), 1745-54). Phenol-dependent MA biosynthesis (i.e. via pathways MA2-4) represents a new approach, however, and first required identification of a candidate gene whose expression would confer recombinant PH activity in *E. coli*. PH activity has been identified as part of bacterial multicomponent monooxygenases (BMMs). BMMs represent a broad class of enzymes capable of using molecular oxygen to hydroxylate various hydrocarbon species, and have been identified to function in numerous microbes as the initial activating steps involved in degrading benzene, toluene, and xylene (Jindrova, et al., 2002. Folia Microbiologica. 47, 83-93; Notomista, et al., 2003. J Mol Evol. 56, 435-45; Sridevi, et al., 2012. Int J Eng Sci Adv Technol. 2, 695-705). Notable examples include toluene/o-xylene monooxygenase (ToMo, encoded by touABCDEF) and phenol hydroxylase (PH, encoded by phKLMNOP), both from *Pseudomonas stutzeri* OX1, which together function to sequentially catalyze the first two steps in benzene degradation (i.e., via phenol then catechol) (Cafaro, et al., 2004. Applied and environmental microbiology. 70, 2211-9; Cafaro, et al., 2002. Eur J Biochem. 269, 5689-99; Tinberg, et al., 2011. Biochemistry. 50, 1788-1798). As promiscuous enzymes, previous in vitro studies have shown that both touABCDEF and phKLMNOP display the desired PH activity; however, phKLMNOP exhibits more favorable activity towards phenol ($K_m$=0.6 μM, $k_{cat}$=1.02 $s^{-1}$), its native substrate, than does touABCDEF ($K_m$=2.18 μM, $k_{cat}$=1.00 $s^{-1}$) (Cafaro, et al., 2004. Applied and environmental microbiology. 70, 2211-9). Accordingly, phKLMNOP was selected as the initial candidate for establishing recombinant PH activity (step K; FIG. 1) in *E. coli*. Meanwhile, whereas CDO activity (step C) has been identified in a variety of aromatic-degrading microorganisms (Bouwer, E. J., Zehnder, A. J., 1993. Trends in biotechnology. 11, 360-7; Cao, et al., 2008. Applied microbiology and biotechnology. 81, 99-107; Kukor, et al., 1988. Journal of Bacteriology. 170, 4458-4465), CatA from *P. putida* displays high recombinant activity (10.10±0.35 μmol/min/mg protein) (Sun, et al., 2013a. Applied and environmental microbiology. 79), and thus was accordingly used in each of MA1-5.

Figure 3:
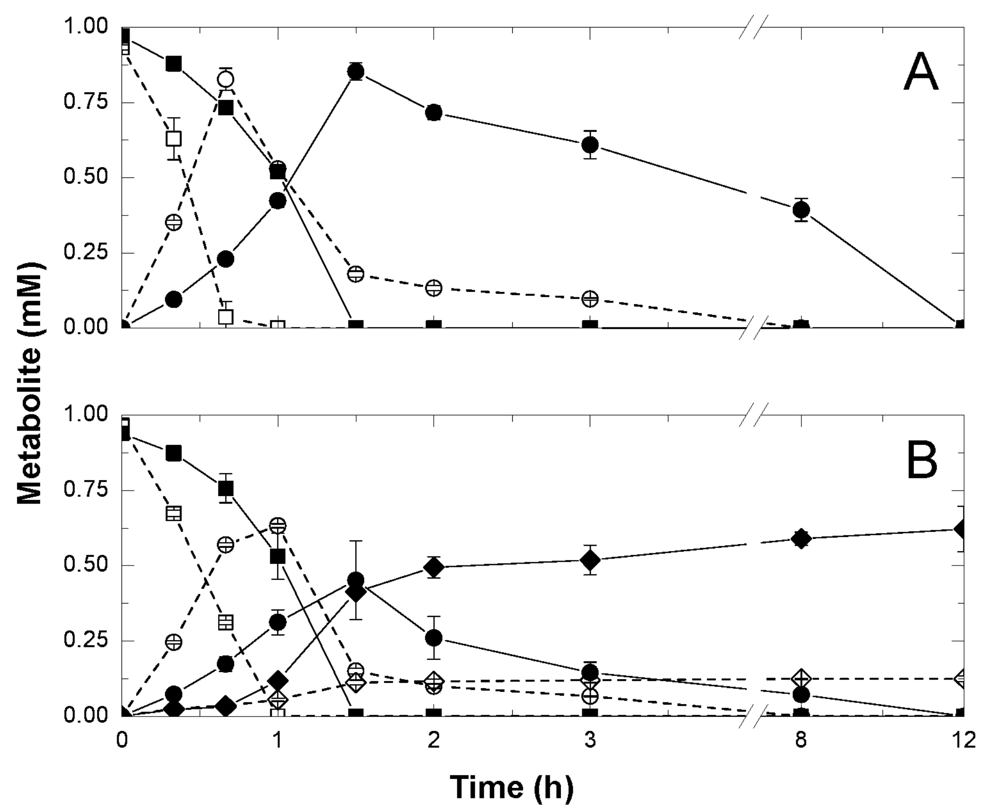
FIGS. 3A-3B. Screening candidate pathway enzymes using whole resting cells supplemented with (dashed lines, open symbols) and without (solid lines, filled symbols) 100 μM $Fe(NH_4)_2(SO_4)_2$ supplementation.
Figure 4:
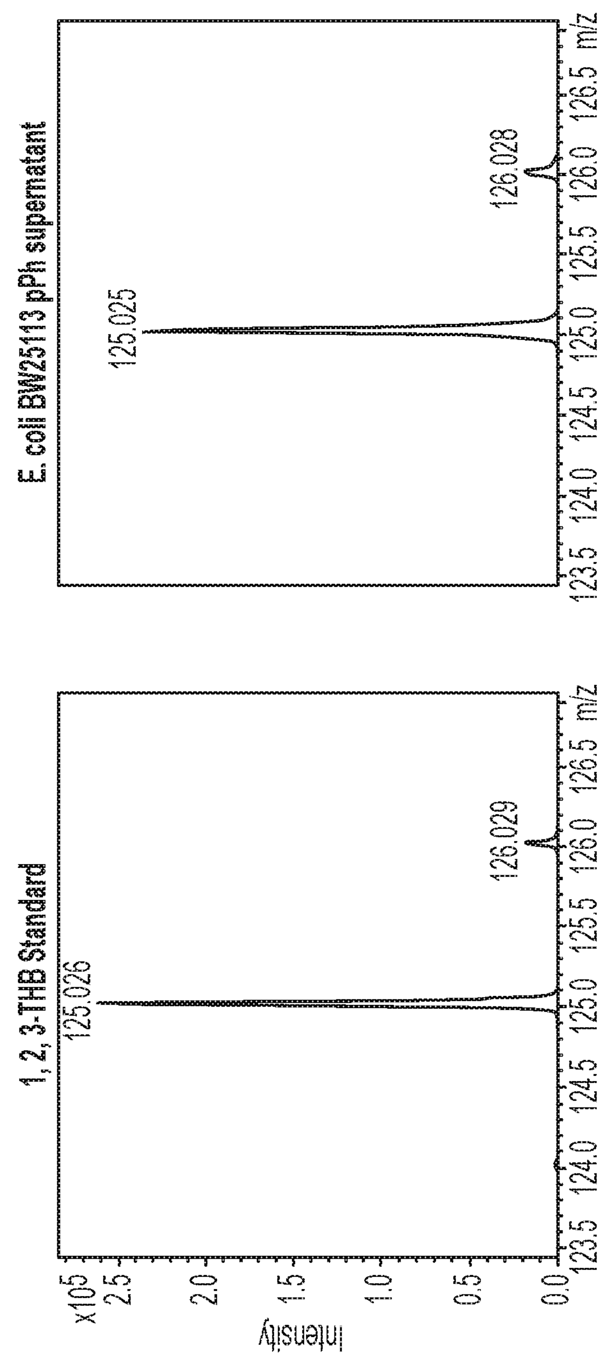
FIG. 4. Detection of 1,2,3-trihydroxybenzene (1,2,3-THB) in culture supernatants from *E. coli* BW25113 whole resting cells expressing phKLMNOP of *Pseudomonas stutzeri* OX1. Cells were suspended in PBS buffer (pH 6.8) supplemented with 1 mM phenol.

Recombinant PH activity was confirmed in vivo via whole resting cell assays employing *E. coli* BW25113 pPh. Because PH possesses carboxylate-bridged diiron catalytic centers in each of its N subunits, as well as a [2Fe-2S] cluster in the P subunit (Cafaro, et al., 2004. Applied and environmental microbiology. 70, 2211-9; Tinberg, et al., 2011. Biochemistry. 50, 1788-1798), the medium was first supplemented with 100 μM $Fe(NH_4)_2(SO_4)_2$. Under these conditions, 1 mM exogenous phenol was rapidly converted to catechol, achieving a maximum specific rate of 0.991 mmol $g^{-1}$ $h^{-1}$ (FIG. 3A). However, after reaching a maximum level of 0.83±0.04 mM after 40 min, catechol levels then gradually decreased over time, ultimately being undetected after 8 h. It was initially hypothesized that the disappearance of catechol was a result of dimer formation, as said phenomena have been reported to occur for various catechols in the presence of excess Fe(III) and under mildly acidic conditions, a process that plays an important role in adhesive formation in the mussel byssus (Fullenkamp, et al., 2014. RSC Advances. 4, 25127-25134). To test this hypothesis, and determine if such an undesirable side reaction could perhaps be avoided, the assay was next repeated without $Fe(NH_4)_2(SO_4)_2$ supplementation (FIG. 3A). Under these conditions, phenol conversion to catechol occurred at a similar yield (0.85±0.03 mM catechol produced from 1 mM phenol after 1.5 h), proceeding, however, at only ~60% of the previous maximum specific rate (just 0.596 mmol $g^{-1}$ $h^{-1}$). However, even in the absence of Fe(III), catechol was again depleted following its formation, here completely disappearing after 12 h. As an alternative hypothesis, several BMMs have been reported to display promiscuous activity towards numerous, related aromatic species, including the repeated hydroxylation of the same initial substrate molecule (Tao, et al., 2004. Applied and environmental microbiology. 70, 3814-20; Vardar, G., Wood, T. K., 2005. Journal of Bacteriology. 187, 1511-1514). Thus, it was postulated that the PH encoded by phKLMNOP might also be capable of further hydroxylating catechol to 1,2,3-trihydroxybenzene (1,2,3-THB). LC-MS analysis was performed on supernatants prepared from the above resting cell assays, wherein an unknown peak was identified with a molar mass (m/z) of 125.03±0.02 (FIG. 4). As the molecular weight of 1,2,3-THB 126.11 g/mol, this strongly suggests that catechol disappearance is occurring due to its further hydroxylation to 1,2,3-THB by PH. Although previously reported for ToMo (Vardar, G., Wood, T. K., 2005. Journal of Bacteriology. 187, 1511-1514), to the best of the inventors' knowledge, this is the first report of such behavior by phKLMNOP from *P. stutzeri* OX1.

For any pathway incorporating PH (i.e., MA2-4), co-production of 1,2,3-THB will likely compete for available catechol, thereby reducing MA production. Accordingly, it was hypothesized that rapid turnover of catechol to MA by CDO might enable the undesirable production of 1,2,3-THB to be minimized upon implementation of the full pathway. As a preliminary test, the above experiment was repeated using whole resting cells of *E. coli* BW25113 pPh-CatA which co-express CDO (encoded by catA from *P. putida* KT2440) together with PH. In this case, as seen in FIG. 3B for both with and without $Fe(NH_4)_2(SO_4)_2$ supplementation, 1 mM phenol was converted to MA at maximum final concentrations of 0.62±0.08 and 0.12±0.01 mM, respectively. Thus, although co-expression of PH and CDO enabled the successful transformation of phenol to MA (which, unlike catechol, stably accumulated for the duration of the experiment; FIG. 3B), overall conversion was low (reaching no greater than 62%) due to the persistent competing formation of 1,2,3-THB by PH.

Investigating Phenol-Dependent Catechol Production in *E. coli*

Three distinct phenol biosynthesis pathways (Thompson, et al., 2016. Biotechnol Bioeng. 113(8), 1745-54) were each next extended to catechol via the additional co-expression of phKLMNOP. This resulted in the construction of three novel catechol production pathways: CAT2 (steps J, K), CAT3 (steps G, H, I, K), and CAT4 (steps D, F, K) (FIG. 1). When expressed in *E. coli* NST74 ΔpheA in shake flask cultures, phenol-dependent catechol biosynthesis from glucose was successfully demonstrated in all three cases, the results of which are compared in Table 3. For each of CAT2-4, however, significant levels of residual phenol remained at the end of each culture (reaching as high as 149±1 mg/L and, in all cases, surpassing total catechol production), suggesting low PH activity as a common bottleneck. In addition, similar to the whole resting cell assays, all three pathways further suffered from the competing formation of 1,2,3-THB, with detected levels reaching as much as 96±4 mg/L. In the case of CAT2, catechol titers reached 79±3 mg/L at a glucose yield of 6.2±0.28 mg/g. In addition to phenol, high levels of unconverted Tyr also accumulated in the medium, reaching 342±12 mg/L after 96 h, pointing to TPL as an additional flux limiting step in the pathway. TPL, for example, is known to suffer from both equilibrium limitations (the reaction is reversible, with $\Delta_r G'^{o}=+27.9$ kJ/mol; FIG. 1) as well as feedback inhibition by phenol (e.g., 94 mg/L phenol reduces TPL activity to only 23% of its maximum (Wierckx, et al., 2008. Journal of bacteriology. 190, 2822-30)). Among the three pathways, CAT3 enabled the highest catechol titer and yield, reaching 100±2 mg/L and 12.8±0.26 mg/g, respectively; however, residual salicylate also accumulated at 55±2 mg/L in this case. Moreover, glucose utilization remained low among all strains, with overall consumption averaging just ~44% (Table 3), the precise reasons for which presently remain unclear. Thus, although functional and enabling phenol-dependent catechol production from glucose for the first time, all three novel catechol pathways (i.e., CAT2-4) suffer from inherent limitations associated with PH, both in terms of low recombinant activity as well as its apparent promiscuity. For comparison, the focal production of catechol via another, chorismate-derived pathway, referred to here as CAT5 (steps D, E, B; FIG. 1) was previously investigated (Pugh, et al., 2014. Process Biochemistry. 49, 1843-1850). When expressed in the same host background and under identical culture conditions, said pathway enabled final catechol titers reaching up to 451±44 mg/L at a glucose yield of 35.0±3.0 mg/g—outputs 4.5- and 2.7-fold greater, respectively, than those achieved by even CAT3—and did so without significant terminal accumulation of any pathway intermediates.

Investigating MA Production Via Newly Engineered Pathways

The relative prospects of MA biosynthesis via the three phenol-dependent pathways (MA2-4) and the previously-reported, chorismate-derived catechol pathway (MA5) were investigated via the additional co-expression of catA from *P. putida* KT2440 (encoding CDO). *E. coli* NST74 ΔpheA was again employed as the initial host background of interest, and the results are compared in Table 4. MA titers by MA2, which proceeds through phenol via Tyr, were lowest, reaching just 186±11 mg/L at a glucose yield of 21.0±2.2 mg/g. As was the case for CAT2, this appears to be due at least in part to flux limitations associated with both TPL and PH, as indicated by the terminal accumulation of as much as 220±12 mg/L Tyr and 63±1 mg/L phenol. Like CAT3, MA3 resulted in the highest MA titers and yields among all phenol-derived pathways (i.e., MA2-4), reaching 484±44 mg/L and 46.7±6.0 mg/g, respectively. However, analogous to the case of catechol production, the common reliance upon PH in each of MA2-4 similarly resulted in production of 1,2,3-THB byproduct in each case, here reaching as high as 232±17 mg/L. Furthermore, similar to CAT2-4, low glucose consumption was also observed for each of MA2-4, again averaging just 44% (Table 4). Meanwhile, perhaps expectedly, MA biosynthesis was highest in the case of MA5, reaching 819±44 mg/L at a yield of 40.9±2.2 mg/g. Lastly, to provide a head-to-head comparison, MA1 (i.e., the original '3DHS-derived' pathway) was also constructed and expressed in the same host background. In this case, MA production reached 1586±11 mg/L at a yield of 79.3±0.53 mg/g. Overall, said results are consistent with the above model predictions that found MA1 to be the highest yield pathway (FIG. 2). Interestingly, and in contrast to the original Draths and Frost study wherein an *E. coli* ΔaroE background was used to promote 3DHS availability (resulting in multiple, undesirable auxotrophies), significant MA production via MA1 was demonstrated here without disrupting the shikimic acid pathway. This suggests that, at least under the present conditions, MA1 is capable of effectively competing against native metabolism for at least significant portion of available 3DHS. Furthermore, it should also be noted that although low PCA decarboxylase activity has been implicated as a limiting factor associated with MA production via MA1 (and here, by extension, perhaps also MA5) (Sonoki, et al., 2014. J Biotechnol. 192 Pt A, 71-7), as PCA remained undetected throughout any of the present cultures (Table 4), such effects do not appear to be limiting for the strains and conditions studied here.

Enhancing MA Production Via Synthetic 'Metabolic Funneling'

Figure 5A:
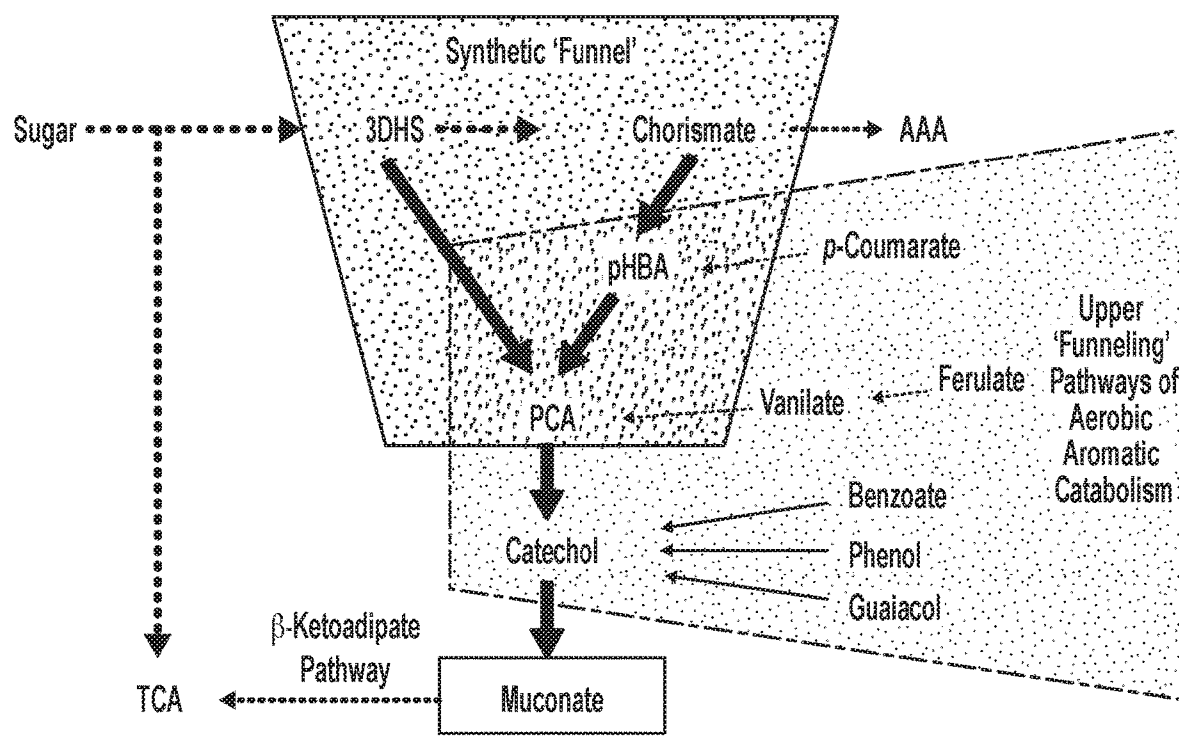
FIGS. 5A-B.
Figure 5B:
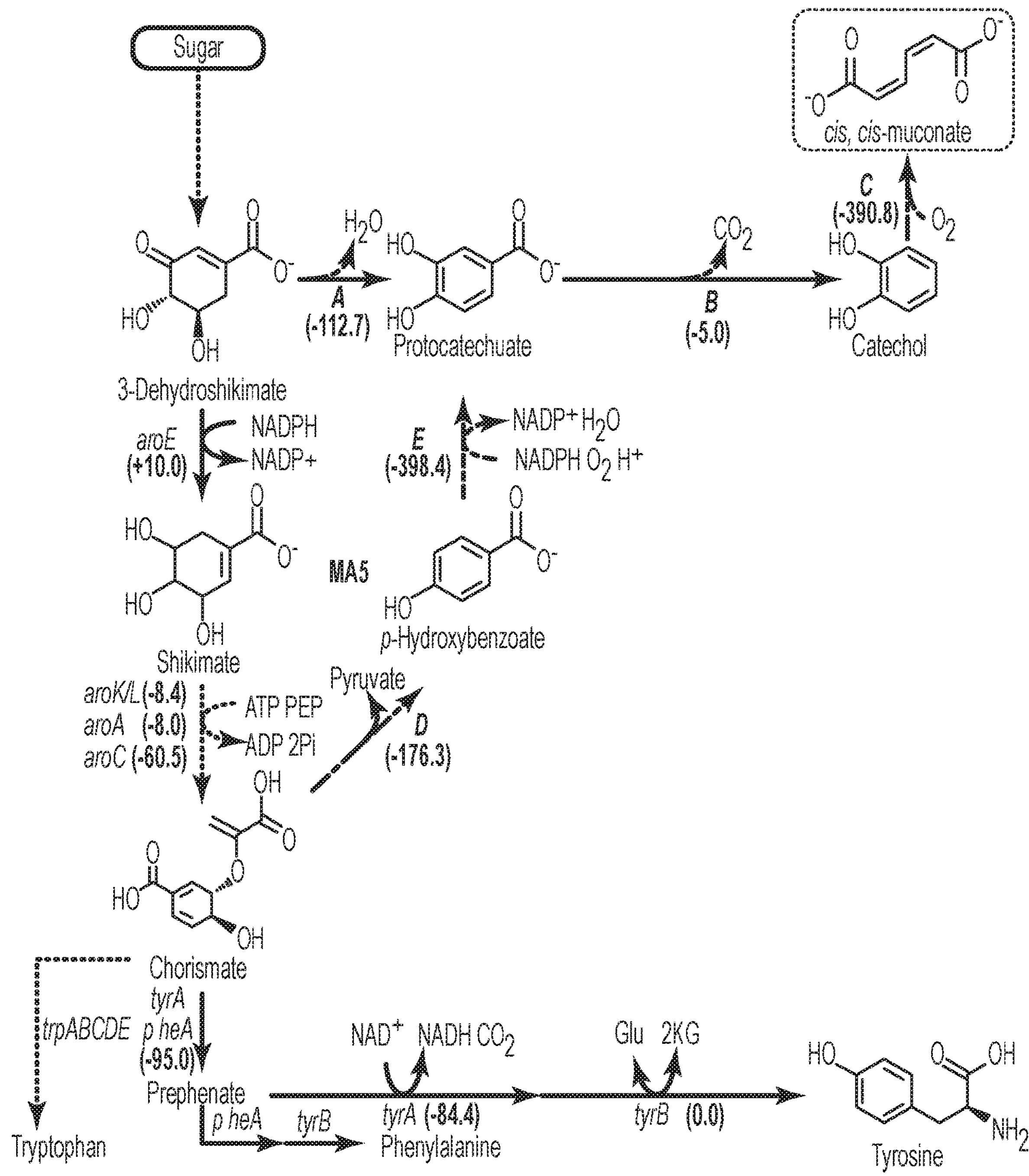

To further improve upon the high production potential of MA1, a synthetic 'metabolic funnel' was next engineered and investigated as a novel strategy for further improving MA biosynthesis. More specifically, an additional 'funneling' pathway, referred to as MAF (steps A, B, C, D, E; FIG. 1), was engineered in this case by co-expressing both MA1 and MA5 together in the same host (FIG. 5). In this way, MA production occurs via two simultaneous and compatible routes: first, via the high yield, '3DHS-derived' pathway (MA1) and, second, via the best-performing, chorismate-derived pathway (MA5)—the latter of which provides an opportunity to 'rescue' additional endogenous precursors not initially 'captured' at first branch point (i.e., at 3DHS). Accordingly, with two routes functioning in parallel, it was proposed that MAF would enable maximal total precursor assimilation towards MA. As with individual MA pathways, MAF was first introduced and expressed in NST74 ΔpheA, resulting in the accumulation of 2042±88 mg/L MA at a glucose yield of 102±4.4 mg/g (Table 4). When compared to MA1, this suggests that as much as an additional 456 mg/L MA (22% of total MA) was produced via the ability of the 'lower branch' (i.e., MA5) to assimilate precursors (in this case, chorismate) not initially taken in via the 'upper branch' (i.e., MA1). Overall, when compared to strains expressing the single, parent pathways (i.e., MA1 or MA5 alone), the combined 'funneling' strategy of MAF resulted in MA titer improvements of 29 and 150%, respectively, and 29 and 132% in terms of achievable yields. Finally, in contrast to each of the phenol-derived pathways (i.e., MA2-4), when employing MA1, MA5, or MAF, all available glucose was consumed within 120 h (Table 4).

Host Engineering to Enhance Precursor Availability and MA Production

To further improve MA production, subsequent culturing and strain engineering efforts were focused on increasing total carbon flux into the shikimic acid pathway and reducing overflow metabolism observed with high glucose uptake rates (Liu, et al., 2014. Process Biochemistry. 49, 751-757). Flux into the shikimic acid pathway is initially controlled by 3-deoxy D-arabinoheptulose 7-phosphate (DAHP) synthase, whose two substrates are phosphoenolpyruvate (PEP) and erythrose 4-phosphate (E4P) (Bongaerts, et al., 2001. Metabolic engineering. 3; Gosset, G., 2009. Current opinion in biotechnology. 20; Rodriguez, et al., 2014. Microb Cell Fact. 13). As has been previously demonstrated (Gosset, G., 2005. Microb Cell Fact. 4, 14; Postma, et al., 1993. Microbiol Rev. 57), increasing the intracellular availability of PEP is an effective strategy for enhancing the production of aromatic amino acids (Liu, et al., 2014. Process Biochemistry. 49, 751-757) and other products from intermediates of the shikimic acid pathway (Noda, et al., 2016. Metabolic engineering. 33, 119-129). In glucose-fed cultures, PEP availability can be increased by blocking its conversion to pyruvate via deletion of pykA and pykF, both of which encode isozymes of pyruvate kinase. Meanwhile, rapid uptake of glucose has been previously reported to result in the accumulation of acetate (Gosset, G., 2005. Microb Cell Fact. 4, 14)—an undesirable byproduct which can ultimately inhibit cell metabolism (Shiloach, et al., 1996. Biotechnol Bioeng. 49, 421-8 et al., 1996) and result in lower aromatic product yields (Liu, et al., 2014. Process Biochemistry. 49, 751-757). As seen in Table 4, for example, significant levels of residual acetate were observed here in all cases, reaching as high as 12 g/L. It has previously been shown, however, that carbohydrate repression resistant null mutants (i.e., Δcrr) display lower rates of glucose uptake and thus reduced overflow metabolism. As a result, this mutation has also been previously demonstrated as effective for enhancing phenylalanine production (Liu, et al., 2014. Process Biochemistry. 49, 751-757). Accordingly, *E coli* NST74 ΔpheA ΔpykA ΔpykF Δcrr was next constructed and evaluated as a MA production host, in this case narrowing the focus to just MA1 and MAF. As seen in Table 5, for MA1, whereas acetate accumulation was effectively eliminated, the additional mutations enabled a modest (~13%) increase in MA production, with final titers reaching 1792±28 mg/L at a glucose yield of 89.6±1.4 mg/g. On the other hand, MA production by MAF was significantly enhanced using *E coli NST*74 ΔpheA ΔpykA ΔpykF Δcrr as host, with final MA titers reaching 3153±149 mg/L at a glucose yield of 158±7.4 mg/g—both increase of over 1.5-fold relative to the use of *E coli* NST74 ΔpheA as host, and the highest production metrics achieved in this study. Furthermore, this maximal titer also is 31% higher than the 2.4 g/L of MA reported by Draths and Frost via MA1 in an *E. coli* ΔaroE background (Draths, K. M., Frost, J. W., 1994. et al., Journal of the American Chemical Society. 116, 399-400), and was notably achieved while generating only a single auxotrophy (i.e., for Phe).

Further comparing the results of Tables 4 and 5, although the apparent flux of precursor through the 'upper branch' (i.e., MA1) was only slightly improved, the 'lower branch' (i.e., MA5) appeared to offer an even greater benefit; in this case enabling the production of as much as an additional 1361 mg/L MA (43% of total MA produced). Accordingly, the additional ΔpykA, ΔpykF, and Δcrr mutations appear to have more greatly improved the intracellular availability of chorismate than that of 3DHS. Interestingly, meanwhile, in the case of MAF, acetate accumulation reemerged, reaching up to 7±0.1 g/L by the end of the culture (Table 5). Unlike MA1, the first step of MA5 (step D; FIG. 1) is catalyzed by chorismate pyruvate lyase (encoded by native ubiC) and results in the generation of 1 pyruvate molecule. While future works will be required to test this hypothesis, it is possible that said pyruvate is then converted to acetyl-CoA and ultimately to acetate via *E. coli*'s phosphate acetyltransferase and acetate/acetyl-CoA pathway (encoded by pta-ackA), providing the cell with 1 ATP in the process. Further host engineering to incorporate additional mutations previously reported as effective for reducing acetate accumulation during aromatic amino acid biosynthesis may also be performed (Castaño-Cerezo, et al., 2009. et al., Microb Cell Fact. 8, 54; Liu, et al., 2016. Plos One. 11, e0158200; Wang, et al., 2013. Applied microbiology and biotechnology. 97, 7587-96; Wolfe, A. J., 2005. Microbiology and Molecular Biology Reviews. 69, 12-50) with the goal of further improving MA production via the demonstrating funneling pathway, MAF.

Figure 6:
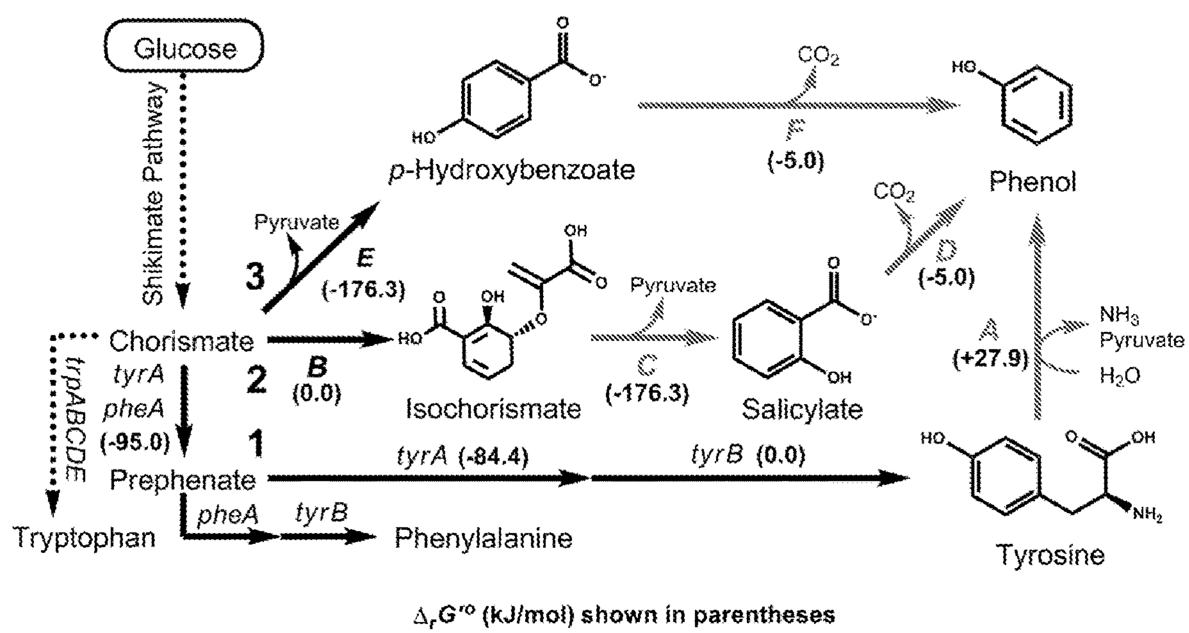
FIG. 6. Three non-natural pathways engineered for phenol production from glucose. Black arrows represent enzyme steps native to *E. coli* whereas gray arrows are heterologous, dotted arrows represent multiple enzymatic steps. $\Delta_r G'^{\circ}$ is the change in Gibbs free energy due to reaction as determined using the online tool eQuilibrator (http://equilibrator-.weizmann.ac.il) at a reference state of 25° C., pH 7, and ionic strength of 0 M. A: tyrosine phenol lyase, B: isochorismate synthase, C: isochorismate pyruvate lyase, D: salicylate decarboxylase, E: chorismate pyruvate lyase, F: p-hydroxybenzoate decarboxylase.
Figure 7:
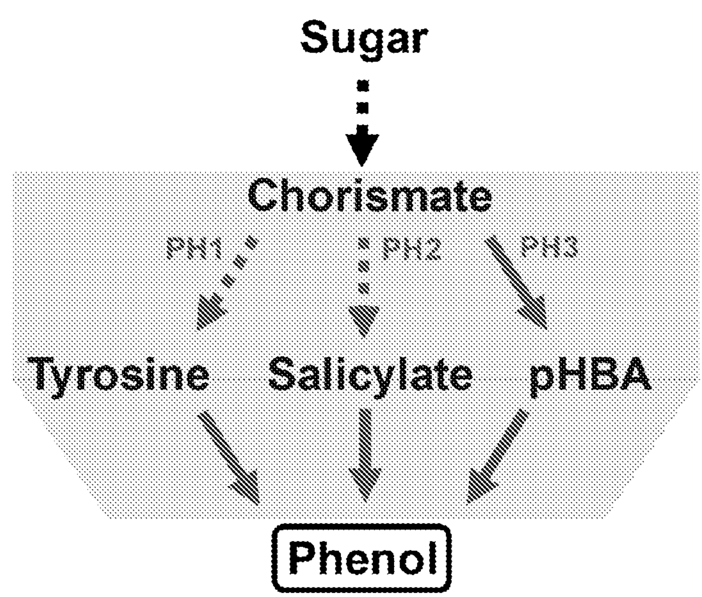
FIG. 7. Engineering a synthetic 'metabolic funnel' for enhanced phenol production. The synthetic 'metabolic funnel' was constructed via the simultaneous co-expression of two or three distinct pathways, all stemming from chorismate as the last common endogenous precursor. Black bold dashed arrow represents multiple enzyme reactions native to *E. coli*; solid arrows represent individual enzyme steps associated with the engineered pathways; pHBA: p-hydroxybenzoate.

Example 2. Engineering Novel Pathways and a Synthetic Metabolic Funnel to Enhance Phenol Biosynthesis Phenol is an important building block molecule used in the synthesis of various specialty chemicals, plastics and polymers of industrial relevance (Adkins, et al., 2012. Frontiers in microbiology. 3, 313; Deng, et al., 2016. Biochem Eng J. 105, 16-26). Although the complete biosynthesis of phenol from glucose has previously been demonstrated, the originally engineered pathway, which proceeds from endogenous tyrosine via tyrosine phenol lyase (TPL) (Wierckx, et al., 2008. Journal of bacteriology. 190, 2822-30; Wierckx, et al., 2005. Applied and environmental microbiology. 71, 8221-7), suffers from notable inherent limitations. Phenol has previously been synthesized from endogenous tyrosine via expression of heterologous tyrosine phenol lyase (TPL) activity (FIG. 6). For instance, although phenol was successfully synthesized in this manner with maximal shake flask titers reaching 141 mg/L (Wierckx, et al., 2005. Applied and environmental microbiology. 71, 8221-7), TPL reaction reversibility and enzymatic feedback inhibition ultimately resulted in poor pathway efficiency and limited production metrics (Kim, et al., 2014. Biotechnology journal. 9, 621-9; Wierckx, et al., 2008. Journal of bacteriology. 190, 2822-30). As an alternative approach, two novel pathways were engineered and comparatively evaluated against the original tyrosine-derived pathway (FIG. 6), both of which instead stem from endogenous chorismate (Thompson, et al., 2016. Biotechnol Bioeng. 113(8), 1745-54). Using these pathways, titers reached as high as 377 mg/L, although overall yields via any phenol pathway remained less than 10% of the theoretical maximum (Thompson, et al., 2016. Biotechnol Bioeng. 113(8), 1745-54). In the present example, a synthetic 'metabolic funnel' was engineered and investigated as a strategy for enhancing phenol production via the parallel co-expression of distinct yet converging biosynthesis pathways (FIG. 7).

Materials and Methods

Strains and Media

All strains used in this study are listed in Table 6. *E. coli* NEB10-beta (New England Biolabs (NEB); Ipswich, Mass.) was used for all cloning and plasmid maintenance. *E. coli* NST74 (ATCC 31884) was obtained from the American Type Culture Collection (ATCC; Manassas, Va.) and served as the parent strain in this study. *E. coli* JW2580-1, JW1843-2, JW1666-3, and JW2410-1 were obtained from the Coli Genetic Stock Center (CGSC; New Haven, Conn.) and served as the genetic source for the pheA::Kan$^R$, pykA::Kan$^R$,pykF::Kan$^R$, and crr::Kan$^R$ cassettes, respectively. *E. coli* BW25113 was obtained from the CGSC and served as the genetic source for ubiC and entC. *Citrobacter braakii* (ATCC 29063) was obtained from the ATCC and served as the genetic source for tutA. *Klebsiella pneumoniae* PZH572 (ATCC 25955) was obtained from the ATCC and served as the genetic source of kpdBCD. *Pseudomonas aeruginosa* PAO1 (DSMZ 22644) was obtained from the Leibniz Institute German Collection of Microorganisms and Cell Cultures and served as the genetic source of pchB.

Seed cultures of *E. coli* strains were cultured in Luria-Bertani (LB) broth at 32° C. and supplemented with 100 mg/L ampicillin, 35 mg/L kanamycin, and/or 34 mg/L chloramphenicol, as appropriate. For phenol biosynthesis, shake flasks were cultured at 32° C. in MM1 phosphate limited minimal media supplemented with appropriate antibiotics. MM1 was composed of the following (in g/L): $MgSO_4.7H_2O$ (0.5), $(NH_4)_2SO_4$ (4.0), MOPS (24.7), $KH_2PO_4$ (0.3), $K_2HPO_4$ (0.7), and glucose (20). Trace elements were supplemented in MM1 as follows (in mg/L): $(NH_4)_6Mo_7O_{24}.4H_2O$ (0.37), $H_3BO_3$(2.5), $CoCl_2.6H_2O$ (0.714), $CuSO_4$ (0.16), $MnCl_2.4H_2O$ (1.6), $ZnSO_4.7H_2O$ (0.288), $FeCl_3$ (0.05).

Plasmid Construction

All plasmids used and developed in this study are listed in Table 6. All genes were PCR amplified with Q5 High-Fidelity DNA Polymerase (NEB) and a BioRad iCycler, per manufacturer protocols. Custom DNA oligonucleotide primers (Table 7) were synthesized by Integrated DNA Technologies (IDT, Coralville Iowa). Genomic DNA (gDNA) templates were prepared using the ZR Fungal/Bacterial DNA MiniPrep kit while plasmid DNA was purified using the Zymo Plasmid MiniPrep kit (both Zymo Research, Irvine Calif.). Amplified linear DNA fragments were purified using the Zymo DNA Clean & Concentrator MiniPrep kit (Zymo Research). Select purified linear and plasmid DNA were digested using appropriate restriction endonucleases (NEB) and subsequently gel purified using the Zymoclean Gel DNA Recovery MiniPrep kit (Zymo Research). Purified digested DNA fragments were ligated using T4 DNA Ligase (NEB), per manufacturer protocols. Alternatively, purified linear DNA was subsequently used as template DNA for either circular polymerase extension cloning (CPEC) (Quan, J., Tian, J., 2011. Nat. Protocols. 6, 242-251) with Q5 High-Fidelity DNA Polymerase according to manufacturer protocols, or Gibson Assembly (Gibson, et al., 2009. Nature methods. 6, 343-5) using Gibson Assembly Master Mix (NEB) according to manufacturer protocols. Ligation, CPEC, and Gibson Assembly reactions were transformed into chemically competent *E. coli* NEB10-beta before plating on LB solid agar media supplemented with appropriate antibiotics for selection. Transformant pools were screened using colony PCR, restriction digest mapping, and finally confirmed by DNA sequencing.

Strain Construction

Chromosomal in-frame deletions of pheA in *E. coli* NST74 was constructed using a modified version of the Datsenko and Wanner method (Datsenko, K. A., Wanner, B. L., 2000. et al., Proc Natl Acad Sci USA. 97, 6640-5), as previously described (Pugh, et al., 2014. Process Biochemistry. 49, 1843-1850). The pheA::FRT-kan$^R$-FRT, pykA::FRT-kan$^R$-FRT, pykF::FRT-kan$^R$-FRT, and crr::FRT-kan$^R$-FRT deletion cassettes were PCR amplified from *E. coli* JW2580-1, JW1843-2, JW1666-3, and JW2410-1, respectfully. Chromosomal integration of said cassette and subsequent removal of kan$^R$ marker was achieved as previously described (Datsenko, K. A., Wanner, B. L., 2000. et al., Proc Natl Acad Sci USA. 97, 6640-5; Pugh, et al., 2014. Process Biochemistry. 49, 1843-1850), resulting in the individual construction of *E. coli* NST74 ΔpheA and *E. coli* NST74 ΔpheA ΔpykA ΔpykF Δcrr.

For phenol biosynthesis, *E. coli* NST74 ΔpheA and *E. coli* NST74 ΔpheA ΔpykA ΔpykF Δcrr was co-transformed with the following combinations of plasmids (pathway designations provided in parentheses, see Table 8): pTyrAfbr-TutA (PH1); pSDC-PchB-EntC (PH2); pUbiC-Kpd (PH3); pTyrAfbr-TutA and pSDC-PchB-EntC (PHF1); pTyrAfbr-TutA and pUbiC-Kpd (PHF2); pSDC-PchB-EntC and pUbiC-Kpd (PHF3); pTyrAfbr-TutA, pSDC-PchB-EntC, and pUbiC-Kpd (PHF4).

Phenol Bioproduction

To investigate the bioproduction of phenol, overnight seed cultures were first prepared in LB and supplemented with 100 mg/L ampicillin, 35 mg/L kanamycin, and/or 34 mg/L chloramphenicol and used to inoculate (1% vol) 50 mL of MM1 minimal media supplemented with 20 g/L glucose in 250 mL shake flasks (note: the medium was additionally supplemented with 0.1 g/L Phe when using ΔpheA-derived host strains). Shake flask cultures were incubated at 32° C. with shaking at 200 RPM until reaching $OD_{600}$~0.7, at which point IPTG induction was performed at a final concentration of 0.4 mM. Cultures were further incubated for a total of up to 120 h, or until significant sugar consumption was no longer detected. Periodically, samples were drawn to measure cell growth (as $OD_{600}$) as well as sugar and metabolite levels by HPLC analysis, as described below. Prior to centrifugation, samples for Tyr analysis were diluted 1:10 with 1 N HCl and incubated at 55° C. for 30 min. All samples were then centrifuged at 11,000×g for 5 min before transferring the supernatant to a glass HPLC vial.

HPLC Metabolite Analysis

Metabolite analysis was performed using a Hewlett Packard 1100 series HPLC system. Separation of Phe, pHBA, salicylate, and phenol was achieved using a reverse-phase Hypersil GOLD aQ C18 column (3 mm×250 mm; Thermo Fisher, Waltham, Mass., USA) operated at 45° C. with an isocratic 0.8 mL/min mobile phase consisting of 85% (vol.) 5 mM $H_2SO_4$ and 15% (vol.) acetonitrile. The eluent was monitored using a diode array detector (DAD) set at 215 nm for salicylate, 260 nm for pHBA, and 275 nm for phenol. Separation of Tyr was also achieved on the same Hypersil GOLD aQ C18 column, in this case maintained at 30° C. while using a mobile phase consisting of water (A) and methanol plus 0.1% (vol.) formic acid (B) at a constant flow rate of 0.2 mL/min and the following concentration gradient (all by vol.): 5% B from 0 to 8 min, 5% to 40% B from 8 to 13 min, 40% B from 13 to 16 min, 40 to 5% B from 16 to 21 min, and 5% B from 21 to 31 min. The eluent was monitored using a DAD at 215 nm. Glucose and acetate separation was achieved using an Aminex HPX-87H column (BioRad, Hercules, Calif.) operated at 35° C. and detected using a refractive index detector (RID). The column was eluted with 5 mM $H_2SO_4$ at a constant flow rate of 0.55 mL/min. In all cases, external standards were prepared and used to provide calibrations for concentration determination.

Results and Discussion

Demonstrating Phenol and MA Production Via Synthetic 'Metabolic Funneling'

A synthetic 'metabolic funneling' approach was investigated as a novel strategy for improving phenol bioproduction metrics. Multiple 'funneling' strategies were investigated by co-expressing both the original tyrosine-derived pathway (PH1, FIG. 7) with the salicylate derived pathway (PH2, FIG. 7) and/or the p-hydroxybenzoate (pHBA) derived pathway (PH3, FIG. 7). In this way, phenol production occurs via either two or three simultaneous and compatible routes (PHF1-4, Table 8). Phenol 'funneling' pathways were first introduced and expressed in *E. coli* NST74 ΔpheA. In the case of PHF1, titers reached 439±7 mg/L (a 16% increase over the best-performing, single pathway control) at a glucose yield of 24.0±0.51 mg/g. In the case of PHF2, titers reached 355±17 mg/L at a glucose yield of 17.8±1.2 mg/g. Meanwhile, phenol titers by PHF3 reached just 149±10 mg/L at a glucose yield of 8.4±1.0 mg/g. Finally, with all three pathways expressed simultaneously (PHF4), phenol titers reached 205±13 mg/L at a glucose yield of 11.8±0.72 mg/g. Meanwhile, significant acetate accumulation was observed in all cases (Table 9) suggesting high rates of glucose consumption and significant overflow metabolism.

Host Engineering to Enhance Precursor Availability

To further improve phenol production, subsequent strain engineering efforts were focused on increasing total carbon flux into the shikimic acid pathway and reducing overflow metabolism observed with high glucose uptake rates (Liu, et al., 2014. Process Biochemistry. 49, 751-757). Flux into the shikimic acid pathway is initially controlled by 3-deoxy D-arabinoheptulose 7-phosphate (DAHP) synthase, whose two substrates are phosphoenolpyruvate (PEP) and erythrose 4-phosphate (E4P) (Bongaerts, et al., 2001. Metabolic engineering. 3; Gosset, G., 2009. Current opinion in biotechnology. 20; Rodriguez, et al., 2014. Microb Cell Fact. 13). As previously demonstrated (Gosset, G., 2005. Microb Cell Fact. 4, 14; Postma, et al., 1993. Microbiol Rev. 57), increasing the intracellular availability of PEP is an effective strategy for enhancing the production of aromatic amino acids (Liu, et al., 2014. Process Biochemistry. 49, 751-757) and other products from intermediates of the shikimic acid pathway (Noda, et al., 2016. Metabolic engineering. 33, 119-129). In glucose-fed cultures, PEP availability can be increased by blocking its conversion to pyruvate via deletion of pykA and pykF, both of which encode isozymes of pyruvate kinase. Meanwhile, rapid uptake of glucose has been previously reported to result in the accumulation of acetate (Gosset, G., 2005. Microb Cell Fact. 4, 14)—an undesirable byproduct which can ultimately inhibit cell metabolism (Shiloach, et al., 1996. Biotechnol Bioeng. 49, 421-8) and result in lower aromatic product yields (Liu, et al., 2014. Process Biochemistry. 49, 751-757). Carbohydrate repression resistant null mutants (i.e., Δcrr) have been previously shown to display lower rates of glucose uptake and thus reduced overflow metabolism—a strategy demonstrated as effective for enhancing phenylalanine production (Liu, et al., 2014. Process Biochemistry. 49, 751-757). Accordingly, *E coli* NST74 ΔpheA ΔpykA ΔpykF Δcrr was next constructed and evaluated as a phenol production host.

Here, the focus was narrowed to the three best performing pathways: PH1, PH3, and PHF1. The individual pathways PH1 and PH3 displayed a modest decrease in titer and yield when using *E coli* NST74 ΔpheA ΔpykA ΔpykF Δcrr as host, with final phenol titers reaching 329±9 and 277±15 mg/L, respectively (Table 10). On the other hand, phenol production by PHF1 was slightly enhanced, with final titers reaching 575±19 at a glucose yield of 28.8±0.34—a 1.3 and 1.2-fold increase relative to the previous generation strain. In addition, the titer demonstrated by PHF1 represents a 4-fold increase over the original phenol biosynthesis reported using the solvent tolerant *P. putida* (Wierckx, et al., 2005. Applied and environmental microbiology. 71, 8221-7) and a 1.4-fold increase over the highest *E. coli* derived phenol production reported to date (Kim, et al., 2014. Biotechnology journal. 9, 621-9).

Tables

TABLE 1

Strains, plasmids, and pathways constructed and/or used in Example 1.

| Strain | Description | Source |
|---|---|---|
| E. coli NEB 10-beta | Δ(ara-leu) 7697 araD139 fhuA ΔlacX74 galK16 galE15 e14- ϕ80dlacZΔM15 recA1 relA1 endA1 nupG rpsL ($Str^R$) rph spoT1 Δ(mrr-hsdRMS-mcrBC) | NEB |
| *E. coli* BW25113 | Source of *ubiC* and *entC* | CGSC |
| *E. coli* JW2580-1 | Source of *pheA*::$Kan^R$ | CGSC |
| *E. coli* JW1843-2 | Source of *pykA*::$Kan^R$ | CGSC |
| *E. coli* JW1666-3 | Source of *pykF*::$Kan^R$ | CGSC |
| *E. coli* JW2410-1 | Source of crr::$Kan^R$ | CGSC |
| *E. coli* NST74 | aroH367, tyrR366, tna-2, lacY5, aroF394(fbr), malT384, pheA101(fbr), pheO352, aroG397(fbr) | ATCC |
| *E. coli* NST74 | $pheA^{fbr}$ chromosomal deletion in *E. coli* NST74 | Pugh et al. |

TABLE 1-continued

Strains, plasmids, and pathways constructed and/or used in Example 1.

| | | |
|---|---|---|
| $\Delta$pheA$^{fbr}$ | | (2014) |
| *C. glutamicum* | Source of qsuB | ATCC |
| *C. braakii* | Source of tutA | ATCC |
| *P. aeruginosa* PAO1 | Source of pobA and pchB | DSMZ |
| *E. coli* BW25113 | Source of ubiC and entC | CGSC |
| *K. pneumoniae* PZH572 | Source of kpdBCD and aroY | ATCC |
| *P. stutzeri* OX1 | Source of phKLMNOP | ATCC |
| *P. putida* KT2440 | Source of catA | ATCC |

| Plasmid | Description | Source |
|---|---|---|
| pTrc99A | pBR322 ori Amp$^r$, lacIq, $P_{trc}$ | Prather Lab, MIT |
| pTrcCOLAK | ColA ori, Kan$^r$, lacIq, $P_{trc}$ | McKenna et al. (2013) |
| pY3 | p15A, Amp$^r$, lacI,$P_{lac-UV5}$-tyrB-tyrA$^{fbr}$-aroC T1-$P_{trc}$-aroA-aroL | Juminaga et al. (2012) |
| pKD46 | repA101(ts) and R101 ori, Amp$^r$, araC, araBp | CGSC |
| pCP20 | FLP, ts-rep, [cI857](lambda)(ts), Amp$^r$ | CGSC |
| pTutA-Ph | tutA of *C. braakii* inserted to pPh | This study |
| pTutA-Ph-CatA | tutA of *C. braakii* inserted to pPh-CatA | This study |
| pSDC-PchB-EntC | SDC of *T. moniliforme*, pchB of *P. aeruginosa* PAO1, and entC of *E. coli* BW25113 inserted to pTrc99A | This study |
| pUbiC-Kpd | ubiC of *E. coli* BW25113 and kpdBCD of *K. pneumoniae* PZH572 inserted to pTrc99A | This study |
| pPh | phKLMNOP of *P. stutzeri* OX1 inserted to pTrcCOLAK | This study |
| pPh-CatA | catA of *P. putida* KT2440 inserted to pPh | This study |
| pUbiC-PobA | ubiC of *E. coli* BW25113 and pobA of *P. aeruginosa* PAO1 inserted to pTrc99A | Pugh et al. (2014) |
| pAroY | aroY of *K. pneumoniae* PHZ572 inserted to pTrcCOLAK | Pugh et al. (2014) |
| pAroY-CatA | catA of *P. putida* KT2440 inserted to pAroY | This study |
| pQsuB-AroY-CatA | qsuB of *C. glutamicum* inserted to pTrc99A | This study |

| Pathway | Plasmid Combination | Source |
|---|---|---|
| CAT2 | pY3, pTutA-Ph | This study |
| CAT3 | pSDC-PchB-EntC, pPh | This study |
| CAT4 | pUbiC-Kpd, pPh | This study |
| CAT5 | pUbiC-PobA, pAroY | Pugh et al. (2014) |
| MA1 | pQsuB-AroY-CatA | This study |
| MA2 | pY3, pTutA-Ph-CatA | This study |
| MA3 | pSDC-PchB-EntC, pPh-CatA | This study |
| MA4 | pUbiC-Kpd, pPh-CatA | This study |
| MA5 | pUbiC-PobA, pAroY-CatA | This study |
| MAF | pUbiC-PobA, pQsuB-AroY-CatA | This study |

(Pugh, et al., 2014. Process Biochemistry. 49, 1843-1850)

TABLE 2

Primers designed and used in Example 1. Underlined bases indicate restriction site used for cloning.

| Primer | Sequence (5' → 3') |
|---|---|
| SEQ ID NO 32 | ATA GGA TCC AGG AGG ATA AAT AAT GCG TAC ATC CAT TGC CAC TGT TTG |
| SEQ ID NO 33 | ATT AAG CTT CTA GTT TGG GAT TCC CCG CTC GA |
| SEQ ID NO 20 | ATA CCT GCA GGA GGA GGA TAA ATA ATG ACC GTG AAA ATT TCC CAC ACT GC |
| SEQ ID NO 21 | ATA AAG CTT GGA GGA GGA TAA ATA ATG ACC GTG AAA ATT TCC CAC ACT GC |
| SEQ ID NO 22 | ATA GAA TTC AGG AGG ATA AAT AAT GAA TTA TCC GGC AGA ACC |
| SEQ ID NO 23 | ATT TCT AGA TTA GAT ATA GTC AAA GCG TGC AGT A |

TABLE 2 -continued

Primers designed and used in Example 1. Underlined bases indicate restriction site used for cloning.

| Primer | Sequence (5' → 3') |
|---|---|
| SEQ ID NO 16 | ATA GAA TTC AGG AGG ATA AAT AAT GCG TGG TAA AGT TAG CCT G |
| SEQ ID NO 17 | ATT GGA TCC TTA GGC TTC GCT GTC ATA GAA T |
| SEQ ID NO 14 | AAT ATC TAG ATT CCC GAG AGG TTG CAT GAT GAA AAC T |
| SEQ ID NO 15 | ATT GGA TCC TTA TGC GGC ACC CCG TGT CTG G |
| SEQ ID NO 12 | ATA GGA TCC AGG AGG ATA AAT AAT GGA TAC GTC ACT GGC TGA |
| SEQ ID NO 13 | ATT CTG CAG TTA ATG CAA TCC AAA AAC GTT |

TABLE 2 -continued

Primers designed and used in Example 1. Underlined bases indicate restriction site used for cloning.

| Primer | Sequence (5' → 3') |
|---|---|
| SEQ ID NO 24 | ATA GAA TTC AGG AGG ATA AAT AAT GTC ACA CCC CGC GTT AAC G |
| SEQ ID NO 25 | ATT AGA TCT TTA GTA CAA CGG TGA CGC CGG TAA A |
| SEQ ID NO 26 | ATA GGA TCC CCC GTC CGG AGA GGG TAA TTT AAA TAT AAA GTT CG |
| SEQ ID NO 27 | ATT AAG CTT CTT AGC GGG CCC CTT TAT TAA CGC T |
| SEQ ID NO 18 | ATA TCT AGA AGG AGG ATA AAT AGA GCT CGT GCT GCC TCA CGA |
| SEQ ID NO 19 | ATT CCT GCA GGA TGC CCA TGA CTA TAT CTT CTT GAA CAG GGC |
| SEQ ID NO 48 | CGT GTG AAA CAG AAT GCG AAG ACG AAC AAT A |
| SEQ ID NO 49 | TAA TCC AGT GCC GGA TGA TTC ACA TCA TC |
| SEQ ID NO 50 | ATC GCG GCG TTA TTT CAT TCG GAT T |
| SEQ ID NO 51 | AAC TGT AGG CCG GAT GTG GC |
| SEQ ID NO 52 | GCG AGG CAC CAC CAC TTT CG |
| SEQ ID NO 53 | AGC GCC CAT CAG GGC G |
| SEQ ID NO 54 | CTA TGA GCG CCA TTT CTA TCC CGC GC |
| SEQ ID NO 55 | CCT GAA AGG GAC TGG CGA CCT G |

TABLE 3

Catechol production via each of the proposed pathways using *E. coli* NST74 ΔpheA as host background. Strains were cultured for 120 h and initially supplied with 20 g/L glucose. Error represents one standard deviation from triplicate experiments. [a]Pugh, et al., 2014. Process Biochemistry. 49, 1843-1850.

| Pathway | Accumulated Intermediate(s) (mg/L) | Catechol (mg/L) | Glucose Utilization (%) | $Y_{P/S}$ (mg/g) |
|---|---|---|---|---|
| CAT2 | Tyr: 342 ± 12 Phenol: 149 ± 1 | 79 ± 3 | 65 ± 1 | 6.2 ± 0.28 |
| CAT3 | Salicylate: 55 ± 2 Phenol: 111 ± 2 | 100 ± 2 | 39 ± 1 | 12.8 ± 0.26 |
| CAT4 | Phenol: 125 ± 9 | 51 ± 10 | 27 ± 1 | 9.4 ± 2.1 |
| CAT5[a] | n.d. | 451 ± 44 | 64 ± 1 | 35.0 ± 3.0 |

TABLE 4

MA production via each of the proposed pathways using *E. coli* NST74 ΔpheA as host background. Strains were cultured for 120 h and initially supplied with 20 g/L glucose. Error represents one standard deviation from triplicate experiments.

| Pathway | Accumulated Intermediate Metabolite (mg/L) | MA (mg/L) | Acetate (g/L) | Glucose utilization (%) | $Y_{P/S}$ (mg/g) |
|---|---|---|---|---|---|
| MA1 | n.d. | 1586 ± 11 | 12 ± 0.20 | 100 ± 1 | 79.3 ± 0.53 |
| MA2 | Tyr: 220 ± 12 Phenol: 63 ± 1 | 186 ± 11 | 10 ± 1.4 | 44 ± 4 | 21.0 ± 2.2 |
| MA3 | n.d. | 484 ± 44 | 7.1 ± 0.12 | 52 ± 2 | 46.7 ± 6.0 |
| MA4 | n.d. | 230 ± 20 | 7.1 ± 0.13 | 36 ± 1 | 31.8 ± 3.6 |
| MA5 | n.d. | 819 ± 44 | 12 ± 0.21 | 100 ± 1 | 40.9 ± 2.2 |
| MAF | n.d. | 2042 ± 88 | 11 ± 0.17 | 100 ± 1 | 102 ± 4.4 |

TABLE 5

Investigating 'metabolic funneling' for improving MA production using *E. coli* NST74 ΔpheA ΔpykA ΔpykF Δcrr as the host background. Strains were cultured for 120 h and initially supplied with 20 g/L glucose. Error represents one standard deviation from triplicate experiments.

| Pathway | MA (mg/L) | Acetate (g/L) | Glucose utilization (%) | $Y_{P/S}$ (mg/g) |
|---|---|---|---|---|
| MA1 | 1792 ± 28 | n.d. | 100 ± 1 | 89.6 ± 1.4 |
| MAF | 3153 ± 149 | 7 ± 0.1 | 100 ± 1 | 158 ± 7.4 |

TABLE 6

Strains, plasmids, and pathways constructed and/or used in Example 2.

| Strain | Description | Source |
|---|---|---|
| *E. coli* NEB10-beta | Δ(ara-leu) 7697 araD139 fhuA ΔlacX74 galK16 galE15 e14- φ80dlacZΔM15 recAl relAl endAl nupG rpsL ($Str^R$) rph spoT1 Δ(mrr-hsdRMS-mcrBC) | NEB |
| *E. coli* BW25113 | Source of ubiC and entC | CGSC |
| *E. coli* JW2580-1 | Source of pheA::$Kan^R$ | CGSC |
| *E. coli* JW1843-2 | Source of pykA::$Kan^R$ | CGSC |
| *E. coli* JW1666-3 | Source of pykF::$Kan^R$ | CGSC |
| *E. coli* JW2410-1 | Source of crr::$Kan^R$ | CGSC |
| *E. coli* NST74 | aroH367, tyrR366, tna-2, lacY5, aroF394(fbr), malT384, pheA101(fbr), pheO352, aroG397(fbr) | ATCC |
| *E. coli* NST74 ΔpheA | pheA chromosomal deletion in *E. coli* NST74 | Pugh et al. (2014) |
| *E. coli* NST74 ΔpheA ΔpykA ΔpykF Δcrr | crr chromosomal deletion in *E. coli* NST74 ΔpheA ΔpykA ΔpykF | This study |
| *C. braakii* | Source of tutA | ATCC |
| *P. aeruginosa* PAO1 | Source of pchB | DSMZ |
| *E. coli* BW25113 | Source of ubiC and entC | CGSC |
| *K. pneumoniae* PZH572 | Source of kpdBCD | ATCC |
| **Plasmid** | **Description** | **Source** |
| pTrcCOLAK | ColA ori, $Kan^r$, lacIq, $P_{trc}$ | McKenna et al. (2013) |
| pY3 | p15A, $Amp^r$, lacI, $P_{lac-UV5}$-tyrB-$tyrA^{fb}$r-aroC T1-$P_{trc}$-aroA-aroL | Juminaga et al. (2012) |
| pS3 | pBBR1 ori; $Cm^r$, lacI $P_{lac-UV5}$-aroE-aroD-$aroB^{op}$-$aroG^{fbr}$-ppsA-tktA | Juminaga et al. (2012) |
| pKD46 | repA101(ts) and R101 ori, $Amp^r$, araC, araBp | CGSC |
| pCP20 | FLP, ts-rep, [cI857](lambda)(ts), $Amp^r$ | CGSC |
| pTyrAfbr-TutA | $tyrA^{fbr}$ of *E. coli* and tutA of *C. braakii* inserted to pY3 backbone | This study |
| pSDC-PchB-EntC | SDC of *T. moniliforme*, pchB of *P. aeruginosa* PAO1, and entC of *E. coli* BW25113 inserted to pS3 backbone | This study |
| pUbiC-Kpd | ubiC of *E. coli* and kpdBCD of *K. pneumoniae* PZH572 inserted to pTrcCOLAK | Thompson et al. (2016) |

(Pugh, et al., 2014. Process Biochemistry. 49, 1843-1850; Thompson, et al., 2016. Biotechnol Bioeng. 113 (8), 1745-54)

TABLE 7

Primers designed and used in Example 2. Underlined bases indicate restriction site used for cloning.

| Primer | Sequence (5' → 3') |
|---|---|
| SEQ ID NO 22 | ATA GAA TTC AGG AGG ATA AAT AAT GAA TTA TCC GGC AGA ACC |
| SEQ ID NO 23 | ATT TCT AGA TTA GAT ATA GTC AAA GCG TGC AGT A |
| SEQ ID NO 14 | AAT ATC TAG ATT CCC GAG AGG TTG CAT GAT GAA AAC T |

TABLE 7-continued

Primers designed and used in Example 2. Underlined bases indicate restriction site used for cloning.

| Primer | Sequence (5' → 3') |
|---|---|
| SEQ ID NO 15 | ATT GGA TCC TTA TGC GGC ACC CCG TGT CTG G |
| SEQ ID NO 12 | ATA GGA TCC AGG AGG ATA AAT AAT GGA TAC GTC ACT GGC TGA |
| SEQ ID NO 13 | ATT CTG CAG TTA ATG CAA TCC AAA AAC GTT |

TABLE 7-continued

| Primers designed and used in Example 2. Underlined bases indicate restriction site used for cloning. | |
|---|---|
| Primer | Sequence (5' → 3') |
| SEQ ID NO 16 | ATA CCA TGG AGG AGG ATA AAT AAT GCG TGG TAA AGT TAG CCT G |
| SEQ ID NO 17 | ATT GGA TCC TTA GGC TTC GCT GTC ATA GAA T |
| SEQ ID NO 24 | ATA GAA TTC AGG AGG ATA AAT AAT GTC ACA CCC CGC GTT AAC G |
| SEQ ID NO 25 | ATT AGA TCT TTA GTA CAA CGG TGA CGC CGG TAA A |
| SEQ ID NO 26 | ATA GGA TCC CCC GTC CGG AGA GGG TAA TTT AAA TAT AAA GTT CG |
| SEQ ID NO 27 | ATT AAG CTT CTT AGC GGG CCC CTT TAT TAA CGC T |
| SEQ ID NO 34 | AGA TCT AAA GGA GGC CAT CCA TGG CTG GAA ACA CAA TTG G |
| SEQ ID NO 35 | ATG CCT GGA GAT CCT TAC TCG AGT TTG GAT CCT C |
| SEQ ID NO 36 | GAG GAT CCA AAC TCG AGT AAG GAT CTC CAG GCA T |
| SEQ ID NO 37 | CCA ATT GTG TTT CCA GCC ATG GAT GGC CTC CTT TAG ATC T |
| SEQ ID NO 38 | CTG CAC GCT TTG ACT ATA TCT AAG GAT CCA AAC TCG AGT AAG G |
| SEQ ID NO 39 | CAT GGA TGG CCT CCT AGA TCT TTT GAA TTC TGA AAT TGT TAT C |
| SEQ ID NO 40 | GAT AAC AAT TTC AGA ATT CAA AAG ATC TAG GAG GCC ATC CAT G |

TABLE 7-continued

| Primers designed and used in Example 2. Underlined bases indicate restriction site used for cloning. | |
|---|---|
| Primer | Sequence (5' → 3') |
| SEQ ID NO 41 | CGG ATA ATT CAT TAT TTA TCC TCC TTT AGA TCC TTA CTG GCG ATT |
| SEQ ID NO 42 | AAT CGC CAG TAA GGA TCT AAA GGA GGA TAA ATA ATG AAT TAT CCG |
| SEQ ID NO 43 | CCT TAC TCG AGT TTG GAT CCT TAG ATA TAG TCA AAG CGT GCA G |
| SEQ ID NO 44 | AAG GAG GCC ATC CAT GCG TGG TAA AGT TAG C |
| SEQ ID NO 45 | GTT TGG ATC CTT AAT GCA ATC CAA AAA CG |
| SEQ ID NO 46 | ATT GCA TTA AGG ATC CAA ACT CGA GTA AG |
| SEQ ID NO 47 | CTT TAC CAC GCA TGG ATG GCC TCC TTT AGA TC |

TABLE 8

Pathways Constructed for Phenol Production via Synthetic 'Metabolic Funneling'.

| Pathway | Plasmid Combination | Source |
|---|---|---|
| PH1 | pTyrAfbr-TutA, | This study |
| PH2 | pSDC-PchB-EntC | This study |
| PH3 | pUbiC-Kpd | This study |
| PHF1 | pTyrAfbr-TutA, pSDC-PchB-EntC | This study |
| PHF2 | pTyrAfbr-TutA, pUbiC-Kpd | This study |
| PHF3 | pSDC-PchB-EntC, pUbiC-Kpd | This study |
| PHF4 | pTyrAfbr-TutA, pSDC-PchB-EntC, pUbiC-Kpd | This study |

TABLE 9

Evaluating the Effects of Synthetic 'Metabolic Funneling' for Phenol Biosynthesis. All pathways were expressed using *E. coli* NST74 ΔpheA as host background. Strains were cultured fbr 120 h and initially supplied with 20 g/L glucose. Error represents one standard deviation from triplicate experiments.

| Pathway | Phenol (mg/L) | Glucose Utilization (%) | Acetate (g/L) | $Y_{P/S}$ (mg/g) |
|---|---|---|---|---|
| PH1 | 377 ± 23 | 100 ± 1 | 9 ± 0.1 | 18.7 ± 0.72 |
| PH2 | 377 ± 14 | 53 ± 0.7 | 6 ± 0.3 | 35.7 ± 0.80 |
| PH3 | 149 ± 12 | 100 ± 1 | 4 ± 0.3 | 7.3 ± 0.31 |
| PHF1 | 439 ± 7 | 90 ± 0.9 | 8 ± 0.2 | 24.0 ± 0.51 |
| PHF2 | 355 ± 17 | 100 ± 1 | 6 ± 0.2 | 17.8 ± 1.2 |
| PHF3 | 149 ± 10 | 90 ± 0.4 | 6 ± 0.3 | 8.4 ± 1.0 |
| PHF4 | 205 ± 13 | 87 ± 0.3 | 5 ± 0.2 | 11.8 ± 0.72 |

TABLE 10

Comparing Engineering Strategies for Phenol Production. All pathways were expressed using *E. coli* NST74 ΔpheA ΔpykA ΔpykF Δcrr as the host background. Strains were cultured for 120 h and initially supplied with 20 g/L glucose. Error represents one standard deviation from triplicate experiments.

| Pathway | Phenol (mg/L) | Glucose Utilization (%) | Acetate (g/L) | $Y_{P/S}$ (mg/g) |
|---|---|---|---|---|
| PH1 | 329 ± 9 | 100 ± 1 | 6 ± 0.1 | 16.4 ± 0.65 |
| PH2 | 277 ± 15 | 100 ± 1 | 7 ± 0.1 | 13.8 ± 0.19 |
| PHF1 | 575 ± 19 | 100 ± 1 | 5 ± 0.3 | 28.8 ± 0.34 |

All publications, patents, and patent documents are incorporated by reference herein, as though individually incorporated by reference. The invention has been described with reference to various specific and illustrative embodiments and techniques. However, it should be understood that many variations and modifications may be made while remaining within the spirit and scope of the invention.

What is claimed is:

1. A method for preparing a biochemical product that is muconic acid, the method comprising:

i) contacting a recombinant host cell with a fermentable carbon source, wherein the recombinant host cell is a bacteria, yeast, or filamentous fungi cell, wherein the recombinant host cell co-expresses a recombinant MA1 pathway and a recombinant MA5 pathways, and wherein:

a) each pathway is capable of producing the same final biochemical product;

b) each pathway comprises at least one gene encoding a polypeptide;

c) each pathway is derived from a different endogenous metabolite as its immediate precursor; and d) each pathway converges to the same final product or the same intermediate metabolite; and ii) growing said recombinant host cell for a time sufficient to synthesize the product;

wherein the recombinant MA1 pathway comprises at least one gene encoding a polypeptide having 3-dehydroshikimate dehydratase activity; at least one gene encoding a polypeptide having protocatechuate decarboxylase activity; and at least one gene encoding a polypeptide having 1,2-catechol dioxygenase activity; and wherein the recombinant MA5 pathway comprises at least one gene encoding a polypeptide having chorismate lyase activity; at least one gene encoding a polypeptide having p-hydroxybenzoate hydroxylase activity; at least one gene encoding a polypeptide having protocatechuate decarboxylase activity; and at least one gene encoding a polypeptide having 1,2-catechol dioxygenase activity.

2. The method of claim 1, wherein:

a) the at least one gene encoding a polypeptide having 3-dehydroshikimate dehydratase activity comprises a sequence having at least about 70% sequence identity to SEQ ID NO:11;

b) the at least one gene encoding a polypeptide having protocatechuate decarboxylase activity comprises a sequence having at least about 70% sequence identity to SEQ ID NO:10;

c) the at least one gene encoding a polypeptide having chorismate lyase activity comprises a sequence having at least about 70% sequence identity to SEQ ID NO:7; and d) the at least one gene encoding a polypeptide having p-hydroxybenzoate hydroxylase activity comprises a sequence having at least about 70% sequence identity to SEQ ID NO:9.

3. The method of claim 1, wherein:

a) the at least one gene encoding a polypeptide having 3-dehydroshikimate dehydratase activity is aroZ, quiC or qsuB;

b) the at least one gene encoding a polypeptide having chorismate lyase activity is ubiC;

c) the at least one gene encoding a polypeptide having p-hydroxybenzoate hydroxylase activity is pobA; and d) the at least one gene encoding a polypeptide having protocatechuate decarboxylase activity is aroY.

4. The method of claim 1, wherein the at least one gene encoding a polypeptide having 1,2-catechol dioxygenase activity comprises a sequence having at least about 70% sequence identity to SEQ ID NO:5.

5. The method of claim 1, wherein the at least one gene encoding a polypeptide having 1,2-catechol dioxygenase activity is catA or salD.

6. The method of claim 1, wherein the fermentable carbon source is selected from the group consisting of monosaccharides, oligosaccharides, polysaccharides, glycerol, carbon dioxide, methanol, methane, formaldehyde, formate, amino acids, and carbon-containing amines.

7. The method of claim 1, wherein the recombinant host cell is yeast.

8. The method of claim 1, wherein the recombinant host cell is selected from the group consisting of *Escherichia, Salmonella, Bacillus, Acinetobacter, Streptomyces, Sphingomonas, Yarrowia, Clostridium, Corynebacterium, Methylosinus, Methylomonas, Rhodococcus, Pseudomonas, Rhodobacter, Synechocystis, Saccharomyces, Klebsiella, Zygosaccharomyces, Kluyveromyces, Candida, Hansenula, Debaryomyces, Mucor, Pichia, Torulopsis, Aspergillus, Arthrobotrys, Brevibacterium, Microbacterium, Arthrobacter, Ctirobacter*, and *Zymomonas*.

9. The method of claim 8, wherein the recombinant host cell is *E. coli* NST74, *E. coli* NST74 ΔpheA, *E. coli* NST74 ΔpheA ΔpykA ΔpykF or *E. coli* NST74 ΔpheA ΔpykA ΔpykF Δcrr.

10. The method of claim 1, wherein the recombinant host cell comprises a plasmid combination pUbiC-PobA and pQsuB-AroY-CatA.

11. The method of claim 8, wherein the recombinant host cell is *E. coli* NST74 ΔpheA ΔpykA ΔpykF Δcrr.

12. The method of claim 1, wherein the recombinant host cell is bacteria.

13. The method of claim 1, wherein the recombinant host cell is *Escherichia*.

14. The method of claim 1, wherein the recombinant host cell is filamentous fungi.

15. The method of claim 12, wherein the bacteria is cyanobacteria.

* * * * *

SEQUENCE LISTING

```
<160> NUMBER OF SEQ ID NOS: 59

<210> SEQ ID NO 1
<211> LENGTH: 1176
<212> TYPE: DNA
<213> ORGANISM: Escherichia coli

<400> SEQUENCE: 1

atggatacgt cactggctga ggaagtacag cagaccatgg caacacttgc gcccaatcgc     60

tttttcttta tgtcgccgta ccgcagtttt acgacgtcag gatgtttcgc ccgcttcgat    120

gaaccggctg tgaacgggga ttcgcccgac agtcccttcc agcaaaaact cgccgcgctg    180

tttgccgatg ccaaagcgca gggcatcaaa aatccggtga tggtcggggc gattcccttc    240

gatccacgtc agccttcgtc gctgtatatt cctgaatcct ggcagtcgtt ctcccgtcag    300

gaaaaacaag cttccgcacg ccgtttcacc cgcagccagt cgctgaatgt ggtggaacgc    360

caggcaattc cggagcaaac cacgtttgaa cagatggttg cccgcgccgc cgcacttacc    420

gccacgccgc aggtcgacaa agtggtgttg tcacggttga ttgatatcac cactgacgcc    480

gccattgata gtggcgtatt gctggaacgg ttgattgcgc aaaacccggt tagttacaac    540

ttccatgttc cgctggctga tggtggcgtc ctgctggggg ccagcccgga actgctgcta    600

cgtaaagacg gcgagcgttt tagctccatt ccgttagccg gttccgcgcg tcgtcagccg    660

gatgaagtgc tcgatcgcga agcaggtaat cgtctgctgg cgtcagaaaa agatcgccat    720

gaacatgaac tggtgactca ggcgatgaaa gaggtactgc gcgaacgcag tagtgagtta    780

cacgttcctt cttctccaca gctgatcacc acgccgacgc tgtggcatct cgcaactccc    840

tttgaaggta aagcgaattc gcaagaaaac gcactgactc tggcctgtct gctgcatccg    900

acccccgcgc tgagcggttt cccgcatcag gccgcgaccc aggttattgc tgaactggaa    960

ccgttcgacc gcgaactgtt tggcggcatt gtgggttggt gtgacagcga aggtaacggc   1020

gaatgggtgg tgaccatccg ctgcgcgaag ctgcgggaaa atcaggtgcg tctgtttgcc   1080

ggagcgggga ttgtgcctgc gtcgtcaccg ttgggtgagt ggcgcgaaac aggcgtcaaa   1140

ctttctacca tgttgaacgt tttggattg cattaa                                1176

<210> SEQ ID NO 2
<211> LENGTH: 306
<212> TYPE: DNA
<213> ORGANISM: Pseudomonas aeruginosa
```

<400> SEQUENCE: 2

```
atgaaaactc ccgaagactg caccggcctg gcggacatcc gcgaggccat cgaccggatc     60
gacctggata tcgtccaggc cctcggccgc cgcatggact acgtcaaggc ggcgtcgcgc    120
ttcaaggcca gcgaggcggc gattccggcg cccgagcggg tcgccgcgat gctccccgag    180
cgcgcccgct gggccgagga aaacggactc gacgcgccct tcgtcgaggg actgttcgcg    240
cagatcatcc actggtacat cgccgagcag atcaagtact ggcgccagac acggggtgcc    300
gcatga                                                               306
```

<210> SEQ ID NO 3
<211> LENGTH: 1053
<212> TYPE: DNA
<213> ORGANISM: Cutaneotrichosporon moniliiforme

<400> SEQUENCE: 3

```
atgcgtggta aagttagcct ggaagaagca tttgaactgc cgaaatttgc agcacagacc     60
aaagaaaaag ccgaactgta tattgcaccg aataatcgcg atcgctattt tgaagaaatt    120
ctgaatccgt gtggtaatcg tctggaactg agcaataaac atggtattgg ctataccatc    180
tatagcatct attcaccggg tccgcagggt tggaccgaac gtgcagaatg tgaagaatat    240
gcacgtgaat gcaacgatta tatcagcggt gaaattgcca atcacaaaga tcgtatgggt    300
gcatttgcag ccctgagcat gcatgatccg aaacaggcaa gcgaagaact gacccgttgt    360
gttaaagaac tgggttttct gggtgcactg gttaatgatg ttcagcatgc aggtccggaa    420
ggtgaaaccc atatctttta tgatcagccg gaatgggata tcttttggca gacctgtgtt    480
gatctggatg ttccgtttta tctgcatccg gaaccgcctt ttggtagcta tctgcgtaat    540
cagtatgaag gtcgcaaata tctgattggt ccgcctgtta gctttgcaaa tggtgttagc    600
ctgcatgttc tgggtatgat tgttaatggt gtgtttgatc gttttccgaa actgaaagtt    660
attctgggtc atctgggtga acatattccg ggtgattttt ggcgtattga acattggttt    720
gaacactgta gccgtccgct ggcaaaaagc cgtggtgatg tttttgcaga aaaaccgctg    780
ctgcattatt ttcgcaataa catttggctg accacgagcg gcaattttag caccgaaacc    840
ctgaaatttt gcgttgaaca tgttggtgca gaacgcattc tgtttagcgt tgatagcccg    900
tatgaacata tcgatgttgg ttgtggttgg tatgatgata atgccaaagc aattatggaa    960
gccgttggtg gtgaaaaagc ctataaagat attggtcgcg acaacgcgaa aaaactgttt   1020
aaactgggca aattctatga cagcgaagcc taa                               1053
```

<210> SEQ ID NO 4
<211> LENGTH: 4510
<212> TYPE: DNA
<213> ORGANISM: Pseudomonas stutzeri

<400> SEQUENCE: 4

```
gagctcgtgc tgcctcacga ggccttcgag attttctgca aacataacaa agtcgtccac     60
atggactcca acataatccg caaaattgac gaagacatgg tcaagtggcg gttcggagag    120
catggcaagc gctactgagc aagacgcatc ggcatacagt atcacaacaa caacacggta    180
aggttgatat gagtattgaa atcaagacca attcggtgga acctatccgc catacttatg    240
gccacatcgc ccgtcgcttc ggtgataagc cggctacccg ttatcaggag gccagctacg    300
acattgaggc aaagaccaat ttccattacc ggccccagtg ggattccgag cacaccctga    360
acgatcccac gcgtaccgcc atccgcatgg aagactggtg cgccgtttcc gatccccgcc    420
```

```
agttttacta tggcgcctat gtcggcaacc gggccaagat gcaggagtcg gccgagacca    480
gctttggctt ctgcgaaaag cgtaatctgc tgacccgcct ttccgaagaa acccagaagc    540
aattgttgcg gctgctggtg cccctgcgtc atgtcgagct tggcgccaac atgaacaacg    600
ccaagatcgc cggtgatgcc accgccacga ccgtctccca gatgcacatc tacactggga    660
tggatcgctt gggcattggc cagtacctgt cccgtattgc attgatgatt gatggcagca    720
ccggtgccgc tctggatgag tccaaggcct actggatgga tgacgaaatg tggcaaccca    780
tgcgcaagct ggtcgaagac acgcttgtgg tcgatgattg gtttgagctg actctggttc    840
agaacattct tatcgacgga atgatgtacc cgctggtcta cgacaagatg gaccagtggt    900
tcgaaagcca gggtgctgaa gatgtgtcca tgctcacgga gttcatgcgt gactggtaca    960
aggaatccct acgctggact aatgccatga tgaaagccgt ggccggtgaa agtgagacta   1020
accgtgagtt gcttcaaaaa tggatcgatc actgggaacc gcaggcctac gaagccctga   1080
aacctctggc cgaagcctcc gttggcatcg acgggctgaa tgaagcccgg gcggaactct   1140
ctgcccgcct gaagaaattc gaactgcaga gccggggagt ctcagcatga gccagcttgt   1200
atttattgta ttccaggaca acgacgactc ccgctacctc gcggaagccg ttatggaaga   1260
taaccccgac gccgaaatgc agcaccagcc ggccatgatc cggatccagg cggaaaaacg   1320
tctggtgatc aaccgcgaaa ccatggaaga aaagctgggg cgagactggg atgttcagga   1380
aatgctcata aatgttatca gcatcgccgg caacgtcgat gaagacgatg atcacttcat   1440
tcttgaatgg aattaatcgg gagaaacatc atggttagta aaaacaaaaa gcttaacctt   1500
aaagacaagt atcaatacct gacccgggat atggcctggg aaccgaccta tcaggacaag   1560
aaagatattt ttccggagga ggattttgag ggtatcaaga tcaccgactg gtcccagtgg   1620
gaagatccgt tccgcctgac catggatgcc tactggaaat accaggcgga aaaagagaag   1680
aagctgtacg ccattttcga tgcatttgcc cagaacaacg gccaccagaa catttcagac   1740
gcccgttatg tgaacgcgct aaaactgttc atcagtggta tatctccgct tgaacatgcg   1800
gcgttccagg gttattccaa ggtcggtcgc cagtttagcg gcgccggggc gcgggttgcc   1860
tgccagatgc aggcaattga cgagctgcgt cattcccaga cccagcaaca cgcgatgagc   1920
cactacaaca agcacttcaa cggtctgcac gatggcccgc acatgcacga tcgggtgtgg   1980
tacctgtcgg tgccgaaatc gttctttgat gatgcacgct cggctggtcc gttcgagttc   2040
ctgacggcca tctcattctc gttcgagtat gtgctcacca acctgttgtt cgtaccgttc   2100
atgtcgggcg ctgcctataa cggcgacatg gcgacagtca ccttcggttt ctccgcccag   2160
tctgacgaag cccgtcatat gaccctgggc cttgaggtga tcaagttcat cctcgagcag   2220
cacgaagata acgtgcccat cgttcagcgc tggatcgaca agtggttctg gcgcggattt   2280
cgcctgctta gcctggtcag catgatgatg gactacatgc tgccaaacaa ggtcatgtcc   2340
tggtccgagg catgggaagt ctattacgag cagaacggcg gtgctctgtt caaggacctg   2400
gagcgatacg gcatccgccc gcccaaatac caggacgtgg ctaacgatgc caaacatcac   2460
ctgagccacc agctttggac cactttctac cagtactgcc aggccaccaa cttccatact   2520
tggattccgg agaaggaaga gatggactgg atgtccgaga agtatccgga cactttcgac   2580
aagtactacc gtccgcgtta cgagtacctg gcgaaagagg ctgccgctgg ccgtcgcttc   2640
tacaacaaca ccctgccgca gctgtgccaa gtgtgtcaga tcccgaccat tttcaccgag   2700
aaagatgccc caaccatgct cagccatcgg cagatagaac atgagggcga acgctatcac   2760
```

```
ttctgctctg acggctgctg cgacatcttc aaacacgagc cggagaagta catacaggcc   2820

tggctgccgg tgcaccagat ctaccagggc aactgtgaag gcggggatct cgagaccgtg   2880

gtgcagaagt attaccacat caatatcgga gaggacaatt tcgactacgt tggatcgccc   2940

gaccagaaac actggctgtc gatcaagggc cggaagcctg cagacaagaa ccaggacgcc   3000

gcctgatatt gattggagag tcgcccggta gccgctggca ccgggtgaaa cacccataaa   3060

aacaacgagg tgaccatcat gagtgtaaac gcactttacg actacaagtt tgaacctaaa   3120

gacaaggtcg agaacttcca cggcatgcag ctgctgtatg tctactggcc cgatcacctg   3180

ctgttctgcg cgcccttcgc gctgctggtg cagccgggta tgaccttcag tgccctggtg   3240

gacgagattc tcaagccggc taccgccgcg cacccggact ctgccaaggc ggacttcctg   3300

aatgccgagt ggttgctgaa cgatgaaccg ttcacaccca aggctgacgc cagcctgaaa   3360

gagcagggta ttgatcacaa gagcatgctg acggtgacca cgccgggcct gaagggcatg   3420

gcgaacgccg gttactgagg gtagcactat gagttacacc gtcactattg agccgatcgg   3480

cgagcagatt gaggtagagg atggccagac tatcctcgcc gccgccctgc gccagggtgt   3540

ctggctgccc tttgcctgcg gccacggcac ctgtgctacc tgtaaggttc aggtgcttga   3600

aggtgatgtc gagatcggaa acgcctcgcc ctttgcgctg atggatatcg aacgtgacga   3660

gggcaaggtt ctggcctgct gcgccacggt tgagagcgac gtcaccattg aggtggacat   3720

cgatgtggat ccggattttg agggctaccc ggtggaggac tatgccgcca tagcgaccga   3780

tatcgtcgaa ctctctccga ccatcaaggg cattcacctg aaactggacc ggccgatgac   3840

attccaggcc ggccagtaca tcaatatcga actgccgggt gttgaaggcg cgagggcctt   3900

ctccctggcc aacccgccca gcaaagcaga cgaagtggag ctgcatgtgc gcctcgttga   3960

gggcggtgct gccaccacct acatccacga acaactgaaa acgggtgatg cgctgaacct   4020

ttcaggccct tacggccagt tcttcgtgcg tagttcccaa cccggcgatc tgattttcat   4080

cgccggcgga tccggattgt ccagtcccca gtcgatgatc cttgatctgc ttgagcagaa   4140

cgatgagcgc aagatcgttc tgttccaggg tgcccgaaac ctggcagagc tttacaaccg   4200

ggagctgttt gaggctctgg atcgcgacca cgacaatttc acctacgtac cggcgcttag   4260

ccaagccgac gaagaccctg actggaaggg cttccgaggc tatgtccatg aggcggccaa   4320

cgcccatttc gatggccggt ttgccggtaa caaggcatac ctgtgcggcc cgcctccaat   4380

gatcgatgcg gctatcacgg cattgatgca ggggcggctg ttcgagcgtg acatcttcat   4440

ggagaaattc ctgacagcgg cggacggagc tgaagacacc cagcgttcgg ccctgttcaa   4500

gaagatatag                                                          4510
```

<210> SEQ ID NO 5
<211> LENGTH: 936
<212> TYPE: DNA
<213> ORGANISM: Pseudomonas putida

<400> SEQUENCE: 5

```
atgaccgtga aaatttccca cactgccgac attcaagcct tcttcaaccg ggtagctggc     60

ctggaccatg ccgaaggaaa cccgcgcttc aagcagatca ttctgcgcgt gctgcaagac    120

accgcccgcc tgatcgaaga cctggagatt accgaggacg agttctggca cgccgtcgac    180

tacctcaacc gcctgggcgg ccgtaacgag gcaggcctgc tggctgctgg cctgggtatc    240

gagcacttcc tcgacctgct gcaggatgcc aaggatgccg aagccggcct tggcggcggc    300

accccgcgca ccatcgaagg cccgttgtac gttgccgggg cgccgctggc ccagggcgaa    360
```

gcgcgcatgg acgacggcac tgacccaggc gtggtgatgt tccttcaggg ccaggtgttc 420
gatgccgacg gcaagccgtt ggccggtgcc accgtcgacc tgtggcacgc caatacccag 480
ggcacctatt cgtacttcga ttcgacccag tccgagttca acctgcgtcg gcgtatcatc 540
accgatgccg agggccgcta ccgcgcgcgc tcgatcgtgc cgtccgggta tggctgcgac 600
ccgcagggcc caacccagga atgcctggac ctgctcggcc gccacggcca gcgcccggcg 660
cacgtgcact tcttcatctc ggcaccgggg caccgccacc tgaccacgca gatcaacttt 720
gctggcgaca agtacctgtg ggacgacttt gcctatgcca cccgcgacgg gctgatcggc 780
gaactgcgtt ttgtcgagga tgcggcggcg gcgcgcgacc gcggtgtgca aggcgagcgc 840
tttgccgagc tgtcattcga cttccgcttg cagggtgcca agtcgcctga cgccgaggcg 900
cgaagccatc ggccgcgggc gttgcaggag ggctga 936

<210> SEQ ID NO 6
<211> LENGTH: 1371
<212> TYPE: DNA
<213> ORGANISM: Citrobacter braakii

<400> SEQUENCE: 6
atgaattatc cggcagaacc cttccgtatt aaaagcgttg aaactgtatc tatgatcccg 60
cgtgatgaac gcctcaagaa aatgcaggaa gcgggttaca atactttcct gttaaattcg 120
aaagatattt atattgacct gctgacagac agtggcacta acgcaatgag cgacaagcag 180
tgggccggaa tgatgatggg tgatgaagcg tacgcgggca gcgaaaactt ctatcatctg 240
gaaagaaccg tgcaggaact gttcggcttt aaacatattg ttccgactca ccaggggcgt 300
ggcgcagaaa acctgttatc gcagttggct attaaacctg ggcaatatgt tgccgggaat 360
atgtatttca ccaccacccg ttatcaccag gaaaaaaatg gtgcggtgtt tgtcgatatc 420
gttcgtgacg aagcgcacga tgccggtctg aatattgcgt ttaaaggtga tatcgatctt 480
aaaaaattac aaaagctgat tgatgaaaaa ggcgcagaaa atattgcgta tatctgcctg 540
gcggtgacgg ttaacctcgc aggtgggcag ccggtctcga tggccaacat gcgtgcggtg 600
cgtgaactga cagaagcgca cggcattaaa gtgttctacg acgccacccg ttgcgtggaa 660
aacgcctact ttatcaaaga gcaagagcag ggctttgaga acaagagcat cgccgagatc 720
gtgcatgaga tgttcagcta cgccgacggt tgtaccatga gtggtaaaaa agactgtctg 780
gtgaacatcg gcggtttcct gtgcatgaac gatgacgaaa tgttctcttc tgccaaagag 840
ttagtcgtgg tctacgaagg gatgccatct tacggcggcc tggccggacg tgatatggaa 900
gccatggcga ttggcctgcg cgaagccatg caatacgaat atattgagca ccgcgtgaag 960
caggttcgct acctgggcga taagctgaaa gccgctggcg taccgattgt tgaaccggta 1020
ggcggtcacg cggtattcct cgatgcgcgt cgcttctgcg agcatctgac gcaggacgag 1080
ttcccggcgc aaagcctggc ggcgagcatt tatgtggaaa ctggtgtgcg cagtatggaa 1140
cgcggaataa tctctgcagg ccgtaataac gtgaccggtg aacaccacag accgaaactg 1200
gaaaccgtgc gtctgactat tccacgccgc gtttatacct acgcgcacat ggatgtcgta 1260
gctgacggta ttattaaact ttaccagcac aaagaagata ttcgcgggct gaagtttatt 1320
tacgagccga agcagttgcg tttctttact gcacgctttg actatatcta a 1371

<210> SEQ ID NO 7
<211> LENGTH: 498
<212> TYPE: DNA

<213> ORGANISM: Escherichia coli

<400> SEQUENCE: 7

```
atgtcacacc ccgcgttaac gcaactgcgt gcgctgcgct attgtaaaga gatccctgcc     60
ctggatccgc aactgctcga ctggctgttg ctggaggatt ccatgacaaa acgttttgaa    120
cagcagggaa aaacggtaag cgtgacgatg atccgcgaag ggtttgtcga gcagaatgaa    180
atccccgaag aactgccgct gctgccgaaa gagtctcgtt actggttacg tgaaattttg    240
ttatgtgccg atggtgaacc gtggcttgcc ggtcgtaccg tcgttcctgt gtcaacgtta    300
agcgggccgg agctggcgtt acaaaaattg ggtaaaacgc cgttaggacg ctatctgttc    360
acatcatcga cattaacccg ggactttatt gagataggcc gtgatgccgg gctgtggggg    420
cgacgttccc gcctgcgatt aagcggtaaa ccgctgttgc taacagaact gtttttaccg    480
gcgtcaccgt tgtactaa                                                  498
```

<210> SEQ ID NO 8
<211> LENGTH: 2158
<212> TYPE: DNA
<213> ORGANISM: Klebsiella pneumoniae

<400> SEQUENCE: 8

```
atgggccaaa accaccatcg agctggaaac gccctggaca gcgcgcgaag tggccgcgct     60
ggcggacttt tcccacagcc cggcagacca ggccgccacc atctcttccg gttcatttcg    120
taccgacggc atgatcgtta ttccctgcag tatgaaaacg ctggcaggca ttcgcgcggg    180
ttatgccgaa gggctggtgg gccgcgcggc ggacgtggtg ctcaaagagg ggcgcaagct    240
ggtgctggtc ccgcgggaaa tgccgctcag cacgatccat ctggagaaca tgctggcgct    300
gtcgcgcatg ggcgtggcga tggtgccgcc gatgccggct tactacaacc acccggagac    360
ggttgacgat atcaccaatc atatcgtcac ccgggtgctg gatcagtttg gcctcgacta    420
tcacaaagcg cgccgctgga acggcttgcg cacggcagaa caatttgcac aggagatcga    480
ataatggctt ttgatgattt gcgcagcttt ttgcaggcgc tggatgacca gggacaactg    540
ctgaaaatca gtgaagaggt gaacgctgag cccgatctgg cggcggccgc caatgcgacc    600
ggacgcatcg gcgacggcgc cccggcgctg tggttcgata atattcgcgg ctttaccgac    660
gcccgcgtga cgatgaacac catcggctcg tggcagaacc atgccatctc gctgggcctg    720
ccgcctaaca cgccggtgaa aaagcagatt gatgaattca ttcgccgctg ggataacttc    780
ccggtgacgc cagagcgccg cgccaacccg gcgtgggcgg aaaacaccgt ggatggcgac    840
gatatcaacc tgttcgatat tctgccactg ttccgcctca acgatggtga cggcggtttc    900
tacctcgata aagcctgtgt cgtatcacgc gacccgcttg atcctgacaa cttcggtaag    960
caaaacgtcg gtatctaccg catggaagtg aaaggcaagc gcaagctcgg cctgcagccg   1020
gtgccgatgc acgatatcgc gctgcatctg cacaaagcgg aagagcgtgg ggaagatctg   1080
ccgatcgcta ttaccctcgg taacgacccg attattaccc tgatgggcgc cacgccgctg   1140
aaatacgatc aatcagaata tgaaatggct ggcgcgctgc gcgagagccc gtatcccatc   1200
gccaccgcgc cgctgaccgg ctttgacgtg ccctggggtt cggaagtgat cctcgaaggg   1260
gtcattgaag ggcgtaagcg tgagatcgag gggccgttcg gtgagtttac cggtcactac   1320
tccggcggtc gtaacatgac ggtagtgcgt atcgacaaag tctcgtatcg cagcaaaccg   1380
atttttgaat cgctctatct cggtatgccg tggaccgaga ttgactatct gatgggcccg   1440
gcgacctgcg tgccgctgta tcagcagttg aaggcagagt tcccggaagt gcaggcggtc   1500
```

```
aacgccatgt acacccatgg tctgctggcg atcatctcca ccaaaaaacg ctacggcggt   1560

tttgcccgcg cggtgggcct gcgggcgatg accactccgc acggcctcgg ctatgtgaag   1620

atggtgatca tggttgatga agacgtcgac ccgttcaacc tgccgcaggt gatgtgggcg   1680

ctctcctcga aagttaaccc ggcgggtgac ctggtgcagt tgccgaacat gtcggtcctt   1740

gaacttgacc ctggctccag cccggcaggc atcaccgaca aactgattat cgacgccacc   1800

accccggttg cgccggacct tcgcggccac tacagccagc cggtgcagga tctgccggaa   1860

accaaagcct gggctgaaaa actgaccgct atgctggcca accgtaaata aggagaagaa   1920

gatgatttgt ccacgttgcg ccgatgaaaa gattgaagtg atggcaacct cgccggtgaa   1980

aggggtctgg accgtgtatc agtgccagca ctgtctttac acctggcgag ataccgagcc   2040

gctgcgccgc accagtcgcg aacactatcc ggaagcgttc cgcatgacgc agaaagatat   2100

tgatgaggca ccgcaggtgc cacacgtacc gccgctattg ccggaagata agcgttaa     2158
```

<210> SEQ ID NO 9
<211> LENGTH: 1185
<212> TYPE: DNA
<213> ORGANISM: Pseudomonas aeruginosa

<400> SEQUENCE: 9

```
atgaagactc aagtcgccat catcggcgcc ggtccgtccg gcctcctgct cggccagttg     60

ctgcacaagg ccggcatcga caacgtgatc ctcgaacgcc agaccccgga ctacgtgctc    120

ggccgcatcc gcgccggcgt gctggaacag ggtatggtcg acctgctgcg cgaggccggc    180

gtcgaccggc gcatggcgcg cgacgggctg gtccacgaag gcgtggagat cgccttcgcc    240

gggcagcgcc ggcgcatcga cctgaagcgc ctgagcggcg gcaagacggt gacggtctac    300

ggccagaccg aggtcacccg cgacctcatg gaggcccgcg aagcctgcgg cgccactacc    360

gtctaccagg ccgccgaggt gcgcctgcac gacctgcaag gtgagcgccc ctacgtgacc    420

ttcgaacgcg acggcgaacg gctgcgcctg gattgcgact acatcgccgg ctgcgatggc    480

ttccacggca tctcgcggca atcgatcccg gcggagcggc tgaaggtctt cgagcgggtc    540

tatccgttcg gctggctcgg cctgctcgcc gacaccccgc cggtgagcca cgaactgatc    600

tacgccaacc atccgcgcgg cttcgccctg tgcagccagc gttcggccac ccgcagccgc    660

tactacgtgc aggtgccatt gtcggagaag gtcgaggact ggtccgacga gcgcttctgg    720

acggaactga aggcgcgact cccgtccgag gtggcggaga aactggtgac cggaccttcg    780

ctggagaaga gcatcgcgcc gctgcgcagc ttcgtggtcg agccgatgca gcatggccgg    840

ctgttcctcg ccggcgacgc cgcgcacatc gtgccgccca ccggcgccaa gggactgaac    900

ctggccgcca gcgacgtcag cacgctctac cggctgctgc tgaaggccta ccgcgaaggg    960

cgcggcgaac tgctggaacg ctactcggca atctgcctgc ggcggatctg gaaggccgaa   1020

cgcttctcct ggtggatgac ttcggtgctg catcgcttcc ccgacaccga cgcgttcagc   1080

cagcgcatcc agcagaccga actggagtat tacctgggct ccgaggcggg cctggcgacc   1140

atcgccgaga actatgtcgg cctgccctac gaggaaatcg agtag                   1185
```

<210> SEQ ID NO 10
<211> LENGTH: 1509
<212> TYPE: DNA
<213> ORGANISM: Klebsiella pneumoniae

<400> SEQUENCE: 10

```
atgaccgcac cgattcagga tctgcgcgac gccatcgcgc tgctgcaaca gcatgacaat     60

cagtatctcg aaaccgatca tccggttgac cctaacgccg agctggccgg tgtttatcgc    120

catatcggcg cgggcggcac cgtgaagcgc cccacccgca tcgggccggc gatgatgttt    180

aacaatatta agggttatcc acactcgcgc attctggtgg gtatgcacgc cagccgccag    240

cgggccgcgc tgctgctggg ctgcgaagcc tcgcagctgg cccttgaagt gggtaaggcg    300

gtgaaaaaac cggtcgcgcc ggtggtcgtc ccggccagca gcgccccctg ccaggaacag    360

atctttctgg ccgacgatcc ggattttgat ttgcgcaccc tgcttccggc gcacaccaac    420

acccctatcg acgccggccc cttcttctgc ctgggcctgg cgctggccag cgatcccgtc    480

gacgcctcgc tgaccgacgt caccatccac cgcttgtgcg tccagggccg ggatgagctg    540

tcgatgtttc ttgccgccgg ccgccatatc gaagtgtttc gccaaaaggc cgaggccgcc    600

ggcaaaccgc tgccgataac catcaatatg ggtctcgatc cggccatcta tattggcgcc    660

tgcttcgaag cccctaccac gccgttcggc tataatgagc tgggcgtcgc cggcgcgctg    720

cgtcaacgtc cggtggagct ggttcagggc gtcagcgtcc cggagaaagc catcgcccgc    780

gccgagatcg ttatcgaagg tgagctgttg cctggcgtgc gcgtcagaga ggatcagcac    840

accaatagcg gccacgcgat gccggaattt cctggctact gcggcggcgc taatccgtcg    900

ctgccggtaa tcaaagtcaa agcagtgacc atgcgaaaca atgcgattct gcagaccctg    960

gtgggaccgg gggaagagca taccaccctc gccggcctgc caacggaagc cagtatctgg   1020

aatgccgtcg aggccgccat tccgggcttt ttacaaaatg tctacgccca caccgcgggt   1080

ggcggtaagt tcctcgggat cctgcaggtg aaaaaacgtc aacccgccga tgaaggccgg   1140

caggggcagg ccgcgctgct ggcgctggcg acctattccg agctaaaaaa tattattctg   1200

gttgatgaag atgtcgacat ctttgacagc gacgatatcc tgtgggcgat gaccacccgc   1260

atgcaggggg acgtcagcat tacgacaatc cccggcattc gcggtcacca gctggatccg   1320

tcccagacgc cggaatacag cccgtcgatc cgtggaaatg gcatcagctg caagaccatt   1380

tttgactgca cggtcccctg ggcgctgaaa tcgcactttg agcgcgcgcc gtttgccgac   1440

gtcgatccgc gtccgtttgc accggagtat ttcgcccggc tggaaaaaaa ccagggtagc   1500

gcaaaataa                                                           1509
```

<210> SEQ ID NO 11
<211> LENGTH: 1857
<212> TYPE: DNA
<213> ORGANISM: Corynebacterium glutamicum

<400> SEQUENCE: 11

```
atgcgtacat ccattgccac tgtttgtttg tccggaactc ttgctgaaaa gctgcgcgca     60

gctgcagatg ctggatttga tggtgtggaa atcttcgagc aggacttggt ggtttccccg    120

cattcggcag agcagattcg tcagcgggct caggatttgg gattaaccct ggatctgttc    180

cagccgtttc gagatttcga aggtgtggaa gaagagcagt ttctgaagaa tctgcaccgc    240

ttggaagaga agttcaagct gatgaacagg cttggcattg agatgatctt gttgtgttcc    300

aatgtgggca ccgcgaccat caatgatgat gacctttcg tggagcagtt gcatcgtgca    360

gcagatttgg ctgagaagta caacgtcaag attgcttatg aagcgttggc gtggggcaag    420

tttgtcaatg attttgagca tgcgcatgca cttgtggaga aggtgaatca caaggcgctg    480

ggaacctgct tggatacgtt ccatattctt tcccgtggtt gggaaaccga cgaggtggag    540

aacatccctg cggagaagat cttctttgtt cagttagcgg atgcgccgaa gctgagcatg    600
```

```
gacattttgt cctggtcgcg tcaccaccgt gttttccctg gtgaaggcga tttcgatctg    660
gtgaaattca tggttcatct ggccaagacg ggttatgatg gcccgatttc tttggagatc    720
ttcaacgatt ccttccgcaa ggccgaggtt ggtcgcaccg cgattgatgg gttgcgttct    780
ttgcgttggt tggaagatca gacctggcat gcgctaaatg ctgaggatcg tccaagcgct    840
cttgaactgc gtgcacttcc tgaggtcgcg gaacctgagg gtgttgattt cattgagatc    900
gccactggac gtttgggtga gaccattcgg gttcttcatc aattgggttt ccgcttgggt    960
ggtcatcact gcagtaagca ggattaccag gtatggaccc agggcgatgt gcgcattgtg   1020
gtgtgtgatc gtggggtcac cggggctcca accacgatct ctgcgatggg ctttgacacc   1080
cccgatccag aagctgctca tgcccgtgcg gaattgctgc gggctcagac aattgatcgt   1140
ccccacatcg agggcgaagt tgacctaaaa ggtgtgtacg caccggatgg ggtggagctg   1200
tttttcgcgg ggccgagccc cgatggaatg cccgagtggc tgccggaatt cggcgtcgaa   1260
aagcaagaag ctggtctcat tgaagccatc gaccacgtca atttcgccca gccgtggcaa   1320
cattttgatg aggcagtgct gttttacacc gcgctgatgg cgttggagac tgtgcgtgag   1380
gatgagttcc cgagcccaat tggtttggtg cgcaatcagg tgatgcgttc gccgaatgat   1440
gcggtgcggt tgctgctcag cgtggcgccg gaggacggtg agcagggaga tttcctcaac   1500
gcggcctacc cggagcacat tgcgttggcc acggcggaca tcgtggcggt ggctgaacgt   1560
gcgcgcaaac gaggcctgga tttcttgccc gtcccagaga attactacga cgatgtgcag   1620
gcgcgttttg atttgccgca ggaattcttg gacacactca aggaaaacca cctgctttac   1680
gaccgcgacg agaacggcga attcctccac ttttacaccc gcacgttggg cacgctgttc   1740
ttcgaagtgg tggaacgccg cggcggtttt gcaggttggg gcgaaacaaa cgctccggtg   1800
cggttggcgg cgcagtatcg tgaggtgcgg gacctcgagc ggggaatccc aaactag      1857
```

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 12

```
ataggatcca ggaggataaa taatggatac gtcactggct ga                        42
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 13

```
attctgcagt taatgcaatc caaaaacgtt                                      30
```

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
aatatctaga ttcccgagag gttgcatgat gaaaact 37

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
attggatcct tatgcggcac cccgtgtctg g 31

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
atagaattca ggaggataaa taatgcgtgg taaagttagc ctg 43

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
attggatcct taggcttcgc tgtcatagaa t 31

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
atatctagaa ggaggataaa tagagctcgt gctgcctcac ga 42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
attcctgcag gatgcccatg actatatctt cttgaacagg gc 42

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ataagatcta ggaggataaa taatgaccgt gaaaatttcc cac 43

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
atttctagat cagccctcct gcaacgc 27

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
atagaattca ggaggataaa taatgaatta tccggcagaa cc 42

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
atttctagat tagatatagt caaagcgtgc agta 34

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
atagaattca ggaggataaa taatgtcaca ccccgcgtta acg 43

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
attagatctt tagtacaacg gtgacgccgg taaa 34

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ataggatccc ccgtccggag agggtaattt aaatataaag ttcg 44

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
attaagcttc ttagcgggcc cctttattaa cgct 34

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
atatctagaa ggaggataaa taatgaagac tcaagtcgcc atcatcg 47

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tataagcttt actcgatttc ctcgtagggc 30

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ataaagctta ggaggataaa taatgaccgc accgattc 38

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
attctcgagt tattttgcgc taccctggtt tttttccagc 40

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ataggatcca ggaggataaa taatgcgtac atccattgcc actgtttg 48

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
attaagcttc tagtttggga ttccccgctc ga 32

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
agatctaaag gaggccatcc atggctggaa acacaattgg 40

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
atgcctggag atccttactc gagtttggat cctc 34

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gaggatccaa actcgagtaa ggatctccag gcat 34

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ccaattgtgt ttccagccat ggatggcctc ctttagatct 40

<210> SEQ ID NO 38
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ctgcacgctt tgactatatc taaggatcca aactcgagta agg 43

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
catggatggc ctcctagatc ttttgaattc tgaaattgtt atc 43

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gataacaatt tcagaattca aaagatctag gaggccatcc atg 43

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
cggataattc attatttatc ctcctttaga tccttactgg cgatt 45

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
aatcgccagt aaggatctaa aggaggataa ataatgaatt atccg 45

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ccttactcga gtttggatcc ttagatatag tcaaagcgtg cag 43

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aaggaggcca tccatgcgtg gtaaagttag c 31

<210> SEQ ID NO 45

<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gtttggatcc ttaatgcaat ccaaaaacg 29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
attgcattaa ggatccaaac tcgagtaag 29

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ctttaccacg catggatggc ctcctttaga tc 32

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cgtgtgaaac agaatgcgaa gacgaacaat a 31

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
taatccagtg ccggatgatt cacatcatc 29

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
atcgcggcgt tatttcattc ggatt 25

<210> SEQ ID NO 51
<211> LENGTH: 20

<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aactgtaggc cggatgtggc 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gcgaggcacc accactttcg 20

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
agcgcccatc agggcg 16

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ctatgagcgc catttctatc ccgcgc 26

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
cctgaaaggg actggcgacc tg 22

<210> SEQ ID NO 56
<211> LENGTH: 1122
<212> TYPE: DNA
<213> ORGANISM: Escherichia coli

<400> SEQUENCE: 56
atggttgctg aattgaccgc attacgcgat caaattgatg aagtcgataa agcgctgctg 60
aatttattag cgaagcgtct ggaactggtt gctgaagtgg gcgaggtgaa aagccgcttt 120
ggactgccta tttatgttcc ggagcgcgag gcatctatgt tggcctcgcg tcgtgcagag 180
gcggaagctc tgggtgtacc gccggatctg attgaggatg ttttgcgtcg ggtgatgcgt 240
gaatcttact ccagtgaaaa cgacaaagga tttaaaacac tttgtccgtc actgcgtccg 300

```
gtggttatcg tcggcggtgg cggtcagatg ggacgcctgt tcgagaagat gctgaccctc    360

tcgggttatc aggtgcggat tctggagcaa catgactggg atcgagcggc tgatattgtt    420

gccgatgccg gaatggtgat tgttagtgtg ccaatccacg ttactgagca agttattggc    480

aaattaccgc ctttaccgaa agattgtatt ctggtcgatc tggcatcagt gaaaaatggg    540

ccattacagg ccatgctggt ggcgcatgat ggtccggtgc tggggctaca cccgatgttc    600

ggtccggaca gcggtagcct ggcaaagcaa gttgtggtct ggtgtgatgg acgtaaaccg    660

gaagcatacc aatggtttct ggagcaaatt caggtctggg gcgctcggct gcatcgtatt    720

agcgccgtcg agcacgatca gaatatggcg tttattcagg cactgcgcca ctttgctact    780

tttgcttacg ggctgcacct ggcagaagaa aatgttcagc ttgagcaact tctggcgctc    840

tcttcgccga tttaccgcct tgagctggcg atggtcgggc gactgtttgc tcaggacccg    900

cagctttatg ccgacatcat tatgtcgtca gagcgtaatc tggcgttaat caaacgttac    960

tataagcgtt tcggcgaggc gattgagttg ctggagcagg gcgataagca ggcgtttatt   1020

gacagtttcc gcaaggtgga gcactggttc ggcgattacg cacagcgttt tcagagtgaa   1080

agccgcgtgt tattgcgtca ggcgaatgac aatcgccagt aa                      1122


<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

ataccatgga ggaggataaa taatgcgtgg taaagttagc ctg                       43


<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

atacctgcag gaggaggata aataatgacc gtgaaaattt cccacactgc                50


<210> SEQ ID NO 59
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

ataaagcttg gaggaggata aataatgacc gtgaaaattt cccacactgc                50
```